US010552557B2

(12) United States Patent
Frankenbach et al.

(10) Patent No.: US 10,552,557 B2
(45) **Date of Patent: *Feb. 4, 2020**

(54) FRESHENING COMPOSITIONS AND DEVICES COMPRISING SAME

(71) Applicant: The Procter & Gamble Company, Cincinnati, OH (US)

(72) Inventors: Gayle Marie Frankenbach, Cincinnati, OH (US); Judith Ann Hollingshead, Batavia, OH (US); Steven Anthony Horenziak, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/865,089

(22) Filed: Sep. 25, 2015

(65) Prior Publication Data

US 2016/0089462 A1 Mar. 31, 2016

Related U.S. Application Data

(60) Provisional application No. 62/055,844, filed on Sep. 26, 2014, provisional application No. 62/143,862, filed on Apr. 7, 2015.

(51) Int. Cl.

| | |
|---|---|
| ***G06F 17/50*** | (2006.01) |
| ***G16C 10/00*** | (2019.01) |
| ***G16C 20/40*** | (2019.01) |
| ***A61Q 19/00*** | (2006.01) |
| ***C11B 9/00*** | (2006.01) |
| ***A61K 8/33*** | (2006.01) |

(Continued)

(52) U.S. Cl.

CPC ............ *G06F 17/5018* (2013.01); *A61K 8/11* (2013.01); *A61K 8/31* (2013.01); *A61K 8/33* (2013.01); *A61K 8/34* (2013.01); *A61K 8/342* (2013.01); *A61K 8/35* (2013.01); *A61K 8/36* (2013.01); *A61K 8/361* (2013.01); *A61K 8/368* (2013.01); *A61K 8/37* (2013.01); *A61K 8/494* (2013.01); *A61K 8/498* (2013.01); *A61K 8/4926* (2013.01); *A61K 8/4966* (2013.01); *A61K 8/4973* (2013.01); *A61K 8/58* (2013.01); *A61K 8/731* (2013.01); *A61K 8/8152* (2013.01); *A61L 2/18* (2013.01); *A61L 9/01* (2013.01); *A61L 9/012* (2013.01); *A61L 9/03* (2013.01); *A61L 9/122* (2013.01); *A61L 9/127* (2013.01); *A61L 15/20* (2013.01); *A61L 15/28* (2013.01); *A61L 15/46* (2013.01); *A61Q 5/02* (2013.01); *A61Q 13/00* (2013.01); *A61Q 15/00* (2013.01); *A61Q 19/00* (2013.01); *A61Q 19/10* (2013.01); *B01J 20/24* (2013.01); *C08K 5/0008* (2013.01); *C11B 9/003* (2013.01); *C11B 9/008* (2013.01); *C11B 9/0015* (2013.01); *C11B 9/0019* (2013.01); *C11B 9/0034* (2013.01); *C11B 9/0038* (2013.01); *C11B 9/0042* (2013.01); *C11B 9/0049* (2013.01); *C11B 9/0053* (2013.01); *C11B 9/0061* (2013.01); *C11B 9/0076* (2013.01); *C11B 9/0092* (2013.01); *C11D 3/001* (2013.01); *C11D 3/0068* (2013.01); *C11D 3/184* (2013.01); *C11D 3/2034* (2013.01); *C11D 3/2068* (2013.01); *C11D 3/2072* (2013.01); *C11D 3/2079* (2013.01); *C11D 3/2093* (2013.01); *C11D 3/2096* (2013.01); *C11D 3/222* (2013.01); *C11D 3/30* (2013.01); *C11D 3/43* (2013.01); *C11D 3/50* (2013.01); *C11D 3/505* (2013.01); *C11D 11/0017* (2013.01); *C11D 17/0043* (2013.01); *C11D 17/042* (2013.01); *C11D 17/047* (2013.01); *C11D 17/06* (2013.01); *D06B 1/02* (2013.01); *G06F 17/10* (2013.01); *G06F 17/11* (2013.01); *G06Q 99/00* (2013.01); *G16C 10/00* (2019.02); *G16C 20/40* (2019.02); *A61K 2800/56* (2013.01); *A61K 2800/592* (2013.01); *A61K 2800/5922* (2013.01); *A61L 2209/21* (2013.01); *A61L 2300/62* (2013.01)

(58) Field of Classification Search
None
See application file for complete search history.

(56) References Cited

U.S. PATENT DOCUMENTS

| | | | |
|---|---|---|---|
| 2,438,091 | A | 3/1948 | Lynch |
| 2,528,378 | A | 10/1950 | Mannheimer |

(Continued)

FOREIGN PATENT DOCUMENTS

| | | | |
|---|---|---|---|
| BE | 825146 | A1 | 8/1975 |
| CA | 1164347 | A | 3/1984 |

(Continued)

OTHER PUBLICATIONS

Database WPI; Week 201459; Thomson scientific, London, GB; AN 2014-P66521; XP002752638.
International Search Report; International Application No. PCT/US2015/052088; dated Jan. 22, 2016; 16 pages.
International Search Report; International Application No. PCT/US2015/052090; dated Jan. 19, 2016; 13 pages.

(Continued)

*Primary Examiner* — Tigabu Kassa
(74) *Attorney, Agent, or Firm* — Abbey A. Lopez

(57) ABSTRACT

The present invention relates to freshening compositions and devices comprising same that comprise a composition having a viscosity of from about 1 mPa·s to about 50,000 mPa·s comprising malodor reduction compositions and methods of making and using such compositions. The disclosed malodor reduction compositions do not unduely interfere with the scent of the freshening compositions and devices that comprise such technologies and the perfumed or unperfumed situs that is treated with such freshening compositions and devices.

10 Claims, No Drawings

(51) Int. Cl.

| | |
|---|---|
| *A61K 8/35* | (2006.01) |
| *A61K 8/36* | (2006.01) |
| *A61K 8/37* | (2006.01) |
| *A61K 8/49* | (2006.01) |
| *A61K 8/58* | (2006.01) |
| *A61Q 15/00* | (2006.01) |
| *A61K 8/31* | (2006.01) |
| *A61K 8/34* | (2006.01) |
| *A61Q 5/02* | (2006.01) |
| *A61Q 19/10* | (2006.01) |
| *A61L 2/18* | (2006.01) |
| *A61L 9/03* | (2006.01) |
| *A61L 9/12* | (2006.01) |
| *D06B 1/02* | (2006.01) |
| *A61L 9/01* | (2006.01) |
| *C08K 5/00* | (2006.01) |
| *A61L 9/012* | (2006.01) |
| *C11D 3/00* | (2006.01) |
| *C11D 3/18* | (2006.01) |
| *C11D 3/20* | (2006.01) |
| *C11D 3/43* | (2006.01) |
| *C11D 17/04* | (2006.01) |
| *C11D 3/22* | (2006.01) |
| *C11D 3/30* | (2006.01) |
| *C11D 3/50* | (2006.01) |
| *C11D 17/06* | (2006.01) |
| *A61K 8/368* | (2006.01) |
| *G06F 17/10* | (2006.01) |
| *G06Q 99/00* | (2006.01) |
| *A61Q 13/00* | (2006.01) |
| *C11D 11/00* | (2006.01) |
| *A61L 15/20* | (2006.01) |
| *A61L 15/28* | (2006.01) |
| *A61L 15/46* | (2006.01) |
| *B01J 20/24* | (2006.01) |
| *C11D 17/00* | (2006.01) |
| *G06F 17/11* | (2006.01) |
| *A61K 8/11* | (2006.01) |
| *A61K 8/73* | (2006.01) |
| *A61K 8/81* | (2006.01) |

(56) References Cited

U.S. PATENT DOCUMENTS

| | | | |
|---|---|---|---|
| 2,658,072 | A | 11/1953 | Kosmin |
| 2,809,971 | A | 10/1957 | Bernstein et al. |
| 3,236,733 | A | 2/1966 | Karsten et al. |
| 3,716,498 | A | 2/1973 | Hall |
| 3,753,196 | A | 8/1973 | Kurtz et al. |
| 3,761,418 | A | 9/1973 | Parran, Jr. |
| 3,792,068 | A | 2/1974 | Luedders et al. |
| 3,887,692 | A | 6/1975 | Gilman |
| 3,904,741 | A | 9/1975 | Jones et al. |
| 4,049,792 | A | 9/1977 | Elsnau |
| 4,120,948 | A | 10/1978 | Shelton |
| 4,137,180 | A | 1/1979 | Naik et al. |
| 4,237,155 | A | 12/1980 | Kardouche |
| 4,323,683 | A | 4/1982 | Bolich, Jr. et al. |
| 4,345,080 | A | 8/1982 | Bolich, Jr. |
| 4,359,456 | A | 11/1982 | Gosling et al. |
| 4,379,753 | A | 4/1983 | Bolich, Jr. |
| 4,430,243 | A | 2/1984 | Bragg |
| 4,470,982 | A | 9/1984 | Winkler |
| 4,973,416 | A | 11/1990 | Kennedy |
| 4,985,238 | A | 1/1991 | Tanner et al. |
| 5,019,375 | A | 5/1991 | Tanner et al. |
| 5,104,646 | A | 4/1992 | Bolich, Jr. et al. |
| 5,106,609 | A | 4/1992 | Bolich, Jr. et al. |
| 5,296,622 | A | 3/1994 | Uphues et al. |
| 5,429,816 | A | 7/1995 | Hofrichter et al. |
| 5,486,303 | A | 1/1996 | Capeci et al. |
| 5,489,392 | A | 2/1996 | Capeci et al. |
| 5,516,448 | A | 5/1996 | Capeci et al. |
| 5,565,422 | A | 10/1996 | Del Greco et al. |
| 5,569,645 | A | 10/1996 | Dinniwell et al. |
| 5,574,005 | A | 11/1996 | Welch et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,691,297 | A | 11/1997 | Nassano et al. |
| 5,714,137 | A | 2/1998 | Trinh et al. |
| 5,800,897 | A | 9/1998 | Sharma |
| 5,879,584 | A | 3/1999 | Bianchetti et al. |
| 5,891,424 | A | 4/1999 | Bretzler et al. |
| 5,942,217 | A | 8/1999 | Woo et al. |
| 5,976,514 | A | 11/1999 | Guskey et al. |
| 6,180,121 | B1 | 1/2001 | Guenin et al. |
| 6,225,464 | B1 | 5/2001 | Hiler, II et al. |
| 6,248,135 | B1 | 6/2001 | Trinh et al. |
| 6,386,392 | B1 | 5/2002 | Argentieri et al. |
| 6,413,920 | B1 | 7/2002 | Bettiol et al. |
| 6,436,442 | B1 | 8/2002 | Woo et al. |
| 6,488,943 | B1 | 12/2002 | Beerse et al. |
| 6,656,923 | B1 | 12/2003 | Trinh et al. |
| 6,716,805 | B1 | 4/2004 | Sherry et al. |
| 6,794,356 | B2 | 9/2004 | Turner |
| 6,814,088 | B2 | 11/2004 | Barnabas et al. |
| 6,869,923 | B1 | 3/2005 | Cunningham et al. |
| 7,100,767 | B2 | 9/2006 | Chomik |
| 7,172,099 | B2 | 2/2007 | Höfte et al. |
| 7,202,198 | B2 | 4/2007 | Gordon et al. |
| 7,223,361 | B2 | 5/2007 | Kvietok et al. |
| 8,058,500 | B2 | 11/2011 | Sojka |
| 8,158,571 | B2 | 4/2012 | Alonso |
| 8,322,631 | B2 | 12/2012 | Richardson et al. |
| 8,609,600 | B2 | 12/2013 | Warr |
| 8,709,337 | B2 | 4/2014 | Gruenbacher et al. |
| 8,772,354 | B2 | 7/2014 | Williams et al. |
| 8,931,711 | B2 | 1/2015 | Gruenbacher et al. |
| 2003/0192922 | A1 | 10/2003 | Ceppaluni |
| 2004/0064117 | A1 | 4/2004 | Hammons |
| 2004/0151793 | A1 | 8/2004 | Paspaleeva-Kuhn et al. |
| 2005/0003980 | A1 | 1/2005 | Baker et al. |
| 2005/0192207 | A1 | 9/2005 | Morgan |
| 2005/0276831 | A1 | 12/2005 | Dihora et al. |
| 2006/0166857 | A1 | 7/2006 | Surburg |
| 2007/0003499 | A1 | 1/2007 | Shen et al. |
| 2007/0020263 | A1 | 1/2007 | Shitara et al. |
| 2007/0275866 | A1 | 11/2007 | Dykstra |
| 2008/0003245 | A1 | 1/2008 | Kroepke et al. |
| 2008/0176780 | A1 | 7/2008 | Warr |
| 2009/0005280 | A1 | 1/2009 | Woo |
| 2009/0240223 | A1 | 9/2009 | Warren |
| 2009/0312223 | A1 | 12/2009 | Yang |
| 2010/0001116 | A1 | 1/2010 | Johnson |
| 2010/0009285 | A1 | 1/2010 | Daems et al. |
| 2010/0061946 | A1 | 3/2010 | Scherner et al. |
| 2010/0098209 | A1 | 4/2010 | Smets |
| 2010/0287710 | A1 | 11/2010 | Denutte et al. |
| 2010/0322878 | A1 | 12/2010 | Stella et al. |
| 2011/0245134 | A1 | 10/2011 | Smets |
| 2011/0269657 | A1 | 11/2011 | Dihora |
| 2011/0303766 | A1 | 12/2011 | Smith |
| 2011/0308555 | A1* | 12/2011 | Smets .................... A61K 8/738 134/26 |
| 2012/0004328 | A1 | 1/2012 | Huchel et al. |
| 2012/0009285 | A1 | 1/2012 | Wei et al. |
| 2012/0129924 | A1 | 5/2012 | Park et al. |
| 2012/0219610 | A1 | 8/2012 | Smith, III et al. |
| 2012/0230936 | A1 | 9/2012 | Mikkelsen |
| 2012/0237469 | A1* | 9/2012 | Dente ....................... A61L 9/01 424/76.1 |
| 2012/0246851 | A1 | 10/2012 | Smith, III et al. |
| 2012/0258150 | A1 | 10/2012 | Rauckhorst et al. |
| 2013/0043145 | A1 | 2/2013 | Smith, III et al. |
| 2013/0043146 | A1 | 2/2013 | Smith, III et al. |
| 2013/0043147 | A1 | 2/2013 | Smith, III et al. |

(56) References Cited

U.S. PATENT DOCUMENTS

| | | | |
|---|---|---|---|
| 2013/0319463 | A1 | 12/2013 | Policicchio |
| 2014/0201927 | A1 | 7/2014 | Bianchetti et al. |
| 2015/0108163 | A1 | 4/2015 | Smith et al. |
| 2016/0089317 | A1 | 3/2016 | Cetti et al. |
| 2016/0089318 | A1 | 3/2016 | Cetti et al. |
| 2016/0089462 | A1 | 3/2016 | Frankenbach et al. |
| 2016/0089464 | A1 | 3/2016 | Frankenbach et al. |
| 2016/0089465 | A1 | 3/2016 | Frankenbach et al. |
| 2016/0090555 | A1 | 3/2016 | Frankenbach et al. |
| 2016/0090556 | A1 | 3/2016 | Frankenbach et al. |
| 2016/0090557 | A1 | 3/2016 | Frankenbach et al. |
| 2016/0090558 | A1 | 3/2016 | Frankenbach et al. |
| 2016/0092661 | A1 | 3/2016 | Hollingshead et al. |
| 2016/0206522 | A1 | 7/2016 | Ribaut |
| 2016/0296656 | A1 | 10/2016 | Scavone et al. |
| 2016/0306909 | A1 | 10/2016 | Hollingshead et al. |
| 2017/0066579 | A1 | 3/2017 | Zillges |
| 2017/0119917 | A1 | 5/2017 | Frankenbach et al. |
| 2017/0137752 | A1 | 5/2017 | Frankenbach et al. |
| 2017/0137753 | A1 | 5/2017 | Frankenbach et al. |

FOREIGN PATENT DOCUMENTS

| | | | |
|---|---|---|---|
| DE | 10 2004 023720 | A1 | 12/2005 |
| DE | 10 2007 019369 | A1 | 10/2008 |
| EP | 2 005 939 | A1 | 12/2008 |
| GB | 1347950 | A | 2/1974 |
| GB | 2048229 | A | 12/1980 |
| GB | 2144992 | A | 3/1985 |
| GB | 2 450 727 | A | 1/2009 |
| WO | WO 96/04937 | A1 | 2/1996 |
| WO | WO 99/57233 | A1 | 11/1999 |
| WO | WO 00/19822 | A1 | 4/2000 |
| WO | WO 00/32601 | A2 | 6/2000 |
| WO | WO 2011/152886 | A2 | 12/2011 |
| WO | WO 2012/039516 | A1 | 3/2012 |
| WO | WO 2012/136651 | A1 | 10/2012 |
| WO | WO2018100411 | A1 | 6/2018 |

OTHER PUBLICATIONS

International Search Report; International Application No. PCT/US2015/052092; dated Jan. 12, 2016; 13 pages.

International Search Report; International Application No. PCT/US2015/052219; dated Jan. 26, 2016; 13 pages.

International Search Report; International Application No. PCT/US2015/052093; dated Jan. 12, 2016; 13 pages.

International Search Report; International Application No. PCT/US2015/052094; dated Jan. 20, 2016; 11 pages.

International Search Report; International Application No. PCT/US2015/052119; dated Jan. 20, 2016; 13 pages.

International Search Report; International Application No. PCT/US2015/052225; dated Jan. 20, 2016; 16 pages.

International Search Report; International Application No. PCT/US2015/052130; dated Jan. 12, 2016; 13 pages.

International Search Report; International Application No. PCT/US2015/052084; dated Jan. 19, 2016; 13 pages.

International Search Report; International Application No. PCT/US2015/052089; dated Feb. 23, 2016; 11 pages.

U.S. Appl. No. 14/864,927, filed Sep. 25, 2015, Frankenbach, et al.

U.S. Appl. No. 14/865,056, filed Sep. 25, 2015, Scavone, et al.

U.S. Appl. No. 14/864,973, filed Sep. 25, 2015, Hollingshead, et al.

U.S. Appl. No. 14/864,994, filed Sep. 25, 2015, Frankenbach, et al.

U.S. Appl. No. 14/865,010, filed Sep. 25, 2015, Frankenbach, et al.

U.S. Appl. No. 14/865,048, filed Sep. 25, 2015, Cetti, et al.

U.S. Appl. No. 14/865,257, filed Sep. 25, 2015, Cetti, et al.

U.S. Appl. No. 14/865,066, filed Sep. 25, 2015, Frankenbach, et al.

U.S. Appl. No. 14/865,099, filed Sep. 25, 2015, Frankenbach, et al.

U.S. Appl. No. 14/865,412, filed Sep. 25, 2015, Frankenbach, et al.

ASTM D3954-94, Reapproved 2010, vol. 15.04, Standard Test Method for Dropping Point of Waxes.

Todd, C., et al., Volatile silicone fluids for cosmetic formulations, Cosmetics and Toiletries, Jan. 1976, pp. 29-32, vol. 91.

Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.

Morioka, H., et al., Effects of Zinc on the New Preparation Method of Hydroxy Double Salts, Inorganic Chemistry, 1999, pp. 4211-4216, vol. 38, No. 19.

McGinley et al. Performance Verification of Air Freshener Products and Other Odour Control Devices for Indoor Air Quality Malodours. Presented at The 8th Workshop on Odour and Emissions of Plastic Materials Universität Kassel Institut für Werkstofftechnik Kassel, Germany: Mar. 27-28, 2006. 13p.

U.S. Appl. No. 15/597,391, filed May 17, 2017, Cetti, et al.

U.S. Appl. No. 15/597,376, filed May 17, 2017, Cetti, et al.

U.S. Appl. No. 15/432,957, filed Feb. 15, 2017, Frankenbach, et al.

Air Quality Bureau of the Iowa Department of Natural Resources. A Review of the Science and Technology of Odor Measurement. 2005. 51 Pages (Year: 2005).

Bratttoli et al. Odour Detection methods; Olfactometry and chemical sensors. Sensors (Basel). 2011; 11(5): 5290-5322. (Year: 2011).

McGinley et al. American Association of Textile Chemists and Colorists. 2017. 17 Pages. (Year: 2017).

* cited by examiner

FRESHENING COMPOSITIONS AND DEVICES COMPRISING SAME

FIELD OF THE INVENTION

The present invention relates to freshening compositions and devices comprising same that comprise a composition having a viscosity of from about 1 mPa·s to about 50,000 mPa·s comprising malodor reduction compositions and methods of making and using such compositions.

BACKGROUND OF THE INVENTION

Unscented or scented products are desired by consumers as they may be considered more natural and discreet than scented products. Manufacturers of unscented or scented products for controlling malodors rely on malodor reduction ingredients or other technologies (e.g. filters) to reduce malodors. However, effectively controlling malodors, for example, amine-based malodors (e.g. fish and urine), thiol and sulfide-based malodors (e.g. garlic and onion), $C_2$-$C_{12}$ carboxylic acid based malodors (e.g. body and pet odor), indole based malodors (e.g. fecal and bad breath), short chain fatty aldehyde based malodors (e.g. grease) and geosmin based malodors (e.g. mold/mildew) may be difficult, and the time required for a product to noticeably reduce malodors may create consumer doubt as to the product's efficacy on malodors. Often times, manufacturers incorporate scented perfumes to help mask these difficult malodors.

Unfortunately, malodor control technologies typically cover up the malodor with a stronger scent and thus interfere with the scent of the perfumed or unperfumed situs that is treated with the malodor control technology. Thus, limited nature of the current malodor control technologies is extremely constraining. Thus what is needed is a broader palette of malodor control technologies so the perfume community can deliver the desired level of character in a greater number of situations/applications. Surprisingly, Applicants recognized that in addition to blocking a malodor's access to a sensory cell, in order to achieve the desired goal, a malodor control technology must leave such sensor cell open to other molecules, for example scent molecules. As a result, the disclosed malodor reduction compositions do not unduely interfere with the scent of the freshening compositions and devices that comprise such technologies and the perfumed or unperfumed situs that is treated with such freshening compositions and devices.

SUMMARY OF THE INVENTION

The present invention relates to freshening compositions and devices comprising same that comprise a composition having a viscosity of from about 1 mPa·s to about 50,000 mPa·s comprising malodor reduction compositions and methods of making and using such compositions. The disclosed malodor reduction compositions do not unduely interfere with the scent of the freshening compositions and devices that comprise such technologies and the perfumed or unperfumed situs that is treated with such freshening compositions and devices.

DETAILED DESCRIPTION OF THE INVENTION

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

As used herein, "malodor" refers to compounds generally offensive or unpleasant to most people, such as the complex odors associated with bowel movements.

As used herein, "neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Neutralization is distinguishable from odor masking or odor blocking by a change in the malodorous compound, as opposed to a change in the ability to perceive the malodor without any corresponding change in the condition of the malodorous compound. Malodor neutralization provides a sensory and analytically measurable (e.g. gas chromatograph) malodor reduction. Thus, if a malodor reduction composition delivers genuine malodor neutralization, the composition will reduce malodors in the vapor and/or liquid phase.

As used herein, "odor blocking" refers to the ability of a compound to dull the human sense of smell.

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Malodor Reduction Materials

A non-limiting set of suitable malodor reduction materials are provided in the tables below. For ease of use, each material in Tables 1-3 is assigned a numerical identifier which is found in the column for each table that is designated Number. Table 4 is a subset of Table 1, Table 5 is a subset of Table 2 and Table 6 is a subset of Table 3 and there for Tables 4, 5 and 6 each use the same numerical identifier as found, respectively, in Tables 1-3.

Codes

A=Vapor Pressure>0.1 torr

B=Vapor Pressure is between 0.01 torr and 0.1 torr

C=log P<3

D=log P>3

E=Probability of Ingredient Color Instability=0%

F=Probability of Ingredient Color Instability<71%

G=Odor Detection Threshold less than p.ol=8

H=Odor Detection Threshold greater than p.ol=8

I=Melamine formaldehyde PMC Headspace Response Ratio greater than or equal to 10

J=Melamine formaldehyde PMC leakage less than or equal to 5%

K=Log of liquid dish neat product liquid-air partition coefficient greater than or equal to −7

L=Log of liquid dish neat product liquid-air partition coefficient greater than or equal to −5

TABLE 1

List of materials with at least one MORV from 1 to 5

| Number | Material Name | CAS Number | Comment Code |
|---|---|---|---|
| 1 | 2-ethylhexyl (Z)-3-(4-methoxyphenyl)acrylate | 5466-77-3 | DEFHJ |
| 2 | 2,4-dimethyl-2-(5,5,8,8-tetramethyl-5,6,7,8-tetrahydronaphthalen-2-yl)-1,3-dioxolane | 131812-67-4 | DFHJ |
| 3 | 1,1-dimethoxynon-2-yne | 13257-44-8 | ACEFHJK |
| 4 | para-Cymen-8-ol | 1197-01-9 | BCGIJK |
| 7 | 3-methoxy-7,7-dimethyl-10-methylenebicyclo[4.3.1]decane | 216970-21-7 | BDEFHJK |
| 9 | Methoxycyclododecane | 2986-54-1 | DEFHJK |
| 10 | 1,1-dimethoxycyclododecane | 950-33-4 | DEFHJK |
| 11 | (Z)-tridec-2-enenitrile | 22629-49-8 | DEFHJK |
| 13 | Oxybenzone | 131-57-7 | DEFGJ |
| 14 | Oxyoctaline formate | 65405-72-3 | DFHJK |
| 16 | 4-methyl-1-oxaspiro[5.5]undecan-4-ol | 57094-40-3 | CFGIJK |
| 17 | 7-methyl-2H-benzo[b][1,4]dioxepin-3(4H)-one | 28940-11-6 | CGIK |
| 18 | 1,8-dioxacycloheptadecan-9-one | 1725-01-5 | DGJ |
| 21 | 4-(tert-pentyl)cyclohexan-1-one | 16587-71-6 | ADFGIJKL |
| 22 | o-Phenyl anisol | 86-26-0 | DEFHJK |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 25 | 7-isopropyl-8,8-dimethyl-6,10-dioxaspiro[4.5]decane | 62406-73-9 | BDEFHIJK |
| 28 | Octyl 2-furoate | 39251-88-2 | DEFHJK |
| 29 | Octyl acetate | 112-14-1 | BDEFHJKL |
| 30 | octanal propylene glycol acetal | 74094-61-4 | BDEFHJKL |
| 31 | Octanal | 124-13-0 | ACHIKL |
| 32 | Octanal dimethyl acetal | 10022-28-3 | ACEFGJKL |
| 33 | Myrcene | 123-35-3 | ADEFGIKL |
| 34 | Myrcenol | 543-39-5 | BCEFGIJK |
| 35 | Myrcenyl acetate | 1118-39-4 | ADEFGJK |
| 36 | Myristaldehyde | 124-25-4 | DFHJK |
| 37 | Myristicine | 607-91-0 | CGJK |
| 38 | Myristyl nitrile | 629-63-0 | DEFHJK |
| 39 | 2,2,6,8-tetramethyl-1,2,3,4,4a,5,8,8a-octahydronaphthalen-1-ol | 103614-86-4 | DEFHIJK |
| 42 | Ocimenol | 5986-38-9 | BCHIJK |
| 43 | Ocimenol | 28977-58-4 | BCHIJK |
| 47 | Nopyl acetate | 128-51-8 | DEFHJK |
| 48 | Nootkatone | 4674-50-4 | DHJK |
| 49 | Nonyl alcohol | 143-08-8 | BDEFGIJKL |
| 50 | Nonaldehyde | 124-19-6 | ADHIKL |
| 52 | 12-methyl-14-tetradec-9-enolide | 223104-61-8 | DFHJK |
| 57 | N-ethyl-p-menthane-3-carboxamide | 39711-79-0 | DEFGIJK |

TABLE 1-continued

List of materials with at least one MORV from 1 to 5

| Number | Material Name | CAS Number | Comment Code |
|---|---|---|---|
| 61 | 1-(3-methylbenzofuran-2-yl)ethan-1-one | 23911-56-0 | CEFHIK |
| 62 | 2-methoxynaphthalene | 93-04-9 | BDEFHK |
| 63 | Nerolidol | 7212-44-4 | DEFHJK |
| 64 | Nerol | 106-25-2 | BCHIK |
| 65 | 1-ethyl-3-methoxytricyclo[2.2.1.02,6]heptane | 31996-78-8 | ACEFHIJKL |
| 67 | Methyl (E)-non-2-enoate | 111-79-5 | ADEFHJKL |
| 68 | 10-isopropyl-2,7-dimethyl-1-oxaspiro[4.5]deca-3,6-diene | 89079-92-5 | BDEFHIJK |
| 69 | 2-(2-(4-methylcyclohex-3-en-1-yl)propyl)cyclopentan-1-one | 95962-14-4 | DHJK |
| 70 | Myrtenal | 564-94-3 | ACFHIJKL |
| 71 | (E)-4-(2,2,3,6-tetramethylcyclohexyl)but-3-en-2-one | 54992-90-4 | BDEFHIJK |
| 74 | Myraldyl acetate | 53889-39-7 | DHJK |
| 75 | Musk tibetine | 145-39-1 | DHIJ |
| 76 | 1,7-dioxacycloheptadecan-8-one | 3391-83-1 | DGJ |
| 77 | Musk ketone | 81-14-1 | DHJ |
| 78 | Musk ambrette | 83-66-9 | DHIJ |
| 79 | 3-methylcyclopentadecan-1-one | 541-91-3 | DEFHJK |
| 80 | (E)-3-methylcyclopentadec-4-en-1-one | 82356-51-2 | DHJK |
| 82 | 3-methyl-4-phenylbutan-2-ol | 56836-93-2 | BCEFHIK |
| 83 | 1-(4-isopropylcyclohexyl)ethan-1-ol | 63767-86-2 | BDEFHIJK |
| 85 | Milk Lactone | 72881-27-7 | DEFHJK |
| 91 | Methyl octine carbonate | 111-80-8 | BDEFHKL |
| 92 | Methyl octyl acetaldehyde | 19009-56-4 | ADFHJKL |
| 93 | 6,6-dimethoxy-2,5,5-trimethylhex-2-ene | 67674-46-8 | ACHIJKL |
| 98 | Methyl phenylethyl carbinol | 2344-70-9 | BCEFHIK |
| 100 | Methyl stearate | 112-61-8 | DEFHJ |
| 101 | Methyl nonyl acetaldehyde dimethyl acetal | 68141-17-3 | BDEFHJK |
| 102 | Methyl nonyl ketone | 112-12-9 | BDFHJKL |
| 103 | Methyl nonyl acetaldehyde | 110-41-8 | BDFHJK |
| 104 | Methyl myristate | 124-10-7 | DEFHJK |
| 105 | Methyl linoleate | 112-63-0 | DEFHJ |
| 106 | Methyl lavender ketone | 67633-95-8 | CFHJK |
| 108 | Methyl isoeugenol | 93-16-3 | ACEFHK |
| 109 | Methyl hexadecanoate | 112-39-0 | DEFHJK |
| 110 | Methyl eugenol | 93-15-2 | ACEFHK |
| 112 | Methyl epijasmonate | 1211-29-6 | CHJK |
| 113 | Methyl dihydrojasmonate | 24851-98-7 | DFHJK |
| 114 | Methyl diphenyl ether | 3586-14-9 | DEFHJK |
| 117 | Methyl cinnamate | 103-26-4 | BCEFHK |
| 119 | Methyl chavicol | 140-67-0 | ADEFHK |
| 120 | Methyl beta-naphthyl ketone | 93-08-3 | CEFHK |
| 122 | Methyl 2-octynoate | 111-12-6 | ACEFHKL |
| 123 | Methyl alpha-cyclogeranate | 28043-10-9 | ACHIJKL |
| 126 | Methoxycitronellal | 3613-30-7 | ACFGIJK |
| 128 | Menthone 1,2-glycerol ketal (racemic) | 67785-70-0 | CEFHJ |
| 130 | Octahydro-1H-4,7-methanoindene-1-carbaldehyde | 30772-79-3 | BCFHIJKL |
| 134 | 3-(3-(tert-butyl)phenyl)-2-methylpropanal | 62518-65-4 | BDHJK |
| 135 | (E)-4-(4,8-dimethylnona-3,7-dien-1-yl)pyridine | 38462-23-6 | DEFHJK |
| 137 | (E)-trideca-3,12-dienenitrile | 134769-33-8 | DEFHJK |
| 140 | 2,2-dimethyl-3-(m-tolyl)propan-1-ol | 103694-68-4 | CEFHIJK |
| 141 | 2,4-dimethyl-4,4a,5,9b-tetrahydroindeno[1,2-d][1,3]dioxine | 27606-09-3 | CEFHJK |
| 142 | Maceal | 67845-30-1 | BDFHJK |
| 143 | 4-(4-hydroxy-4-methylpentyl)cyclohex-3-ene-1-carbaldehyde | 31906-04-4 | CHJ |
| 145 | l-Limonene | 5989-54-8 | ADEFGIJKL |
| 146 | (Z)-3-hexen-1-yl-2-cyclopenten-1-one | 53253-09-1 | BDHK |
| 148 | Linalyl octanoate | 10024-64-3 | DEFHJ |
| 149 | Linalyl isobutyrate | 78-35-3 | BDHJK |
| 152 | Linalyl benzoate | 126-64-7 | DFHJ |
| 153 | Linalyl anthranilate | 7149-26-0 | DFHJ |

TABLE 1-continued

List of materials with at least one MORV from 1 to 5

| Number | Material Name | CAS Number | Comment Code |
|---|---|---|---|
| 155 | Linalool oxide (furanoid) | 60047-17-8 | BCHIJK |
| 156 | linalool oxide | 1365-19-1 | CGIJK |
| 158 | (2Z,6E)-3,7-dimethylnona-2,6-dienenitrile | 61792-11-8 | BDEFHJK |
| 159 | 3-(4-methylcyclohex-3-en-1-yl)butanal | 6784-13-0 | ACFHIJK |
| 161 | (2,5-dimethyl-1,3-dihydroinden-2-yl)methanol | 285977-85-7 | CEFHJK |
| 162 | 3-(4-(tert-butyl)phenyl)-2-methylpropanal | 80-54-6 | BDHJK |
| 167 | (E)-1-(1-methoxypropoxy)hex-3-ene | 97358-54-8 | ACEFGJKL |
| 168 | Leaf acetal | 88683-94-7 | ACEFGJKL |
| 170 | 1-Carveol | 2102-58-1 | BCHIJK |
| 174 | Lauryl alcohol | 112-53-8 | DEFGJK |
| 175 | Lauryl acetate | 112-66-3 | DEFHJK |
| 176 | Lauric acid | 143-07-7 | DEFHJ |
| 177 | Lactojasmone | 7011-83-8 | BDEFHIJKL |
| 178 | Lauraldehyde | 112-54-9 | BDFHJK |
| 179 | 3,6-dimethylhexahydrobenzofuran-2(3H)-one | 92015-65-1 | BCEFHIJKL |
| 182 | 4-(1-ethoxyvinyl)-3,3,5,5-tetramethylcyclohexan-1-one | 36306-87-3 | BDFHIJK |
| 183 | Khusimol | 16223-63-5 | CEFHJK |
| 184 | 5-(sec-butyl)-2-(2,4-dimethylcyclohex-3-en-1-yl)-5-methyl-1,3-dioxane | 117933-89-8 | DEFHJ |
| 185 | (1-methyl-2-((1,2,2-trimethylbicyclo[3.1.0]hexan-3-yl)methyl)cyclopropyl)methanol | 198404-98-7 | DEFHJK |
| 186 | 2-propylheptanenitrile | 208041-98-9 | ADEFHIJKL |
| 187 | (E)-6-(pent-3-en-1-yl)tetrahydro-2H-pyran-2-one | 32764-98-0 | BCFHIKL |
| 189 | 2-hexylcyclopentan-1-one | 13074-65-2 | BDFHJKL |
| 190 | 2-methyl-4-phenyl-1,3-dioxolane | 33941-99-0 | BCEFGIK |
| 192 | 2,6,9,10-tetramethyl-1-oxaspiro(4.5)deca-3,6-diene | 71078-31-4 | BDEFHIJK |
| 193 | Isopulegol | 89-79-2 | BCEFHIJKL |
| 195 | Isopropyl palmitate | 142-91-6 | DEFHJ |
| 196 | Isopropyl myristate | 110-27-0 | DEFHJK |
| 197 | Isopropyl dodecanoate | 10233-13-3 | DEFHJK |
| 199 | Isopimpinellin | 482-27-9 | CFGJ |
| 206 | Iso3-methylcyclopentadecan-1-one | 3100-36-5 | DEFGJK |
| 208 | Isomenthone | 491-07-6 | ADEFGIJKL |
| 209 | Isojasmone | 95-41-0 | BDFHJKL |
| 210 | Isomenthone | 36977-92-1 | ADEFGIJKL |
| 211 | Isohexenyl cyclohexenyl carboxaldehyde | 37677-14-8 | DFHJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 218 | Isocyclocitral | 1335-66-6 | ACFHIJKL |
| 221 | Isobutyl quinoline | 65442-31-1 | DEFHJK |
| 227 | Isobornylcyclohexanol | 68877-29-2 | DEFHJK |
| 228 | Isobornyl propionate | 2756-56-1 | BDEFHIJK |
| 229 | Isobornyl isobutyrate | 85586-67-0 | BDEFHIJK |
| 230 | Isobornyl cyclohexanol | 66072-32-0 | DEFHJK |
| 231 | Isobornyl acetate | 125-12-2 | ADEFHIJKL |
| 233 | Isobergamate | 68683-20-5 | DEFHJK |
| 234 | Isoamyl undecylenate | 12262-03-2 | DEFHJK |
| 238 | Isoamyl laurate | 6309-51-9 | DEFHJK |
| 242 | Isoambrettolide | 28645-51-4 | DGJ |
| 243 | Irisnitrile | 29127-83-1 | ADEFHKL |
| 244 | Indolene | 68527-79-7 | DEFHJ |
| 246 | Indol/Hydroxycitronellal Schiff base | 67801-36-9 | DEFHJ |
| 247 | 4,4a,5,9b-tetrahydroindeno[1,2-d][1,3]dioxine | 18096-62-3 | BCEFGJK |
| 249 | Hydroxy-citronellol | 107-74-4 | CEFGIJK |
| 252 | 2-cyclododecylpropan-1-ol | 118562-73-5 | DEFHJK |
| 253 | Hydrocitronitrile | 54089-83-7 | CEFHJK |
| 254 | Hydrocinnamyl alcohol | 122-97-4 | BCEFHIK |
| 256 | Hydratropaldehyde dimethyl acetal | 90-87-9 | ACEFHJK |
| 259 | 5-ethyl-4-hydroxy-2-methylfuran-3(2H)-one | 27538-09-6 | CFGIK |

TABLE 1-continued

List of materials with at least one MORV from 1 to 5

| Number | Material Name | CAS Number | Comment Code |
|---|---|---|---|
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 263 | Hexyl octanoate | 1117-55-1 | DEFHJK |
| 267 | Hexyl hexanoate | 6378-65-0 | DEFHJKL |
| 269 | Hexyl cinnamic aldehyde | 101-86-0 | DHJ |
| 271 | Hexyl benzoate | 6789-88-4 | DEFHJK |
| 274 | Hexenyl tiglate | 84060-80-0 | BDEFHJK |
| 276 | (E)-3,7-dimethylocta-2,6-dien-1-yl palmitate | 3681-73-0 | DEFHJ |
| 277 | Hexadecanolide | 109-29-5 | DEFGJK |
| 278 | 2-butyl-4,4,6-trimethyl-1,3-dioxane | 54546-26-8 | ADEFHIJKL |
| 280 | Ethyl (1R,2R,3R,4R)-3-isopropylbicyclo[2.2.1]hept-5-ene-2-carboxylate | 116126-82-0 | BDEFHIJK |
| 281 | 3a,4,5,6,7,7a-hexahydro-1H-4,7-methanoinden-6-yl acetate | 5413-60-5 | CEFGJK |
| 285 | 2-(1-(3,3-dimethylcyclohexyl)ethoxy)-2-methylpropyl propionate | 141773-73-1 | DEFHJ |
| 286 | Heliotropine diethyl acetal | 40527-42-2 | CEFGJ |
| 288 | Helional | 1205-17-0 | CHJK |
| 289 | (E)-oxacyclohexadec-13-en-2-one | 111879-80-2 | DGJK |
| 290 | Gyrane | 24237-00-1 | ADEFHIJKL |
| 292 | Guaiol | 489-86-1 | DEFHJK |
| 293 | 1-(2,6,6-trimethylcyclohex-2-en-1-yl)pentan-3-one | 68611-23-4 | DHJK |
| 294 | Ethyl 2-ethyl-6,6-dimethylcyclohex-2-ene-1-carboxylate | 57934-97-1 | BDEFHIJK |
| 295 | Germacrene B | 15423-57-1 | DEFHJK |
| 296 | Germacrene D | 23986-74-5 | DEFHJK |
| 300 | Geranyl phenylacetate | 102-22-7 | DFHJ |
| 301 | Geranyl phenyl acetate | 71648-43-6 | DFHJ |
| 303 | Geranyl linalool | 1113-21-9 | DFHJ |
| 307 | Geranyl cyclopentanone | 68133-79-9 | DHJK |
| 316 | gamma-Undecalactone (racemic) | 104-67-6 | DEFHJKL |
| 317 | gamma-Terpinyl acetate | 10235-63-9 | BDHJK |
| 318 | gamma-Terpineol | 586-81-2 | BCGIJK |
| 321 | gamma-Nonalactone | 104-61-0 | BCEFHIKL |
| 322 | gamma-Muurolene | 30021-74-0 | DEFHJKL |
| 323 | gamma-(E)-6-(pent-3-en-1-yl)tetrahydro-2H-pyran-2-one | 63095-33-0 | BCEFHKL |
| 324 | gamma-Ionone | 79-76-5 | BDEFHIJK |
| 325 | gamma-Himachalene | 53111-25-4 | BDEFHJKL |
| 328 | gamma-Gurjunene | 22567-17-5 | DEFHJKL |
| 329 | gamma-Eudesmol | 1209-71-8 | DFHJK |
| 330 | gamma-Dodecalactone | 2305-05-7 | DEFHJK |
| 331 | gamma-Damascone | 35087-49-1 | BDEFHIJK |
| 332 | gamma-Decalactone | 706-14-9 | BDEFHIJKL |
| 333 | gamma-Cadinene | 39029-41-9 | DEFHJKL |
| 334 | 1-(3,3-dimethylcyclohexyl)pent-4-en-1-one | 56973-87-6 | BDEFHJK |
| 335 | 4,6,6,7,8,8-hexamethyl-1,3,4,6,7,8-hexahydrocyclopenta[g]isochromene | 1222-05-5 | DEFHJK |
| 336 | Furfuryl octanoate | 39252-03-4 | DEFHJK |
| 338 | Furfuryl hexanoate | 39252-02-3 | CEFHJK |
| 339 | Furfuryl heptanoate | 39481-28-2 | CEFHJK |
| 342 | 2-methyldecanenitrile | 69300-15-8 | BDEFHJKL |
| 343 | 8,8-dimethyl-3a,4,5,6,7,7a-hexahydro-1H-4,7-methanoinden-6-yl propionate | 76842-49-4 | DEFHJK |
| 344 | Ethyl (3aR,4S,7R,7aR)-octahydro-3aH-4,7-methanoindene-3a-carboxylate | 80657-64-3 | DEFHIJK |
| 347 | Diethyl cyclohexane-1,4-dicarboxylate | 72903-27-6 | CEFHJK |
| 349 | (6-isopropyl-9-methyl-1,4-dioxaspiro[4.5]decan-2-yl)methanol | 63187-91-7 | CEFHJ |
| 350 | 2-isobutyl-4-methyltetrahydro-2H-pyran-4-ol | 63500-71-0 | BCEFHIJK |
| 352 | Undec-10-enenitrile | 53179-04-7 | BDEFHJK |
| 353 | (Z)-6-ethylideneoctahydro-2H-5,8-methanochromen-2-one | 69486-14-2 | CEFGJK |

TABLE 1-continued

List of materials with at least one MORV from 1 to 5

| Number | Material Name | CAS Number | Comment Code |
|---|---|---|---|
| 356 | 3-(2-ethylphenyl)-2,2-dimethylpropanal | 67634-15-5 | BDHJK |
| 358 | (E)-4,8-dimethyldeca-4,9-dienal | 71077-31-1 | BDFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 360 | 8,8-dimethyl-3a,4,5,6,7,7a-hexahydro-1H-4,7-methanoinden-6-yl acetate | 171102-41-3 | DEFHJK |
| 361 | 3-(4-ethylphenyl)-2,2-dimethylpropanenitrile | 134123-93-6 | DEFHJK |
| 362 | 2-heptylcyclopentan-1-one | 137-03-1 | DFHJKL |
| 363 | 1-ethoxyethoxy Cyclododecane | 389083-83-4 | DEFHJK |
| 364 | 3-cyclohexene-1-carboxylic acid, 2,6,6-trimethyl-, methyl ester | 815580-59-7 | ACHIJKL |
| 368 | Farnesyl acetate | 29548-30-9 | DEFHJK |
| 369 | Farnesol | 4602-84-0 | DEFHJK |
| 370 | Oxacyclohexadecan-2-one | 106-02-5 | DEFGJK |
| 371 | 1-cyclopentadec-4-en-1-one | 14595-54-1 | DEFGJK |
| 372 | 1-cyclopentadec-4-en-1-one | 35720-57-1 | DEFGJK |
| 373 | 2-methoxy-4-(4-methylenetetrahydro-2H-pyran-2-yl)phenol | 128489-04-3 | CGJ |
| 374 | Eugenyl acetate | 93-28-7 | CFHJK |
| 375 | Eugenol | 97-53-0 | CHIK |
| 377 | Ethylmethylphenylglycidate | 77-83-8 | CFHJK |
| 378 | Ethylene brassylate | 105-95-3 | DFGJ |
| 381 | Ethyl undecylenate | 692-86-4 | DEFHJK |
| 385 | Ethyl palmitate | 628-97-7 | DEFHJ |
| 386 | Ethyl nonanoate | 123-29-5 | BDEFHJKL |
| 388 | Ethyl myristate | 124-06-1 | DEFHJK |
| 390 | Ethyl linalool | 10339-55-6 | BCEFHJK |
| 391 | Ethyl laurate | 106-33-2 | DEFHJK |
| 394 | Ethyl hexyl ketone | 925-78-0 | ADFHIKL |
| 397 | Ethyl decanoate | 110-38-3 | BDEFHJK |
| 398 | Ethyl gamma-Safranate | 35044-57-6 | ADHIJK |
| 407 | Ethyl 3-phenylglycidate | 121-39-1 | CGJK |
| 413 | 6-ethyl-2,10,10-trimethyl-1-oxaspiro[4.5]deca-3,6-diene | 79893-63-3 | BDEFHIJK |
| 414 | Elemol | 639-99-6 | DEFHJK |
| 415 | (2-(1-ethoxyethoxy)ethyl)benzene | 2556-10-7 | BCEFHJK |
| 416 | (E)-3-methyl-5-(2,2,3-trimethylcyclopent-3-en-1-yl)pent-4-en-2-ol | 67801-20-1 | DHJK |
| 417 | d-xylose | 58-86-6 | CGIJ |
| 418 | (E)-4-((3aS,7aS)-octahydro-5H-4,7-methanoinden-5-ylidene)butanal | 30168-23-1 | DFHJK |
| 421 | Dodecanal dimethyl acetal | 14620-52-1 | DEFHJK |
| 424 | d-Limonene | 5989-27-5 | ADEFGIJKL |
| 425 | Dipropylene Glycol | 25265-71-8 | CEFGIK |
| 426 | Dispirone | 83863-64-3 | BDEFHJK |
| 428 | Diphenyloxide | 101-84-8 | BDEFHK |
| 429 | Diphenylmethane | 101-81-5 | DEFGK |
| 432 | Dimethyl benzyl carbinyl butyrate | 10094-34-5 | DEFHJK |
| 436 | 2,6-dimethyloct-7-en-4-one | 1879-00-1 | ADEFHIJKL |
| 441 | Octahydro-1H-4,7-methanoinden-5-yl acetate | 64001-15-6 | DEFHJKL |
| 444 | Dihydrocarveol acetate | 20777-49-5 | BDEFHIJK |
| 445 | Dihydrocarveol | 619-01-2 | BCEFHIJKL |
| 449 | Dihydro Linalool | 18479-51-1 | BCEFGIJKL |
| 450 | Dihydro Isojasmonate | 37172-53-5 | DHJK |
| 453 | Dibutyl sulfide | 544-40-1 | ADEFHIKL |
| 457 | Dibenzyl | 103-29-7 | DEFGJK |
| 459 | delta-Undecalactone | 710-04-3 | DEFHJKL |
| 461 | delta-Elemene | 20307-84-0 | BDEFHJK |
| 462 | delta-Guaiene | 3691-11-0 | DEFHJKL |
| 463 | delta-Dodecalactone | 713-95-1 | DEFHJK |
| 464 | delta-Decalactone | 705-86-2 | BDEFHIJKL |
| 465 | delta-Cadinene | 483-76-1 | DEFHJKL |
| 466 | delta-damascone | 57378-68-4 | ADHIJK |
| 467 | delta-Amorphene | 189165-79-5 | DEFHJKL |
| 468 | delta-3-Carene | 13466-78-9 | ADEFGIJKL |
| 470 | Decylenic alcohol | 13019-22-2 | BDEFHJK |
| 471 | Decyl propionate | 5454-19-3 | DEFHJK |

TABLE 1-continued

List of materials with at least one MORV from 1 to 5

| Number | Material Name | CAS Number | Comment Code |
|---|---|---|---|
| 473 | Decanal diethyl acetal | 34764-02-8 | DEFHJK |
| 474 | Decahydro-beta-naphthol | 825-51-4 | BCEFGIK |
| 475 | 1-cyclohexylethyl (E)-but-2-enoate | 68039-69-0 | BDFHJK |
| 478 | 3-(4-isopropylphenyl)-2-methylpropanal | 103-95-7 | BDFHJK |
| 479 | Cyclotetradecane | 295-17-0 | DEFGJKL |
| 480 | Cyclopentadecanone | 502-72-7 | DEFGJK |
| 482 | Cyclohexyl salicylate | 25485-88-5 | DFGJ |
| 484 | 3a,4,5,6,7,7a-hexahydro-1H-4,7-methanoinden-6-yl butyrate | 113889-23-9 | DEFHJK |
| 485 | Cyclic ethylene dodecanedioate | 54982-83-1 | DFGJ |
| 486 | 8,8-dimethyl-1,2,3,4,5,6,7,8-octahydronaphthalene-2-carbaldehyde | 68991-97-9 | DHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 491 | Cumic alcohol | 536-60-7 | CHIJK |
| 493 | Coumarone | 1646-26-0 | BCEFHIK |
| 497 | 2-(3-phenylpropyl)pyridine | 2110-18-1 | CEFHJK |
| 498 | Dodecanenitrile | 2437-25-4 | DEFHJK |
| 501 | (E)-cycloheptadec-9-en-1-one | 542-46-1 | DEFGJ |
| 502 | Citryl acetate | 6819-19-8 | DFHJK |
| 503 | Citrus Propanol | 15760-18-6 | CEFHIJK |
| 505 | Citronitrile | 93893-89-1 | CEFHJK |
| 519 | Citral propylene glycol acetal | 10444-50-5 | CEFHJK |
| 520 | Citral dimethyl acetal | 7549-37-3 | BCEFHJK |
| 521 | Citral diethyl acetal | 7492-66-2 | BDEFHJK |
| 524 | cis-Ocimene | 3338-55-4 | ADGIKL |
| 527 | cis-Limonene oxide | 13837-75-7 | ADEFGIJKL |
| 529 | Cis-iso-ambrettolide | 36508-31-3 | DGJ |
| 530 | cis-6-nonenol | 35854-86-5 | BCEFHIKL |
| 531 | cis-carveol | 1197-06-4 | BCHIJK |
| 532 | cis-4-Decen-1-al | 21662-09-9 | ADHKL |
| 534 | cis-3-hexenyl-cis-3-hexenoate | 61444-38-0 | BDEFHJK |
| 537 | cis-3-Hexenyl salicylate | 65405-77-8 | DEFGJ |
| 541 | Cis-3-hexenyl Benzoate | 25152-85-6 | DEFHJK |
| 544 | cis-3-Hexenyl 2-methylbutyrate | 53398-85-9 | ADEFHJKL |
| 546 | cis-3, cis-6-nonadienol | 53046-97-2 | ACEFHK |
| 548 | Cinnamyl propionate | 103-56-0 | DEFHJK |
| 550 | Cinnamyl isobutyrate | 103-59-3 | DEFHJK |
| 551 | Cinnamyl formate | 104-65-4 | BCEFHK |
| 552 | Cinnamyl cinnamate | 122-69-0 | DHJ |
| 553 | Cinnamyl acetate | 103-54-8 | BCEFHK |
| 555 | Cinnamic alcohol | 104-54-1 | BCEFHIK |
| 558 | Cetyl alcohol | 36653-82-4 | DEFHJ |
| 559 | (E)-1-(2,6,6-trimethylcyclohex-2-en-1-yl)hepta-1,6-dien-3-one | 79-78-7 | DHJK |
| 560 | 2-methyl-4-(2,6,6-trimethylcyclohex-1-en-1-yl)butanal | 65405-84-7 | DFHJK |
| 561 | (3aR,5aR,9aR,9bR)-3a,6,6,9a-tetramethyldodecahydronaphtho[2,1-b]furan | 3738-00-9 | DEFHJK |
| 562 | 1,6-dioxacycloheptadecan-7-one | 6707-60-4 | DGJ |
| 563 | 1-(6-(tert-butyl)-1,1-dimethyl-2,3-dihydro-1H-inden-4-yl)ethan-1-one | 13171-00-1 | DEFHJK |
| 565 | Cedryl methyl ether | 19870-74-7 | ADEFHJK |
| 566 | Cedryl formate | 39900-38-4 | BDEFHJK |
| 567 | Cedryl acetate | 77-54-3 | DEFHJK |
| 568 | (4Z,8Z)-1,5,9-trimethyl-13-oxabicyclo[10.1.0]trideca-4,8-diene | 71735-79-0 | DFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 571 | 5-methyl-1-(2,2,3-trimethylcyclopent-3-en-1-yl)-6-oxabicyclo[3.2.1]octane | 426218-78-2 | DFHJ |
| 572 | 1,1,2,3,3-pentamethyl-1,2,3,5,6,7-hexahydro-4H-inden-4-one | 33704-61-9 | BDEFHIJK |
| 573 | Caryophyllene alcohol acetate | 32214-91-8 | DEFHJK |
| 574 | Caryolan-1-ol | 472-97-9 | DEFHJK |
| 577 | Carvyl acetate | 97-42-7 | BDHIJK |
| 578 | Caprylnitrile | 124-12-9 | ACEFGIKL |
| 580 | Caprylic alcohol | 111-87-5 | ACEFGIKL |

TABLE 1-continued

List of materials with at least one MORV from 1 to 5

| Number | Material Name | CAS Number | Comment Code |
|---|---|---|---|
| 581 | Caprylic acid | 124-07-2 | BCEFHIK |
| 582 | Capric acid | 334-48-5 | DEFHJK |
| 584 | Capraldehyde | 112-31-2 | ADHKL |
| 586 | 3-(4-methoxyphenyl)-2-methylpropanal | 5462-06-6 | BCHJK |
| 587 | Camphorquinone | 10373-78-1 | ACEFGIJK |
| 589 | Camphene | 79-92-5 | ADEFGIJKL |
| 591 | Ethyl 2-methyl-4-oxo-6-pentylcyclohex-2-ene-1-carboxylate | 59151-19-8 | DHJ |
| 592 | Butylated hydroxytoluene | 128-37-0 | DEFGIJK |
| 594 | Butyl stearate | 123-95-5 | DEFHJ |
| 595 | Butyl butyryl lactate | 7492-70-8 | CEFGJK |
| 599 | Butyl 10-undecenoate | 109-42-2 | DEFHJK |
| 600 | 2-methyl-4-(2,2,3-trimethylcyclopent-3-en-1-yl)butan-1-ol | 72089-08-8 | DEFHJK |
| 601 | 3-(4-(tert-butyl)phenyl)propanal | 18127-01-0 | BDHJK |
| 603 | Bornyl isobutyrate | 24717-86-0 | BDEFHIJK |
| 604 | Bornyl acetate | 76-49-3 | ADEFHIJKL |
| 606 | 2-ethoxy-2,6,6-trimethyl-9-methylenebicyclo[3.3.1]nonane | 68845-00-1 | BDEFHJK |
| 607 | (ethoxymethoxy)cyclododecane | 58567-11-6 | DEFHJK |
| 608 | Bisabolene | 495-62-5 | DEFHJK |
| 609 | Bigarade oxide | 72429-08-4 | ADEFHJKL |
| 610 | beta-Vetivone | 18444-79-6 | DHJK |
| 611 | beta-Terpinyl acetate | 10198-23-9 | BDHJK |
| 612 | beta-Terpineol | 138-87-4 | BCGIJK |
| 613 | beta-Sinensal | 60066-88-8 | DHJK |
| 614 | beta-Sesquiphellandrene | 20307-83-9 | DEFHJK |
| 615 | beta-Selinene | 17066-67-0 | BDEFGJK |
| 616 | beta-Santalol | 77-42-9 | DEFHJK |
| 618 | beta-Pinene | 127-91-3 | ADEFGIJKL |
| 620 | beta-Naphthyl ethyl ether | 93-18-5 | BDEFHJK |
| 621 | beta-Patchoulline | 514-51-2 | BDEFGJKL |
| 624 | beta-Himachalene Oxide | 57819-73-5 | BDFHJK |
| 625 | beta-Himachalene | 1461-03-6 | DEFHJKL |
| 626 | beta-Guaiene | 88-84-6 | DEFHJKL |
| 627 | (2,2-dimethoxyethyl)benzene | 101-48-4 | DHJK |
| 628 | beta-Farnesene | 18794-84-8 | DEFHJK |
| 631 | beta-Copaene | 18252-44-3 | BDEFHJKL |
| 632 | beta-Cedrene | 546-28-1 | BDEFGJKL |
| 633 | beta-Caryophyllene | 87-44-5 | DEFHJKL |
| 635 | beta-Bisabolol | 15352-77-9 | DFHJK |
| 636 | Beta ionone epoxide | 23267-57-4 | BDEFHIJK |
| 638 | Bergaptene | 484-20-8 | CGJ |
| 639 | Benzyl-tert-butanol | 103-05-9 | CEFGJK |
| 644 | Benzyl laurate | 140-25-0 | DEFHJ |
| 649 | Benzyl dimethyl carbinol | 100-86-7 | BCEFGIK |
| 650 | Benzyl cinnamate | 103-41-3 | DHJ |
| 653 | Benzyl benzoate | 120-51-4 | DHJ |
| 655 | Benzophenone | 119-61-9 | DEFHK |
| 658 | 7-isopentyl-2H-benzo[b][1,4]dioxepin-3(4H)-one | 362467-67-2 | DHJ |
| 659 | 2'-isopropyl-1,7,7-trimethylspiro[bicyclo[2.2.1]heptane-2,4'-[1,3]dioxane] | 188199-50-0 | DEFHJK |
| 660 | 4-(4-methylpent-3-en-1-yl)cyclohex-3-ene-1-carbonitrile | 21690-43-7 | DEFHJK |
| 661 | Aurantiol | 89-43-0 | DEFHJ |
| 663 | Anisyl phenylacetate | 102-17-0 | DFHJ |
| 668 | Methyl (E)-octa-4,7-dienoate | 189440-77-5 | ACEFHKL |
| 671 | Amyl Cinnamate | 3487-99-8 | DEFHJK |
| 673 | (3aR,5aS,9aS,9bR)-3a,6,6,9a-tetramethyldodecahydronaphtho[2,1-b]furan | 6790-58-5 | DEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 675 | 2,5,5-trimethyl-1,2,3,4,5,6,7,8-octahydronaphthalen-2-ol | 71832-76-3 | DEFHJK |
| 676 | 2,5,5-trimethyl-1,2,3,4,5,6,7,8-octahydronaphthalen-2-ol | 41199-19-3 | DEFHJK |
| 677 | 1-((2-(tert-butyl)cyclohexyl)oxy)butan-2-ol | 139504-68-0 | DEFHJK |

TABLE 1-continued

List of materials with at least one MORV from 1 to 5

| Number | Material Name | CAS Number | Comment Code |
|---|---|---|---|
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | ADEFHJK |
| 680 | 2,2,6,6,7,8,8-heptamethyldecahydro-2H-indeno[4,5-b]furan | 647828-16-8 | ADEFHJK |
| 681 | Amber acetate | 37172-02-4 | BDEFHJK |
| 682 | Alpinofix ® | 811436-82-5 | DEFHJ |
| 683 | alpha-Thujone | 546-80-5 | ADEFGIJKL |
| 684 | alpha-Vetivone | 15764-04-2 | DHJK |
| 686 | alpha-Terpinyl propionate | 80-27-3 | BDEFHJK |
| 691 | alpha-Sinensal | 17909-77-2 | DHJK |
| 692 | alpha-Selinene | 473-13-2 | BDEFHJK |
| 693 | alpha-Santalene | 512-61-8 | ADEFHJKL |
| 694 | alpha-Santalol | 115-71-9 | DEFHJK |
| 696 | alpha-Patchoulene | 560-32-7 | ADEFHJKL |
| 697 | alpha-neobutenone | 56973-85-4 | BDHJK |
| 698 | alpha-Muurolene | 10208-80-7 | DEFHJKL |
| 700 | alpha-methyl ionone | 127-42-4 | BDHJK |
| 702 | alpha-Limonene | 138-86-3 | ADEFGIJKL |
| 704 | alpha-Irone | 79-69-6 | BDHJK |
| 706 | alpha-Humulene | 6753-98-6 | DEFHJK |
| 707 | alpha-Himachalene | 186538-22-7 | BDEFHJK |
| 708 | alpha-Gurjunene | 489-40-7 | BDEFHJKL |
| 709 | alpha-Guaiene | 3691-12-1 | DEFHJKL |
| 710 | alpha-Farnesene | 502-61-4 | DEFHJK |
| 711 | alpha-Fenchene | 471-84-1 | ADEFGIJKL |
| 712 | alpha-Eudesmol | 473-16-5 | DEFHJK |
| 713 | alpha-Curcumene | 4176-17-4 | DEFHJK |
| 714 | alpha-Cubebene | 17699-14-8 | ADEFHJKL |
| 715 | alpha-Cedrene epoxide | 13567-39-0 | ADEFHJK |
| 716 | alpha-Cadinol | 481-34-5 | DEFHJK |
| 717 | alpha-Cadinene | 24406-05-1 | DEFHJKL |
| 718 | alpha-Bisabolol | 515-69-5 | DFHJK |
| 719 | alpha-bisabolene | 17627-44-0 | DEFHJK |
| 720 | alpha-Bergamotene | 17699-05-7 | BDEFHJKL |
| 721 | alpha-Amylcinnamyl alcohol | 101-85-9 | DEFHJ |
| 722 | alpha-Amylcinnamyl acetate | 7493-78-9 | DEFHJ |
| 723 | alpha-Amylcinnamaldehyde diethyl acetal | 60763-41-9 | DEFHJ |
| 724 | alpha-Amylcinnamaldehyde | 122-40-7 | DHJK |
| 725 | alpha-Amorphene | 23515-88-0 | DEFHJKL |
| 726 | alpha-Agarofuran | 5956-12-7 | BDEFHJK |
| 727 | 1-methyl-4-(4-methyl-3-penten-1-yl)-3-Cyclohexene-1-carboxaldehyde | 52475-86-2 | DFHJK |
| 730 | 1-Phenyl-2-pentanol | 705-73-7 | CEFHK |
| 731 | 1-Phenyl-3-methyl-3-pentanol | 10415-87-9 | CEFHJK |
| 733 | 2,3,4-trimethoxy-benzaldehyde | 2103-57-3 | BCGI |
| 735 | 2,4,5-trimethoxy-benzaldehyde | 4460-86-0 | BCG |
| 736 | 2,4,6-trimethoxybenzaldehyde | 830-79-5 | BCGI |
| 738 | 2,4-Nonadienal | 6750-03-4 | ACHKL |
| 741 | 2,6,10-Trimethylundecanal | 105-88-4 | BDFGJK |
| 742 | alpha,4-Dimethyl benzenepropanal | 41496-43-9 | ACHJK |
| 746 | Allyl cyclohexyl propionate | 2705-87-5 | BDEFHJK |
| 748 | Allyl amyl glycolate | 67634-00-8 | BCEFGJK |
| 750 | Allo-aromadendrene | 25246-27-9 | BDEFHJKL |
| 752 | Aldehyde C-11 | 143-14-6 | ADHJK |
| 754 | Methyl (E)-2-(((3,5-dimethylcyclohex-3-en-1-yl)methylene)amino)benzoate | 94022-83-0 | DEFHJ |
| 757 | 2,6,10-trimethylundec-9-enal | 141-13-9 | BDFHJK |
| 758 | Acetoxymethyl-isolongifolene (isomers) | 59056-62-1 | BDEFHJK |
| 763 | Acetate C9 | 143-13-5 | BDEFHJKL |
| 764 | Acetarolle | 744266-61-3 | DFHJK |
| 766 | Acetaldehyde phenylethyl propyl acetal | 7493-57-4 | CEFHJK |
| 767 | Acetaldehyde dipropyl acetal | 105-82-8 | ACEFGIKL |
| 768 | Acetaldehyde benzyl 2-methoxyethyl acetal | 7492-39-9 | BCEFHJK |
| 769 | (Z)-2-(4-methylbenzylidene)heptanal | 84697-09-6 | DHJ |
| 770 | 9-decenal | 39770-05-3 | ADHKL |
| 771 | 8-Hexadecenolide | 123-69-3 | DGJ |
| 772 | 7-Methoxycoumarin | 531-59-9 | CHK |

TABLE 1-continued

List of materials with at least one MORV from 1 to 5

| Number | Material Name | CAS Number | Comment Code |
|---|---|---|---|
| 774 | 7-epi-alpha-Selinene | 123123-37-5 | BDEFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 778 | 6-Isopropylquinoline | 135-79-5 | CEFHJK |
| 781 | 6,6-dimethyl-2-norpinene-2-propionaldehyde | 33885-51-7 | BCFHJK |
| 782 | 6,10,14-trimethyl-2-Pentadecanone | 502-69-2 | DEFHJK |
| 786 | 5-Isopropenyl-2-methyl-2-vinyltetrahydrofuran | 13679-86-2 | ACGIJKL |
| 788 | 5-Cyclohexadecenone | 37609-25-9 | DEFGJK |
| 791 | 4-Terpinenol | 562-74-3 | BCHIJK |
| 792 | 4-Pentenophenone | 3240-29-7 | BCEFHIK |
| 800 | 4-Carvomenthenol | 28219-82-1 | BCHIJK |
| 802 | 4,5,6,7-Tetrahydro-3,6-dimethylbenzofuran | 494-90-6 | BCEFHIJKL |
| 803 | 4-(p-Methoxyphenyl)-2-butanone | 104-20-1 | BCEFHJK |
| 804 | 3-Thujopsanone | 25966-79-4 | BDEFHJK |
| 805 | 3-Propylidenephthalide | 17369-59-4 | CEFHK |
| 806 | 3-Nonylacrolein | 20407-84-5 | BDFHJK |
| 807 | 3-Methyl-5-phenyl-1-pentanal | 55066-49-4 | BDFHJK |
| 814 | 3-Hexenyl isovalerate | 10032-11-8 | ADEFHJKL |
| 821 | 3,6-Dimethyl-3-octanyl acetate | 60763-42-0 | ADEFHIJKL |
| 824 | 3,4,5-trimethoxybenzaldehyde | 86-81-7 | BCGIK |
| 826 | 3-(p-Isopropylphenyl)propionaldehyde | 7775-00-0 | BDFHJK |
| 827 | 2-Undecenenitrile | 22629-48-7 | BDEFHJK |
| 828 | 2-Undecenal | 2463-77-6 | ADHJK |
| 829 | 2-trans-6-trans-Nonadienal | 17587-33-6 | ACHKL |
| 831 | 2-Phenylethyl butyrate | 103-52-6 | DEFHJK |
| 833 | 2-Phenyl-3-(2-furyl)prop-2-enal | 57568-60-2 | CHJ |
| 834 | 2-Phenoxyethanol | 122-99-6 | BCEFGIK |
| 837 | 2-Nonen-1-al | 2463-53-8 | ADHKL |
| 839 | 2-Nonanol | 628-99-9 | BDEFGIKL |
| 840 | 2-Nonanone | 821-55-6 | ADFHIKL |
| 849 | 2-Isobutyl quinoline | 93-19-6 | CEFHJK |
| 850 | 2-Hexylidene cyclopentanone | 17373-89-6 | DFHJKL |
| 852 | 2-Heptyl tetrahydrofuran | 2435-16-7 | BDEFHJKL |
| 856 | 2-Decenal | 3913-71-1 | ADHKL |
| 864 | 2,6-Nonadienal | 26370-28-5 | ACHKL |
| 865 | 2,6-Nonadien-1-ol | 7786-44-9 | ACEFHK |
| 866 | 2,6-dimethyl-octanal | 7779-07-9 | ADFGIJKL |
| 868 | 1-Decanol | 112-30-1 | BDEFGJK |
| 869 | 1-Hepten-1-ol, 1-acetate | 35468-97-4 | ACEFHKL |
| 870 | 10-Undecen-1-ol | 112-43-6 | DEFHJK |
| 871 | 10-Undecenal | 112-45-8 | ADHJK |
| 872 | 10-epi-gamma-Eudesmol | 15051-81-7 | DFHJK |
| 873 | 1,8-Thiocineol | 68391-28-6 | ADEFHIJKL |
| 876 | 1,3,5-undecatriene | 16356-11-9 | ADEFHJKL |
| 877 | 1,2-Dihydrolinalool | 2270-57-7 | BCEFGIJKL |
| 878 | 1,3,3-trimethyl-2-norbornanyl acetate | 13851-11-1 | ADEFHIJKL |
| 879 | 1,1,2,3,3-Pentamethylindan | 1203-17-4 | ADHIJKL |
| 881 | (Z)-6,10-dimethylundeca-5,9-dien-2-yl acetate | 3239-37-0 | DEFHJK |
| 884 | (Z)-3-Dodecenal | 68141-15-1 | BCFHJK |
| 885 | (S)-gamma-Undecalactone | 74568-05-1 | DEFHJKL |
| 886 | (R)-gamma-Undecalactone | 74568-06-2 | DEFHJKL |
| 890 | (E)-6,10-dimethylundeca-5,9-dien-2-yl acetate | 3239-35-8 | DEFHJK |
| 892 | (2Z)-3-methyl-5-phenyl-2-Pentenenitrile | 53243-59-7 | DEFHJK |
| 893 | (2S,5S,6S)-2,6,10,10-tetramethyl-1-oxaspiro[4_5]decan-6-ol | 65620-50-0 | DFHIJK |
| 894 | (2E)-3-methyl-5-phenyl-2-pentenenitrile | 53243-60-0 | CEFHJK |
| 897 | (+)-Dihydrocarveol | 22567-21-1 | BCEFHIJKL |
| 905 | Menthone | 89-80-5 | ADEFGIJKL |
| 908 | (R,E)-2-methyl-4-(2,2,3-trimethylcyclopent-3-en-1-yl)but-2-en-1-ol | 185068-69-3 | CHJK |
| 912 | 2-(8-isopropyl-6-methylbicyclo[2.2.2]oct-5-en-2-yl)-1,3-dioxolane | 68901-32-6 | DEFHJK |
| 913 | gamma-methyl ionone | 7388-22-9 | BDHIJK |

TABLE 1-continued

List of materials with at least one MORV from 1 to 5

| Number | Material Name | CAS Number | Comment Code |
|---|---|---|---|
| 914 | 3-(3-isopropylphenyl)butanal | 125109-85-5 | BDHJK |
| 916 | 3-(1-ethoxyethoxy)-3,7-dimethylocta-1,6-diene | 40910-49-4 | BDEFHJK |
| 919 | 3a,4,5,6,7,7a-hexahydro-1H-4,7-methanoinden-6-yl propionate | 17511-60-3 | CEFHJK |
| 920 | Bulnesol | 22451-73-6 | DEFHJK |
| 922 | Benzyl phenylacetate | 102-16-9 | DHJ |
| 923 | Benzoin | 119-53-9 | CEFHJ |
| 924 | (E)-1,2,4-trimethoxy-5-(prop-1-en-1-yl)benzene | 2883-98-9 | BCFGJK |
| 925 | alpha,alpha,6,6-tetramethyl bicyclo[3.1.1]hept-2-ene-propanal | 33885-52-8 | BDFHJK |
| 926 | 7-epi-sesquithujene | 159407-35-9 | DEFHJKL |
| 927 | 5-Acetyl-1,1,2,3,3,6-hexamethylindan | 15323-35-0 | DEFHJK |
| 928 | 3-Methylphenethyl alcohol | 1875-89-4 | BCEFHIK |
| 929 | 3,6-Nonadien-1-ol | 76649-25-7 | ACEFHK |
| 930 | 2-Tridecenal | 7774-82-5 | BDFHJK |
| 933 | Patchouli alcohol | 5986-55-0 | DEFHIJK |
| 937 | p-Cresyl isobutyrate | 103-93-5 | BDHJK |
| 939 | p-Cresyl n-hexanoate | 68141-11-7 | DEFHJK |
| 941 | 5-hexyl-4-methyldihydrofuran-2(3H)-one | 67663-01-8 | BDEFHIJKL |
| 942 | Ethyl (2Z,4E)-deca-2,4-dienoate | 3025-30-7 | BDEFHJK |
| 943 | Pelargene | 68039-40-7 | DEFHJK |
| 945 | 2-cyclohexylidene-2-phenylacetonitrile | 10461-98-0 | DFHJK |
| 946 | Perillaldehyde | 2111-75-3 | ACHIJK |
| 947 | Perillyl acetate | 15111-96-3 | DFHJK |
| 948 | Perillyl alcohol | 536-59-4 | CHIJK |
| 950 | (2-isopropoxyethyl)benzene | 68039-47-4 | ACEFHJKL |
| 951 | Ethyl (2Z,4E)-deca-2,4-dienoate | 313973-37-4 | BDEFHJK |
| 953 | (2-(cyclohexyloxy)ethyl)benzene | 80858-47-5 | DEFHJK |
| 954 | Phenethyl 2-methylbutyrate | 24817-51-4 | DEFHJK |
| 955 | Phenethyl alcohol | 60-12-8 | BCEFGIK |
| 959 | Phenethyl phenylacetate | 102-20-5 | DHJ |
| 962 | Phenoxanol | 55066-48-3 | DEFHJK |
| 965 | Phenyl benzoate | 93-99-2 | DFHJK |
| 967 | Phenyl ethyl benzoate | 94-47-3 | DHJ |
| 969 | Phenylacetaldehyde ethyleneglycol acetal | 101-49-5 | BCEFGIK |
| 973 | 2-(6,6-dimethylbicyclo[3.1.1]hept-2-en-2-yl)acetaldehyde | 30897-75-7 | ACFHIJKL |
| 974 | Pinocarveol | 5947-36-4 | BCEFGIJKL |
| 976 | Piperonyl acetone | 55418-52-5 | CEFGJ |
| 978 | 3a,4,5,6,7,7a-hexahydro-1H-4,7-methanoinden-6-yl pivalate | 68039-44-1 | DEFHJK |
| 980 | (4aR,8aS)-7-methyloctahydro-1,4-methanonaphthalen-6(2H)-one | 41724-19-0 | CEFGJKL |
| 982 | p-Menth-3-en-1-ol | 586-82-3 | BCGIJK |
| 985 | (E)-3,3-dimethyl-5-(2,2,3-trimethylcyclopent-3-en-1-yl)pent-4-en-2-ol | 107898-54-4 | DHJK |
| 988 | 1-methyl-4-(4-methylpent-3-en-1-yl)cyclohex-3-ene-1-carbaldehyde | 52474-60-9 | DFHJK |
| 993 | Propylene glycol | 57-55-6 | ACEFGIKL |
| 998 | p-Tolyl phenylacetate | 101-94-0 | DFHJ |
| 1000 | Ethyl 2,4,7-decatrienoate | 78417-28-4 | BDEFHJK |
| 1003 | 2-benzyl-4,4,6-trimethyl-1,3-dioxane | 67633-94-7 | DEFHJK |
| 1006 | 2,4-dimethyl-4-phenyltetrahydrofuran | 82461-14-1 | BDEFHJK |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1008 | (Z)-6-ethylideneoctahydro-2H-5,8-methanochromene | 93939-86-7 | BCEFHJKL |
| 1009 | 2-((S)-1-((S)-3,3-dimethylcyclohexyl)ethoxy)-2-oxoethyl propionate | 236391-76-7 | DFHJ |
| 1010 | Methyl 2,2-dimethyl-6-methylenecyclohexane-1-carboxylate | 81752-87-6 | ADHIJKL |
| 1012 | 2-methyl-5-phenylpentan-1-ol | 25634-93-9 | DEFHJK |
| 1016 | 4-methyl-2-phenyl-3,6-dihydro-2H-pyran | 60335-71-9 | BCEFGJK |

TABLE 1-continued

List of materials with at least one MORV from 1 to 5

| Number | Material Name | CAS Number | Comment Code |
|---|---|---|---|
| 1020 | Sabinol | 471-16-9 | BCEFHIJKL |
| 1021 | Safrole | 94-59-7 | BCEFHK |
| 1022 | 2,2,7,9-tetramethylspiro(5.5)undec-8-en-1-one | 502847-01-0 | DHIJK |
| 1023 | 3-methyl-5-(2,2,3-trimethylcyclopent-3-en-1-yl)pentan-2-ol | 65113-99-7 | DEFHJK |
| 1024 | (Z)-2-ethyl-4-(2,2,3-trimethylcyclopent-3-en-1-yl)but-2-en-1-ol | 28219-61-6 | DEFHJK |
| 1025 | (E)-2-methyl-4-(2,2,3-trimethylcyclopent-3-en-1-yl)but-2-en-1-ol | 28219-60-5 | CHJK |
| 1026 | 5-methoxyoctahydro-1H-4,7-methanoindene-2-carbaldehyde | 86803-90-9 | CHJK |
| 1027 | 5-methoxyoctahydro-1H-4,7-methanoindene-2-carbaldehyde | 193425-86-4 | CHJK |
| 1028 | Sclareol | 515-03-7 | DEFHJ |
| 1029 | Sclareol oxide | 5153-92-4 | DEFHJK |
| 1031 | Selina-3,7(11)-diene | 6813-21-4 | DEFHJKL |
| 1032 | 2-(1-(3,3-dimethylcyclohexyl)ethoxy)-2-methylpropyl cyclopropanecarboxylate | 477218-42-1 | DEFHJ |
| 1033 | 3-(4-isobutylphenyl)-2-methylpropanal | 6658-48-6 | DHJK |
| 1035 | Spathulenol | 6750-60-3 | DEFHJK |
| 1036 | Spirambrene | 533925-08-5 | BCEFHJK |
| 1037 | Spirodecane | 6413-26-9 | BCEFGIJKL |
| 1038 | 1-(spiro[4.5]dec-7-en-7-yl)pent-4-en-1-one | 224031-70-3 | DGJK |
| 1042 | 2-(4-methylthiazol-5-yl)ethan-1-ol | 137-00-8 | CGIKL |
| 1043 | 2-(heptan-3-yl)-1,3-dioxolane | 4359-47-1 | ACEFHIJKL |
| 1045 | (Z)-dodec-4-enal | 21944-98-9 | BDFHJK |
| 1046 | tau-Cadinol | 5937-11-1 | DEFHJK |
| 1047 | tau-Muurolol | 19912-62-0 | DEFHJK |
| 1053 | Tetrahydrojasmone | 13074-63-0 | BDFHIJKL |
| 1057 | 2,6,10,10-tetramethyl-1-oxaspiro[4.5]dec-6-ene | 36431-72-8 | BDFHIJKL |
| 1059 | Thiomenthone | 38462-22-5 | BDEFHIJKL |
| 1060 | Thujopsene | 470-40-6 | BDEFGJKL |
| 1062 | Thymol methyl ether | 1076-56-8 | ADHIJKL |
| 1063 | 1-(2,2,6-trimethylcyclohexyl)hexan-3-ol | 70788-30-6 | DEFHJK |
| 1064 | trans, trans-2,4-Nonadienal | 5910-87-2 | ACHKL |
| 1065 | trans, trans-Farnesol | 106-28-5 | DEFHJK |
| 1066 | trans-2, cis-6-Nonadienal | 557-48-2 | ACHKL |
| 1067 | trans-2-Decenal | 3913-81-3 | ADHKL |
| 1070 | trans-2-Nonen-1-al | 18829-56-6 | ADHKL |
| 1072 | trans-3, cis-6-nonadienol | 56805-23-3 | ACEFHK |
| 1073 | trans-4-Decen-1-al | 65405-70-1 | ADHKL |
| 1075 | trans-ambrettolide | 51155-12-5 | DGJ |
| 1077 | trans-beta-ocimene | 13877-91-3 | ADGIKL |
| 1078 | trans-beta-Ocimene | 3779-61-1 | ADGIKL |
| 1082 | trans-Geraniol | 106-24-1 | BCHIK |
| 1083 | trans-Hedione | 2570-03-8 | DFHJK |
| 1085 | 7-(1,1-Dimethylethyl)-2H-1,5-benzodioxepin-3(4H)-one | 195251-91-3 | CEFHJ |
| 1089 | Tricyclone | 68433-81-8 | DEFHJK |
| 1090 | Tridecyl alcohol | 112-70-9 | DEFGJK |
| 1091 | Triethyl citrate | 77-93-0 | CEFGJ |
| 1093 | Methyl 2-((1-hydroxy-3-phenylbutyl)amino)benzoate | 144761-91-1 | DFHJ |
| 1095 | 1-((2E,5Z,9Z)-2,6,10-trimethylcyclododeca-2,5,9-trien-1-yl)ethan-1-one | 28371-99-5 | DHJK |
| 1097 | Decahydro-2,6,6,7,8,8-hexamethyl-2h-indeno(4,5-b)furan | 338735-71-0 | BDEFHJK |
| 1099 | 13-methyl oxacyclopentadec-10-en-2-one | 365411-50-3 | DEFHJK |
| 1102 | Undecanal | 112-44-7 | BDHJK |
| 1104 | (E)-4-methyldec-3-en-5-ol | 81782-77-6 | BDEFHIJK |
| 1105 | Valencene | 4630-07-3 | BDEFHJK |
| 1107 | Valerianol | 20489-45-6 | DEFHJK |
| 1111 | Vanillin isobutyrate | 20665-85-4 | CHJ |

TABLE 1-continued

List of materials with at least one MORV from 1 to 5

| Number | Material Name | CAS Number | Comment Code |
|---|---|---|---|
| 1113 | Vaniwhite ® | 5533-03-9 | CGIK |
| 1116 | (Z)-2-methyl-4-(2,6,6-trimethylcyclohex-2-en-1-yl)but-2-enal | 68555-62-4 | BDFHJK |
| 1117 | Methyl 2,4-dihydroxy-3,6-dimethylbenzoate | 4707-47-5 | CGIJ |
| 1120 | 1-methoxy-3a,4,5,6,7,7a-hexahydro-1H-4,7-methanoindene | 27135-90-6 | ACEFHJKL |
| 1121 | Methyl (Z)-2-((3-(4-(tert-butyl)phenyl)-2-methylpropylidene)amino)benzoate | 91-51-0 | DFHJ |
| 1125 | (Z)-hex-3-en-1-yl isobutyrate | 41519-23-7 | ADEFHJKL |
| 1126 | Vertacetal | 5182-36-5 | BCFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1135 | Vetiverol | 89-88-3 | CEFHIJK |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1138 | (2Z,6E)-nona-2,6-dienenitrile | 67019-89-0 | ACEFHKL |
| 1139 | (Z)-cyclooct-4-en-1-yl methyl carbonate | 87731-18-8 | BCHJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1146 | 4-(4-hydroxy-3-methoxyphenyl)butan-2-one | 122-48-5 | CEFGJ |
| 1147 | (1R,8aR)-4-isopropyl-1,6-dimethyl-1,2,3,7,8,8a-hexahydronaphthalene | 41929-05-9 | DEFHJKL |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 2

List of materials with at least one MORV greater than 5 to 10

| Number | Material Name | CAS Number | Comment Code |
|---|---|---|---|
| 2 | 2,4-dimethyl-2-(5,5,8,8-tetramethyl-5,6,7,8-tetrahydronaphthalen-2-yl)-1,3-dioxolane | 131812-67-4 | DFHJ |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 141 | 2,4-dimethyl-4,4a,5,9b-tetrahydroindeno[1,2-d][1,3]dioxine | 27606-09-3 | CEFHJK |
| 185 | (1-methyl-2-((1,2,2-trimethylbicyclo[3.1.0]hexan-3-yl)methyl)cyclopropyl)methanol | 198404-98-7 | DEFHJK |
| 227 | Isobornylcyclohexanol | 68877-29-2 | DEFHJK |
| 230 | Isobornyl cyclohexanol | 66072-32-0 | DEFHJK |
| 246 | Indol/Hydroxycitronellal Schiff base | 67801-36-9 | DEFHJ |

TABLE 2-continued

| List of materials with at least one MORV greater than 5 to 10 | | | |
|---|---|---|---|
| Number | Material Name | CAS Number | Comment Code |
| 248 | Hydroxymethyl isolongifolene | 59056-64-3 | DEFHJK |
| 343 | 8,8-dimethyl-3a,4,5,6,7,7a-hexahydro-1H-4,7-methanoinden-6-yl propionate | 76842-49-4 | DEFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 565 | Cedryl methyl ether | 19870-74-7 | BDEFHJK |
| 631 | beta-Copaene | 18252-44-3 | BDEFHJKL |
| 659 | 2'-isopropyl-1,7,7-trimethylspiro[bicyclo[2.2.1]heptane-2,4'-[1,3]dioxane] | 869292-93-3 | BDEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | DEFHJK |
| 715 | alpha-Cedrene epoxide | 13567-39-0 | BDEFHJK |
| 758 | Acetoxymethyl-isolongifolene (isomers) | 59056-62-1 | DEFHJK |
| 1028 | Sclareol | 515-03-7 | DEFHJ |
| 1097 | Decahydro-2,6,6,7,8,8-hexamethyl-2h-indeno(4,5-b)furan | 338735-71-0 | DEFHJK |

TABLE 3

| List of materials with at least one MORV from 0.5 to less than 1 | | | |
|---|---|---|---|
| Number | Material Name | CAS Number | Comment Code |
| 12 | 1-ethoxy-4-(tert-pentyl)cyclohexane | 181258-89-9 | ADEFHJK |
| 19 | (3Z)-1-(2-buten-1-yloxy)-3-hexene | 888744-18-1 | ADEFHJKL |
| 20 | 4-(2-methoxypropan-2-yl)-1-methylcyclohex-1-ene | 14576-08-0 | ADHIJKL |
| 24 | O-Methyl linalool | 60763-44-2 | ADHIJKL |
| 26 | o-Methoxycinnamaldehyde | 1504-74-1 | ACHK |
| 27 | Octanal, 3,7-dimethyl- | 25795-46-4 | ADGIJKL |
| 53 | 3,3-Dimethyl-5(2,2,3-Trimethyl-3-Cyclopenten-1yl)-4-Penten-2-ol | 329925-33-9 | CEFHJ |
| 54 | n-Hexyl salicylate | 6259-76-3 | DEFHJ |
| 55 | n-Hexyl 2-butenoate | 19089-92-0 | ADEFHJKL |
| 59 | Neryl Formate | 2142-94-1 | BCEFHJK |
| 72 | Methyl-beta-ionone | 127-43-5 | DHJK |
| 73 | Myroxide | 28977-57-3 | ADGIJKL |
| 81 | (E)-3,7-dimethylocta-4,6-dien-3-ol | 18479-54-4 | BCEFGIJK |
| 84 | (Z)-hex-3-en-1-yl cyclopropanecarboxylate | 188570-78-7 | BCEFHIKL |
| 96 | Methyl phenyl carbinyl propionate | 120-45-6 | BCHJK |
| 97 | Methyl phenylacetate | 101-41-7 | ACEFHIKL |
| 107 | 2-methyl-6-oxaspiro[4.5]decan-7-one | 91069-37-3 | BCEFGIKL |
| 111 | Methyl geraniate | 2349-14-6 | BCHJKL |
| 115 | 2-ethoxy-4-(methoxymethyl)phenol | 5595-79-9 | CFGK |
| 116 | Methyl cyclopentylideneacetate | 40203-73-4 | ACEFHIKL |
| 125 | Methoxymelonal | 62439-41-2 | ACGIJK |
| 133 | ((1s,4s)-4-isopropylcyclohexyl)methanol | 13828-37-0 | BDEFHIJK |
| 147 | Linalyl propionate | 144-39-8 | BDFHJK |
| 150 | Linalyl formate | 115-99-1 | ACFHJK |
| 151 | Linalyl butyrate | 78-36-4 | BDEFHJK |
| 154 | Linalyl acetate | 115-95-7 | BDHJK |

TABLE 3-continued

| List of materials with at least one MORV from 0.5 to less than 1 | | | |
|---|---|---|---|
| Number | Material Name | CAS Number | Comment Code |
| 157 | Linalool | 78-70-6 | BCEFGIJK |
| 163 | (Z)-hex-3-en-1-yl methyl carbonate | 67633-96-9 | ACEFGKL |
| 166 | Lepidine | 491-35-0 | BCEFHIKL |
| 169 | L-Carvone | 6485-40-1 | ACGIJKL |
| 181 | Khusinil | 75490-39-0 | DHJK |
| 191 | Isoraldeine | 1335-46-2 | BDHIJK |
| 194 | Isopropylvinylcarbinol | 4798-45-2 | ACGIKL |
| 198 | Isopropyl 2-methylbutyrate | 66576-71-4 | ACEFGIJKL |
| 201 | Isopentyrate | 80118-06-5 | ADEFGIJKL |
| 204 | Isononyl acetate | 40379-24-6 | BDEFHJKL |
| 205 | Isononanol | 27458-94-2 | BDEFGIKL |
| 213 | Isoeugenyl acetate | 93-29-8 | CFHJK |
| 214 | Isoeugenol | 97-54-1 | CEFHIK |
| 232 | Isoborneol | 124-76-5 | ACEFHIJKL |
| 237 | Isoamyl octanoate | 2035-99-6 | DEFHJK |
| 239 | Isoamyl isobutyrate | 2050-01-3 | ACEFGIJKL |
| 255 | Hydrocinnamic acid | 501-52-0 | CEFHIK |
| 258 | Hydratopic alcohol | 1123-85-9 | BCEFHIK |
| 264 | Hexyl propanoate | 2445-76-3 | ADEFHIKL |
| 270 | Hexyl butyrate | 2639-63-6 | BDEFHJKL |
| 273 | Hexyl 2-methylbutanoate | 10032-15-2 | BDEFHJKL |
| 275 | Hexyl 2-furoate | 39251-86-0 | DEFHJK |
| 282 | Heptyl alcohol | 111-70-6 | ACEFGIKL |
| 283 | Heptyl acetate | 112-06-1 | ADEFHKL |
| 284 | Heptaldehyde | 111-71-7 | ACHIKL |
| 287 | Heliotropin | 120-57-0 | BCGIK |
| 302 | Geranyl nitrile | 5146-66-7 | BCEFHKL |
| 306 | Geranyl formate | 105-86-2 | BCEFHJK |
| 308 | Geranyl caprylate | 51532-26-4 | DEFHJ |
| 310 | Geranyl benzoate | 94-48-4 | DFHJ |
| 312 | Geranial | 141-27-5 | ACHIKL |
| 314 | N,2-dimethyl-N-phenylbutanamide | 84434-18-4 | BCEFHJK |
| 319 | gamma-Terpinene | 99-85-4 | ADEFGIJKL |
| 346 | 2-(sec-butyl)cyclohexan-1-one | 14765-30-1 | ADFHIKL |
| 354 | 3-(2-ethylphenyl)-2,2-dimethylpropanal | 67634-14-4 | BDHJK |
| 355 | 2-(tert-butyl)cyclohexyl ethyl carbonate | 67801-64-3 | BDFHJK |
| 365 | 2-(tert-butyl)cyclohexyl ethyl carbonate | 81925-81-7 | ACFHIKL |
| 366 | Fenchyl alcohol | 1632-73-1 | ACGIJKL |
| 376 | Eucalyptol | 470-82-6 | ADEFGIJKL |
| 379 | Ethyl vanillin acetate | 72207-94-4 | CHJ |
| 387 | Ethyl octanoate | 106-32-1 | BDEFHJKL |
| 400 | Ethyl cinnamate | 103-36-6 | BCEFHK |
| 412 | Ethyl 2-(cyclohexyl)propionate | 2511-00-4 | BDFHIJKL |
| 419 | d-p-8(9)-Menthen-2-one | 5524-05-0 | ACGIJKL |
| 420 | 4-methyl-2-phenyltetrahydro-2H-pyran | 94201-73-7 | BDEFHJK |
| 437 | Dihydromyrcenol | 18479-58-8 | ADEFGIJK |
| 438 | Dihydrojasmone | 1128-08-1 | BCFHIJKL |
| 439 | Dihydroisophorone | 873-94-9 | ACEFGIJKL |
| 440 | Dihydroeugenol | 2785-87-7 | CEFHIJK |
| 442 | Dihydrocoumarin | 119-84-6 | BCGIKL |
| 443 | Dihydrocarvone | 7764-50-3 | ACGIJKL |
| 447 | Dihydro-alpha-terpinyl acetate | 80-25-1 | BDEFHIJKL |
| 448 | Dihydro-alpha-ionone | 31499-72-6 | BDHIJK |
| 454 | Dibenzyl ether | 103-50-4 | DEFHJK |
| 455 | Dibutyl o-phthalate | 84-74-2 | DEFHJ |
| 469 | 2-pentylcyclopentan-1-one | 4819-67-4 | BDFHIKL |
| 472 | Decyl anthranilate | 18189-07-6 | DEFHJ |
| 477 | Methyl (1s,4s)-1,4-dimethylcyclohexane-1-carboxylate | 23059-38-3 | ADEFHIJKL |
| 481 | Cyclohexylethyl acetate | 21722-83-8 | BDEFHJKL |
| 492 | Creosol | 93-51-6 | BCHIK |
| 495 | Cosmene | 460-01-5 | ADEFGIKL |
| 496 | 4-cyclohexyl-2-methylbutan-2-ol | 83926-73-2 | BDEFGIJK |
| 504 | 2-benzyl-2-methylbut-3-enenitrile | 97384-48-0 | BDHJK |

TABLE 3-continued

List of materials with at least one MORV from 0.5 to less than 1

| Number | Material Name | CAS Number | Comment Code |
|---|---|---|---|
| 509 | Citronellyl nitrile | 51566-62-2 | BCEFGIKL |
| 510 | Citronellyl phenylacetate | 139-70-8 | DFHJ |
| 512 | Citronellyl formate | 105-85-1 | BCEFGJKL |
| 515 | Citronellyl benzoate | 10482-77-6 | DFHJ |
| 517 | Citronellol | 106-22-9 | BCHIJKL |
| 518 | Citronellal | 106-23-0 | ACHIJKL |
| 522 | Citral | 5392-40-5 | ACHIKL |
| 525 | cis-Pinane | 6876-13-7 | ADEFGIJKL |
| 526 | (Z)-3-methyl-2-(pent-2-en-1-yl)cyclopent-2-en-1-one | 488-10-8 | BCHIJKL |
| 528 | cis-iso-Eugenol | 5912-86-7 | CEFHIK |
| 535 | cis-3-Hexenyl valerate | 35852-46-1 | BDEFHJKL |
| 536 | cis-3-Hexenyl tiglate | 67883-79-8 | BDEFHJK |
| 538 | cis-3-Hexenyl propionate | 33467-74-2 | ACEFHIKL |
| 540 | cis-3-Hexenyl butyrate | 16491-36-4 | ADEFHJKL |
| 542 | cis-3-Hexen-1-ol | 928-96-1 | ACEFHIKL |
| 547 | cis-2-Hexenol | 928-94-9 | ACEFHIKL |
| 549 | Cinnamyl nitrile | 4360-47-8 | ACEFGIK |
| 554 | Cinnamic aldehyde | 104-55-2 | ACHIK |
| 556 | Cinnamyl nitrile | 1885-38-7 | ACEFGIK |
| 557 | Chloroxylenol | 88-04-0 | BCHIJK |
| 575 | Carvacrol | 499-75-2 | DHIJK |
| 576 | Carvone | 99-49-0 | ACGIJKL |
| 579 | Carbitol | 111-90-0 | BCEFGIK |
| 583 | Caproyl alcohol | 111-27-3 | ACEFGIKL |
| 585 | 2-(2,2,3-trimethylcyclopent-3-en-1-yl)acetonitrile | 15373-31-6 | ACGIJKL |
| 588 | Camphor | 76-22-2 | ACEFGIJKL |
| 602 | (E)-2-methyl-4-(2,6,6-trimethylcyclohex-1-en-1-yl)but-2-enal | 3155-71-3 | DHJK |
| 605 | Borneol | 507-70-0 | ACEFHIJKL |
| 617 | beta-Pinene epoxide | 6931-54-0 | ACEFGIJKL |
| 619 | beta-Phellandrene | 555-10-2 | ADEFGIJKL |
| 640 | Benzylacetone | 2550-26-7 | ACEFGIK |
| 641 | Benzyl salicylate | 118-58-1 | DFGJ |
| 645 | Benzyl isovalerate | 103-38-8 | BDEFHJK |
| 647 | Benzyl isobutyrate | 103-28-6 | BCHJK |
| 651 | Benzyl butyrate | 103-37-7 | BCEFHJK |
| 652 | Benzyl alcohol | 100-51-6 | ACEFGIKL |
| 662 | 1-(3,3-dimethylcyclohexyl)ethyl formate | 25225-08-5 | ADEFHIJKL |
| 664 | Anisyl acetate | 104-21-2 | BCEFGK |
| 665 | Anisyl formate | 122-91-8 | BCEFGK |
| 667 | Anethole | 104-46-1 | ACEFHK |
| 672 | Amyl benzoate | 2049-96-9 | DEFHJK |
| 687 | alpha-Terpinyl acetate | 80-26-2 | BDHJK |
| 699 | alpha-methyl-cyclohexanepropanol | 10528-67-3 | BDEFHIK |
| 701 | alpha-methyl cinnamaldehyde | 101-39-3 | ACHIK |
| 703 | alpha-Isomethylionone | 127-51-5 | BDHIJK |
| 740 | 2,5-Dimethyl-4-methoxy-3(2H)-furanone | 4077-47-8 | ACEFGIJKL |
| 743 | Allyl phenoxyacetate | 7493-74-5 | BCGK |
| 744 | Allyl Phenethyl ether | 14289-65-7 | ACEFHK |
| 745 | Allyl heptanoate | 142-19-8 | ADEFHJKL |
| 755 | N-ethyl-N-(m-tolyl)propionamide | 179911-08-1 | CEFHJK |
| 760 | 3-hydroxybutan-2-one | 513-86-0 | ACEFGIKL |
| 761 | Acetoanisole | 100-06-1 | BCEFHIK |
| 777 | 6-Methylquinoline | 91-62-3 | BCEFHIKL |
| 779 | 6,8-Diethyl-2-nonanol | 70214-77-6 | BDEFGIJKL |
| 784 | 5-Methyl-3-heptanone | 541-85-5 | ACFGIKL |
| 789 | 4-Vinylphenol | 2628-17-3 | BCHIK |
| 796 | 4-hydroxy-3-methoxy-cinnamaldehyde | 458-36-6 | CH |
| 797 | 4-Ethylguaiacol | 2785-89-9 | CEFHIK |
| 799 | 4-Damascol | 4927-36-0 | BDFHJK |
| 808 | 3-methyl-4-phenylpyrazole | 13788-84-6 | CEFHK |
| 810 | 3-Methyl-1,2-cyclopentanedione | 765-70-8 | ACEFGIKL |
| 811 | 3-Methoxy-5-methylphenol | 3209-13-0 | BCHIK |
| 812 | 3-Methoxy-3-Methyl Butanol | 56539-66-3 | ACGIKL |
| 817 | 3-Hexenol | 544-12-7 | ACEFHIKL |

TABLE 3-continued

List of materials with at least one MORV from 0.5 to less than 1

| Number | Material Name | CAS Number | Comment Code |
|---|---|---|---|
| 819 | 3,7-dimethyl-2-methylene-6-octenal | 22418-66-2 | ADFHIJK |
| 820 | 3,7-dimethyl-1-octanol | 106-21-8 | BDEFGIJKL |
| 832 | 2-Phenylethyl acetate | 103-45-7 | BCEFHK |
| 835 | 2-Phenethyl propionate | 122-70-3 | BCEFHJK |
| 836 | 2-Pentylcyclopentan-1-ol | 84560-00-9 | DEFHIKL |
| 838 | 2-nonanone propylene glycol acetal | 165191-91-3 | BDEFHJK |
| 845 | 2-Methoxy-3-(1-methylpropyl)pyrazine | 24168-70-5 | BCEFGIK |
| 846 | 2-isopropyl-N,2,3-trimethylbutyramide | 51115-67-4 | ACEFGIJK |
| 847 | 2-Isopropyl-5-methyl-2-hexenal | 35158-25-9 | ADFGIJKL |
| 848 | 2-Isopropyl-4-methylthiazole | 15679-13-7 | ACHIJKL |
| 851 | 2-Hexen-1-ol | 2305-21-7 | ACEFHIKL |
| 858 | 2-Butoxyethanol | 111-76-2 | ACEFGIKL |
| 875 | 1,4-Cineole | 470-67-7 | ADGIJKL |
| 880 | 1-(2,6,6-Trimethyl-2-cyclohexen-1-yl)-2-buten-1-one | 43052-87-5 | BDHIJK |
| 882 | (Z)-3-hepten-1-yl acetate | 1576-78-9 | ACEFHKL |
| 883 | (S)-(1R,5R)-4,6,6-trimethylbicyclo[3.1.1]hept-3-en-2-one | 1196-01-6 | ACEFGIJKL |
| 888 | (R)-(−)-Linalool | 126-91-0 | BCEFGIJK |
| 889 | (l)-Citronellal | 5949-05-3 | ACHIJKL |
| 891 | (d)-Citronellal | 2385-77-5 | ACHIJKL |
| 899 | (+)-Citronellol | 1117-61-9 | BCHIJKL |
| 900 | (−)-Citronellol | 7540-51-4 | BCHIJKL |
| 901 | (+)-alpha-Pinene | 7785-70-8 | ADEFGIJKL |
| 902 | (+)-Carvone | 2244-16-8 | ACGIJKL |
| 903 | (−)-alpha-Pinene | 7785-26-4 | ADEFGIJKL |
| 904 | Methyl 2-methylbutyrate | 868-57-5 | ACEFGIKL |
| 909 | Hexyl tiglate | 16930-96-4 | BDEFHJKL |
| 918 | Allyl 2-(cyclohexyloxy)acetate | 68901-15-5 | CHJK |
| 921 | 1,5-dimethylbicyclo[3.2.1]octan-8-one oxime | 75147-23-8 | CFHIJK |
| 931 | alpha-acetoxystyrene | 2206-94-2 | ACEFHIK |
| 940 | p-Cymene | 99-87-6 | ADGIJKL |
| 956 | Phenethyl formate | 104-62-1 | ACEFHK |
| 958 | Phenethyl isobutyrate | 103-48-0 | DHJK |
| 960 | Phenethyl tiglate | 55719-85-2 | DHJK |
| 971 | Phenylethyl methacrylate | 3683-12-3 | DHJK |
| 977 | p-Isopropylphenylacetaldehyde | 4395-92-0 | BDFHK |
| 981 | 1,2-dimethyl-3-(prop-1-en-2-yl)cyclopentan-1-ol | 72402-00-7 | BCEFGIJKL |
| 983 | p-Methoxyphenylacetone | 122-84-9 | BCEFHK |
| 986 | (2Z,5Z)-5,6,7-trimethylocta-2,5-dien-4-one | 358331-95-0 | ADHIJKL |
| 987 | p-Propyl anisole | 104-45-0 | ADEFHKL |
| 994 | p-t-butyl phenyl acetaldehyde | 109347-45-7 | BDHJK |
| 995 | p-tert-Amyl cyclohexanol | 5349-51-9 | BDEFHIJK |
| 1001 | Racemic alpha-Pinene | 80-56-8 | ADEFGIJKL |
| 1002 | 4-(4-hydroxyphenyl)butan-2-one | 5471-51-2 | CEFGIK |
| 1004 | Rhodinol | 141-25-3 | BCHIJKL |
| 1005 | Ethyl (2,3,6-trimethylcyclohexyl)carbonate | 93981-50-1 | BDEFHJKL |
| 1011 | 1-(3,3-dimethylcyclohexyl)ethyl acetate | 25225-10-9 | ADHIJKL |
| 1017 | S)-(+)-Linalool | 126-90-9 | BCEFGIJK |
| 1018 | Sabinene | 3387-41-5 | ADEFGIJKL |
| 1019 | Sabinene hydrate | 546-79-2 | ADEFGIJKL |
| 1030 | Propyl (S)-2-(tert-pentyloxy)propanoate | 319002-92-1 | BDEFHJK |
| 1039 | Spirolide | 699-61-6 | BCGIKL |
| 1040 | (Z)-5-methylheptan-3-one oxime | 22457-23-4 | BCEFGIJKL |
| 1041 | 1-phenylethyl acetate | 93-92-5 | ACEFHIK |
| 1051 | Tetrahydrogeranial | 5988-91-0 | ADGIJKL |
| 1052 | Tetrahydroionol | 4361-23-3 | BDEFHIJK |

TABLE 3-continued

List of materials with at least one MORV from 0.5 to less than 1

| Number | Material Name | CAS Number | Comment Code |
|---|---|---|---|
| 1054 | Tetrahydrolinalool | 78-69-3 | BDEFGIJKL |
| 1055 | Tetrahydrolinalyl acetate | 20780-48-7 | ADEFHJKL |
| 1058 | Ethyl (1R,6S)-2,2,6-trimethylcyclohexane-1-carboxylate | 22471-55-2 | ADEFHIJKL |
| 1061 | Thymol | 89-83-8 | BDHIJK |
| 1069 | trans-2-Hexenol | 928-95-0 | ACEFHIKL |
| 1071 | trans-2-tert-Butylcyclohexanol | 5448-22-6 | ACGIJKL |
| 1074 | trans-alpha-Damascone | 24720-09-0 | BDHIJK |
| 1076 | trans-Anethole | 4180-23-8 | ACEFHK |
| 1079 | trans-Cinnamic acid | 140-10-3 | CEFHK |
| 1081 | trans-Dihydrocarvone | 5948-04-9 | ACGIJKL |
| 1084 | trans-Isoeugenol | 5932-68-3 | CEFHIK |
| 1088 | Trichloromethyl phenyl carbinyl acetate | 90-17-5 | BDEFGJ |
| 1098 | 2-mercapto-2-methylpentan-1-ol | 258823-39-1 | ACEFHIJKL |
| 1110 | Vanillin acetate | 881-68-5 | CH |
| 1112 | Vanitrope | 94-86-0 | CEFHK |
| 1115 | 2,2,5-trimethyl-5-pentylcyclopentan-1-one | 65443-14-3 | BDFGIJKL |
| 1118 | Veratraldehyde | 120-14-9 | BCGIK |
| 1119 | (1R,5R)-4,6,6-trimethylbicyclo[3.1.1]hept-3-en-2-one | 18309-32-5 | ACEFGIJKL |
| 1122 | Verdol | 13491-79-7 | ACGIJKL |
| 1127 | 4-(tert-butyl)cyclohexyl acetate | 10411-92-4 | BDEFHJK |
| 1128 | 4-(tert-butyl)cyclohexyl acetate | 32210-23-4 | BDEFHJK |
| 1133 | Vethymine | 7193-87-5 | CEFGK |
| 1134 | 4-methyl-4-phenylpentan-2-yl acetate | 68083-58-9 | BDFHJK |
| 1141 | (Z)-1-((2-methylallyl)oxy)hex-3-ene | 292605-05-1 | ADEFHKL |

TABLE 4

List of materials with ALL MORVs from 1 to 5

| Number | Material Name | CAS Number | Comment Code |
|---|---|---|---|
| 7 | 3-methoxy-7,7-dimethyl-10-methylenebicyclo[4.3.1]decane | 216970-21-7 | BDEFHJK |
| 14 | Oxyoctaline formate | 65405-72-3 | DFHJK |
| 39 | 2,2,6,8-tetramethyl-1,2,3,4,4a,5,8,8a-octahydronaphthalen-1-ol | 103614-86-4 | DEFHIJK |
| 48 | Nootkatone | 4674-50-4 | DHJK |
| 183 | Khusimol | 16223-63-5 | CEFHJK |
| 199 | Isopimpinellin | 482-27-9 | CFGJ |
| 206 | Iso3-methylcyclopentadecan-1-one | 3100-36-5 | DEFGJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 229 | Isobornyl isobutyrate | 85586-67-0 | BDEFHIJK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 281 | 3a,4,5,6,7,7a-hexahydro-1H-4,7-methanoinden-6-yl acetate | 5413-60-5 | CEFGJK |
| 329 | gamma-Eudesmol | 1209-71-8 | DFHJK |
| 335 | 4,6,6,7,8,8-hexamethyl-1,3,4,6,7,8-hexahydrocyclopenta[g]isochromene | 1222-05-5 | DEFHJK |
| 353 | (Z)-6-ethylideneoctahydro-2H-5,8-methanochromen-2-one | 69486-14-2 | CEFGJK |
| 360 | 8,8-dimethyl-3a,4,5,6,7,7a-hexahydro-1H-4,7-methanoinden-6-yl acetate | 171102-41-3 | DEFHJK |

TABLE 4-continued

List of materials with ALL MORVs from 1 to 5

| Number | Material Name | CAS Number | Comment Code |
|---|---|---|---|
| 441 | Octahydro-1H-4,7-methanoinden-5-yl acetate | 64001-15-6 | DEFHJKL |
| 484 | 3a,4,5,6,7,7a-hexahydro-1H-4,7-methanoinden-6-yl butyrate | 113889-23-9 | DEFHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 501 | (E)-cycloheptadec-9-en-1-one | 542-46-1 | DEFGJ |
| 566 | Cedryl formate | 39900-38-4 | BDEFHJK |
| 567 | Cedryl acetate | 77-54-3 | DEFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 573 | Caryophyllene alcohol acetate | 32214-91-8 | DEFHJK |
| 574 | Caryolan-1-ol | 472-97-9 | DEFHJK |
| 603 | Bornyl isobutyrate | 24717-86-0 | BDEFHIJK |
| 616 | beta-Santalol | 77-42-9 | DEFHJK |
| 621 | beta-Patchoulline | 514-51-2 | BDEFGJKL |
| 624 | beta-Himachalene Oxide | 57819-73-5 | BDFHJK |
| 627 | (2,2-dimethoxyethyl)benzene | 101-48-4 | DHJK |
| 632 | beta-Cedrene | 546-28-1 | BDEFGJKL |
| 663 | Anisyl phenylacetate | 102-17-0 | DFHJ |
| 680 | 2,2,6,6,7,8,8-heptamethyldecahydro-2H-indeno[4,5-b]furan | 647828-16-8 | ADEFHJK |
| 684 | alpha-Vetivone | 15764-04-2 | DHJK |
| 694 | alpha-Santalol | 115-71-9 | DEFHJK |
| 696 | alpha-Patchoulene | 560-32-7 | ADEFHJKL |
| 708 | alpha-Gurjunene | 489-40-7 | BDEFHJKL |
| 712 | alpha-Eudesmol | 473-16-5 | DEFHJK |
| 714 | alpha-Cubebene | 17699-14-8 | ADEFHJKL |
| 726 | alpha-Agarofuran | 5956-12-7 | BDEFHJK |
| 750 | Allo-aromadendrene | 25246-27-9 | BDEFHJKL |
| 764 | Acetarolle ® | 744266-61-3 | DFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 788 | 5-Cyclohexadecenone | 37609-25-9 | DEFGJK |
| 804 | 3-Thujopsanone | 25966-79-4 | BDEFHJK |
| 872 | 10-epi-gamma-Eudesmol | 15051-81-7 | DFHJK |
| 919 | 3a,4,5,6,7,7a-hexahydro-1H-4,7-methanoinden-6-yl propionate | 17511-60-3 | CEFHJK |
| 927 | 5-Acetyl-1,1,2,3,3,6-hexamethylindan | 15323-35-0 | DEFHJK |
| 933 | Patchouli alcohol | 5986-55-0 | DEFHIJK |
| 978 | 3a,4,5,6,7,7a-hexahydro-1H-4,7-methanoinden-6-yl pivalate | 68039-44-1 | DEFHJK |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1022 | 2,2,7,9-tetramethylspiro(5.5)undec-8-en-1-one | 502847-01-0 | DHIJK |
| 1024 | (Z)-2-ethyl-4-(2,2,3-trimethylcyclopent-3-en-1-yl)but-2-en-1-ol | 28219-61-6 | DEFHJK |
| 1027 | 5-methoxyoctahydro-1H-4,7-methanoindene-2-carbaldehyde | 193425-86-4 | CHJK |
| 1029 | Sclareol oxide | 5153-92-4 | DEFHJK |
| 1035 | Spathulenol | 6750-60-3 | DEFHJK |
| 1038 | 1-(spiro[4.5]dec-7-en-7-yl)pent-4-en-1-one | 224031-70-3 | DGJK |
| 1060 | Thujopsene | 470-40-6 | BDEFGJKL |
| 1089 | Tricyclone | 68433-81-8 | DEFHJK |
| 1107 | Valerianol | 20489-45-6 | DEFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |

TABLE 4-continued

| List of materials with ALL MORVs from 1 to 5 | | | |
|---|---|---|---|
| Number | Material Name | CAS Number | Comment Code |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 5

| List of materials with ALL MORVs greater than 5 to 10 | | | |
|---|---|---|---|
| Number | Material Name | CAS Number | Comment Code |
| 248 | Hydroxymethyl isolongifolene | 59056-64-3 | BDEFHJK |

TABLE 6

| List of materials with ALL MORVs from 0.5 to less than 1 | | | |
|---|---|---|---|
| Number | Material Name | CAS Number | Comment Code |
| 472 | Decyl anthranilate | 18189-07-6 | DEFHJ |
| 526 | (Z)-3-methyl-2-(pent-2-en-1-yl)cyclopent-2-en-1-one | 488-10-8 | BCHIJKL |

The materials in Tables 1-6 can be supplied by one or more of the following: Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; and Bedoukian Research Inc. Danbury, Conn. USA.

Actual MORV values for each material listed in Tables 1-6 above are as follows:

| Material No. | MORV value for Equation a.) | MORV Value for Equation b.) | MORV Value for Equation c.) | MORV value for Equation d.) |
|---|---|---|---|---|
| 1 | 0.548223914 | 0.876283261 | 1.22018588 | −0.41901144 |
| 2 | 1.520311929 | 3.493450446 | 2.70657265 | 5.11342862 |
| 3 | 2.267801995 | −0.81712657 | 0.43218875 | 1.595983683 |
| 4 | −0.591063369 | −0.48283571 | 0.16199804 | 1.210497701 |
| 7 | 1.437444636 | 2.131822996 | 3.81633465 | 1.318339345 |
| 9 | 2.151445882 | −0.46189495 | 0.56090469 | 1.206360803 |
| 10 | 2.5733592 | −0.58780849 | 1.39751471 | 1.258361951 |
| 11 | 3.052627325 | 1.008519135 | −0.30475953 | 0.076323462 |
| 12 | 0.683776599 | −0.01157903 | 0.82853231 | 0.326169402 |
| 13 | 1.549643217 | 1.809183231 | 0.70864531 | 2.22799611 |
| 14 | 2.82111224 | 2.339505033 | 1.240818 | 2.502429355 |
| 16 | −0.31551128 | −0.06816599 | −0.04371934 | 2.76742389 |

-continued

| Material No. | MORV value for Equation a.) | MORV Value for Equation b.) | MORV Value for Equation c.) | MORV value for Equation d.) |
|---|---|---|---|---|
| 17 | −1.334904153 | −0.5773313 | 1.75644798 | 1.898455724 |
| 18 | −1.34154226 | −2.63596666 | 0.06885109 | 1.001431671 |
| 19 | 0.15532384 | 0.09866097 | 0.64214585 | −0.33330779 |
| 20 | 0.640261783 | 0.693213268 | 0.54637273 | −0.97556029 |
| 21 | 0.936895364 | −0.01521118 | 1.1697513 | −0.63510809 |
| 22 | 1.158981042 | 1.115900089 | −0.25859776 | 1.318200884 |
| 23 | 3.702361074 | 1.399942641 | 5.23954766 | 7.089933671 |
| 24 | 0.773874141 | 0.146848137 | −1.05705847 | −0.36193173 |
| 25 | −1.016103969 | −1.18967936 | 0.78064625 | 2.944710012 |
| 25 | −1.016103969 | −1.18967936 | 0.78064625 | 2.944710012 |
| 26 | 0.615085491 | −0.00096877 | −0.35697252 | −0.18121401 |
| 27 | 0.70261974 | −0.22197386 | 0.19710806 | −2.37196477 |
| 28 | 1.366472597 | −0.42546942 | −0.59394241 | −0.01417395 |
| 29 | 1.096043453 | −1.02972898 | −1.42167356 | −0.63817943 |
| 30 | 1.143415203 | −0.85945441 | −0.41416913 | 2.499807942 |
| 31 | 1.138642907 | −0.19595476 | −0.54547769 | −0.98828898 |
| 32 | 1.914414495 | −0.64487788 | 0.63212987 | 1.166699371 |
| 33 | 0.314847366 | 1.848003955 | −1.3905032 | −0.62848261 |
| 34 | −0.113542761 | 0.981530917 | 0.32824239 | 1.126524277 |
| 35 | 0.472382903 | 1.494882467 | −0.07201236 | −0.64589543 |
| 36 | 3.158513795 | 1.084094934 | −0.00328981 | −0.17786385 |
| 37 | −1.055631982 | 2.240172964 | 0.92596118 | 2.105391988 |
| 38 | 3.158513795 | 0.592820874 | −0.49326241 | 0.212867212 |
| 39 | 1.083800659 | 2.069727985 | 2.48170879 | 3.205630609 |
| 42 | −0.103134861 | 0.267726008 | −0.65350189 | 1.125952363 |
| 43 | 0.323961628 | 1.469295081 | −0.52991193 | 0.797908251 |
| 47 | 1.703678841 | 1.348737095 | 2.00634162 | −0.16505407 |
| 48 | 2.370955056 | 2.783472865 | 2.68240273 | 1.221864405 |
| 49 | 1.670680003 | −0.41866107 | −0.9173849 | 1.181929544 |
| 50 | 1.670680003 | 0.076369374 | −0.49915943 | −0.85392575 |
| 52 | 0.464485039 | 0.057512869 | 1.31230219 | −0.11170276 |
| 53 | 0.626671823 | −0.46954947 | −0.33383736 | 0.277079201 |
| 54 | 0.666149043 | 0.009549925 | −0.36226343 | 0.197224432 |
| 55 | 0.723473579 | −1.50916383 | −0.3848989 | −0.71458778 |
| 57 | 0.381273227 | 1.192994109 | 1.65593321 | −1.65739236 |
| 59 | 0.561360663 | −0.17793966 | −1.63250554 | −0.7564969 |
| 61 | 0.146473611 | −0.01535544 | −0.16339658 | 1.738656146 |
| 62 | 1.20162032 | −0.3576095 | −0.10695443 | 1.322155191 |
| 63 | 1.084291915 | 2.258720158 | −1.01245416 | 1.688283974 |
| 64 | 0.744770665 | 0.155243763 | −1.8029919 | 1.023503542 |
| 65 | 0.972835178 | 2.797151284 | 1.53453579 | 0.857051645 |
| 67 | 2.069410561 | 0.021831924 | 0.37855159 | −0.67235457 |
| 68 | 0.527636614 | 0.590831983 | 1.02843762 | 2.208655795 |
| 69 | 2.133965691 | 2.088998449 | 2.05751412 | −0.9433713 |
| 70 | 0.327378959 | 0.996844599 | 1.23648533 | −1.25138371 |
| 71 | 1.40093669 | 0.778222691 | 0.70401172 | −0.24075444 |
| 72 | 0.617697349 | −0.29503359 | 0.52404847 | 0.816184656 |
| 73 | 0.617792473 | 0.888976061 | −0.45289639 | 0.615659244 |
| 74 | 1.437359024 | 1.548292147 | 0.10314807 | −0.48982286 |
| 75 | −1.970885622 | 3.398008325 | 4.08025266 | −0.89948156 |
| 76 | −1.32746934 | −2.65365233 | 0.10272816 | 1.001614125 |
| 77 | −2.541686116 | 3.295534192 | 3.75284227 | 0.404837808 |
| 78 | −2.110794 | 2.109874746 | 3.13350902 | −0.3880285 |
| 79 | 1.641162056 | −0.28533994 | 1.53676145 | 0.652696023 |
| 80 | 1.594400214 | 0.283682865 | 2.23140233 | 1.111682021 |
| 81 | 0.176566806 | −2.0786518 | −2.13986952 | 0.981126964 |
| 82 | 0.980373758 | −0.28813159 | 0.19404501 | 1.252564677 |
| 83 | 0.941833098 | 0.317310013 | 1.17606727 | 0.72992237 |
| 84 | 0.774237336 | −0.27140727 | 0.72461427 | −1.56415746 |
| 85 | 2.092976965 | 0.810644229 | 0.82999192 | −0.62861806 |
| 91 | 2.061595915 | −0.79930338 | −0.18285395 | −0.66898499 |
| 92 | 2.068748434 | −0.24299896 | 0.07214682 | −1.11758276 |
| 93 | −0.08984279 | −1.06025959 | −0.05068694 | 1.560050105 |
| 96 | 0.927758203 | −0.44129515 | 0.89190422 | 0.744284978 |
| 97 | 0.658667572 | −0.68771072 | 0.46051026 | −0.53120883 |
| 98 | 0.853222693 | −0.2037738 | −0.21414441 | 1.119784962 |
| 100 | 1.654535066 | 0.995056228 | 2.35139085 | 0.543654824 |
| 101 | 2.173663649 | −0.11491477 | 1.48285148 | 1.698527571 |
| 102 | 2.066679492 | −0.16785146 | −0.84780149 | 0.12159477 |
| 103 | 2.335152618 | −0.02866585 | 0.16993375 | −0.98254522 |
| 104 | 2.760588276 | 0.459513599 | 1.35310241 | 0.000336976 |
| 105 | 1.654535066 | 3.654489674 | 3.13033965 | 0.544225478 |
| 106 | 1.750588169 | −0.55853348 | 0.50257773 | 1.630011313 |
| 107 | 0.896789863 | 0.73615897 | 0.53011623 | −0.54697747 |
| 108 | 0.532375207 | 0.826537134 | 1.21040312 | 0.690230716 |

-continued

| Material No. | MORV value for Equation a.) | MORV Value for Equation b.) | MORV Value for Equation c.) | MORV value for Equation d.) |
|---|---|---|---|---|
| 109 | 2.407655187 | 0.742651426 | 1.80322099 | 0.271832856 |
| 110 | 0.54830833 | 2.916795026 | 1.40126098 | 0.690230716 |
| 111 | 0.939597126 | −0.3750368 | −1.23479972 | −0.89366351 |
| 112 | 1.398518854 | 1.265740274 | 4.19618377 | −0.12762692 |
| 113 | 1.415726941 | 0.086297006 | 3.43559555 | −0.12964168 |
| 115 | −1.557729423 | −0.44113526 | 0.86330536 | 0.590708892 |
| 116 | 0.193562268 | −1.58091165 | 0.83247813 | −0.70978039 |
| 117 | 1.353510875 | −0.59062398 | −0.31776345 | −0.3050158 |
| 119 | 0.830052725 | 2.28725579 | 0.38409695 | 0.219336109 |
| 120 | 1.261997955 | −0.22622961 | −1.04772194 | 2.028504137 |
| 122 | 1.505653628 | −1.14748206 | −0.19760084 | −0.81373045 |
| 123 | −0.658721962 | −0.21299878 | 1.01439841 | −0.76731016 |
| 125 | 0.749676998 | −1.0761601 | 0.99563924 | −1.15409002 |
| 126 | 0.931054384 | −0.35067079 | 1.06050832 | −1.62171794 |
| 128 | −1.344832644 | −0.09451199 | 1.19145467 | 1.621274257 |
| 130 | 1.153249538 | 1.605070708 | 2.38047907 | −0.93842293 |
| 133 | 0.840066046 | 0.2323025 | 0.19054023 | −0.26588341 |
| 134 | 0.522267541 | 0.824106618 | 1.83479545 | 0.364403434 |
| 135 | 2.142817887 | 2.142411243 | −0.93830995 | 0.696522652 |
| 137 | 3.052627325 | 3.606270166 | 0.50445208 | 0.076323462 |
| 140 | −0.153437637 | 0.246303216 | 0.76565758 | 1.800968868 |
| 141 | 2.067620311 | 1.424830396 | 2.33536931 | 7.644025075 |
| 142 | 0.98353103 | 1.950251373 | 2.50851828 | −0.24499521 |
| 143 | 1.736969725 | 0.991537809 | 2.5691601 | 1.227191656 |
| 145 | −0.211768579 | 1.46336231 | −0.93580247 | −1.48749449 |
| 146 | 1.912710035 | 0.926306508 | 1.81253333 | 0.494121361 |
| 147 | 0.675736703 | 0.99202385 | −0.66034472 | −0.66302669 |
| 148 | 0.757176542 | 1.83006252 | 0.16210659 | 0.243674851 |
| 149 | 0.438772371 | 1.091438092 | −0.1560319 | −0.61711642 |
| 150 | 0.84399938 | 0.675302022 | −1.69771411 | −0.73841711 |
| 151 | 0.633570539 | 0.988413715 | −0.54991825 | −0.43550324 |
| 152 | 0.911582356 | 1.974700218 | −0.92267786 | 0.628660087 |
| 153 | 0.319053885 | 2.531735341 | −0.39139184 | 0.734629224 |
| 154 | 0.714814512 | 0.690769753 | −2.06588692 | −0.73356628 |
| 155 | −0.161798388 | 0.032135767 | −0.13802086 | 1.734928461 |
| 156 | −0.571799976 | −1.32834264 | −1.65346017 | 1.856689553 |
| 157 | 0.131224024 | 0.21510779 | −1.70996346 | 0.964902175 |
| 158 | 1.201616145 | −0.21158932 | −0.8501176 | −0.33330779 |
| 159 | 0.811289908 | 1.606645397 | 0.25352447 | −1.83775117 |
| 159 | 0.811289908 | 1.606645397 | 0.25352447 | −1.83775117 |
| 161 | 0.475184006 | 1.99305646 | 1.90910177 | 3.288337059 |
| 162 | 0.833030517 | 0.487189028 | 1.76798642 | 0.104378164 |
| 163 | 0.58993703 | −0.46431772 | 0.74883588 | −0.81090824 |
| 166 | −0.121286831 | −0.84664528 | −0.32625341 | 0.778055656 |
| 167 | 0.846400186 | −0.25922232 | 0.69248774 | 1.183696217 |
| 168 | −0.310930833 | −0.81048493 | 0.08527131 | 1.61831109 |
| 169 | −0.2346025 | 0.890438419 | −0.13206526 | −0.83961838 |
| 170 | −0.169223695 | 1.172917966 | −0.11306441 | 0.099121666 |
| 174 | 2.863652137 | 0.236674094 | −0.69038707 | 1.610215283 |
| 175 | 1.789769228 | −0.31740428 | −0.89529921 | −0.09686469 |
| 176 | 2.625947334 | 0.083548191 | 0.30634559 | −0.35925728 |
| 177 | 1.674319352 | −0.22179044 | 0.42093738 | −0.23683577 |
| 178 | 2.863652137 | 0.727069168 | −0.26724686 | −0.44888613 |
| 179 | 0.070511885 | 0.365852864 | 1.35327505 | −0.03748038 |
| 181 | 0.976254543 | 0.691638796 | 0.51371978 | −0.02503945 |
| 182 | −1.842503751 | −0.12688474 | 2.56277877 | 0.111744488 |
| 183 | 3.195758563 | 3.886545621 | 4.29482769 | 3.829845293 |
| 184 | 0.333889534 | −0.67236766 | 2.21605977 | 4.254612125 |
| 185 | 5.61162203 | 1.40458529 | 2.86231343 | 1.035135749 |
| 186 | 1.068190511 | −0.65969343 | −0.63104765 | −1.36962992 |
| 187 | 1.396358739 | 0.249705611 | 0.81449499 | −0.15353102 |
| 189 | 1.544466636 | −0.33742685 | 0.8096674 | −0.44483677 |
| 190 | −0.210918777 | −1.04086063 | 0.02614862 | 3.362615492 |
| 191 | 0.715897301 | 0.666316436 | −0.41719538 | 0.400723176 |
| 192 | 0.65612864 | 1.231196814 | 0.75462061 | 1.514581532 |
| 193 | −0.394884432 | 1.129269425 | −0.3157071 | −0.61478944 |
| 194 | −2.111794245 | −0.71010521 | 0.53077207 | 0.59302222 |
| 195 | 1.18880856 | 0.704463775 | 1.99312777 | 1.419709023 |
| 196 | 1.885714606 | 0.436434665 | 1.44657532 | 1.145809063 |
| 197 | 2.174580668 | 0.133070149 | 0.99814905 | 0.871658496 |
| 198 | −0.533922573 | −2.16213117 | 0.5812107 | −0.92280453 |
| 199 | 1.493919434 | 1.45125612 | 1.95141371 | 4.403441058 |
| 201 | −0.005520296 | −0.83362523 | 0.65480762 | −0.38894276 |
| 204 | 0.732981164 | −0.97494758 | −0.91192246 | −1.00034323 |
| 205 | 0.991838899 | −0.60053505 | −0.49983634 | 0.674468753 |

-continued

| Material No. | MORV value for Equation a.) | MORV Value for Equation b.) | MORV Value for Equation c.) | MORV value for Equation d.) |
|---|---|---|---|---|
| 206 | 2.147983695 | 1.291351958 | 1.64553247 | 1.626455601 |
| 208 | −0.386224123 | −0.24799559 | 1.19406353 | −1.61243489 |
| 209 | 1.447075297 | 0.122626462 | 1.08021156 | 0.473154634 |
| 210 | −0.386224123 | −0.24799559 | 1.19406353 | −1.61243489 |
| 211 | 2.186118467 | 1.873949371 | 0.64852028 | −0.59205851 |
| 212 | 1.367811201 | 1.689658923 | 1.8017376 | 2.525531645 |
| 213 | 0.925016223 | 0.875610609 | 0.31462609 | 0.847028648 |
| 214 | −0.239873321 | 1.808823425 | −0.36105512 | −0.07650286 |
| 215 | 2.264275088 | 1.360001278 | 3.25759951 | 2.147928282 |
| 218 | −0.509585598 | −0.93428643 | 1.63030386 | −0.79436377 |
| 221 | 1.876297063 | 0.026873469 | 0.45442758 | 1.538486988 |
| 227 | 5.317676982 | 2.824566654 | 1.73360625 | 3.103310061 |
| 228 | 3.323728685 | 1.554268023 | 1.8883835 | 0.957527434 |
| 229 | 3.218950175 | 1.464118271 | 2.47512497 | 1.214429025 |
| 230 | 5.242356467 | 3.482206715 | 3.50441556 | 1.614847073 |
| 230 | 5.242356467 | 3.482206715 | 3.50441556 | 1.614847073 |
| 231 | 2.710087358 | 1.517756148 | 0.35088855 | 0.603171932 |
| 231 | 2.710087358 | 1.517756148 | 0.35088855 | 0.603171932 |
| 232 | 0.703604481 | 0.42129186 | 0.39567696 | 0.41729786 |
| 233 | 1.312921486 | 0.816597603 | 2.17066283 | 0.472801294 |
| 234 | 0.874145958 | 0.741410502 | 1.71105733 | −0.47289415 |
| 237 | 0.778921491 | −1.02119303 | 0.4612164 | −0.8881184 |
| 238 | 0.681403734 | −0.342052 | 1.27750286 | −0.3383341 |
| 239 | −0.870637933 | −2.58292907 | 0.79173772 | −1.27888846 |
| 242 | 0.910211214 | 0.374558101 | 1.01712685 | 1.001043471 |
| 243 | 1.670680003 | 0.104780951 | −0.6545574 | −0.46985154 |
| 244 | 1.140332181 | 0.116513028 | 1.61110902 | 3.713305291 |
| 246 | −0.634992987 | 0.548746912 | 4.62542427 | 7.660969857 |
| 247 | −1.739729444 | −0.91508372 | 1.18693162 | 3.108631198 |
| 248 | 5.81821686 | 6.320330665 | 6.14379552 | 5.214046447 |
| 249 | 0.348188924 | −0.95333461 | −0.08432225 | 1.866717393 |
| 252 | 2.456287983 | −0.02516176 | 0.76814124 | 1.756087132 |
| 253 | 1.76915226 | 0.226389981 | −0.18115009 | −0.62385199 |
| 254 | 0.658956861 | −0.39322197 | −0.67153044 | 1.416053304 |
| 255 | 0.892122738 | −0.46985097 | 0.42813903 | −0.46752753 |
| 256 | 0.625043963 | −0.65111806 | 1.4319541 | 2.110656697 |
| 258 | −0.187789327 | −0.85870492 | −0.21766971 | 0.931521178 |
| 259 | −1.261365139 | −2.33099427 | 1.33595129 | 0.43644676 |
| 260 | 2.4020693 | 2.669351733 | 2.36395771 | 1.910609499 |
| 261 | 1.978618006 | 2.732613301 | 2.19594212 | 1.683156477 |
| 263 | 1.350274014 | −0.59210334 | 0.14780643 | −0.13113746 |
| 264 | 0.526085484 | −1.54983116 | −0.17497208 | −0.8204696 |
| 267 | 1.175997006 | −1.03507906 | −0.11004734 | −0.50564806 |
| 269 | 2.367197222 | 0.457286256 | 0.02211231 | 0.497925297 |
| 270 | 0.711734628 | −1.45058685 | −0.17018094 | −0.71795736 |
| 271 | 1.073564668 | −0.47951936 | −0.80269361 | 0.136837431 |
| 273 | 0.663835001 | −1.5674675 | 0.28509522 | −1.12959038 |
| 274 | 1.628173498 | −0.58892922 | −0.3892777 | −0.66728139 |
| 275 | 0.935336765 | −0.9522644 | −0.87000279 | −0.29365972 |
| 276 | −5.989155804 | 1.722071272 | 3.31094703 | 1.273171428 |
| 277 | 0.904631703 | −1.02628534 | 0.49274649 | 1.000655271 |
| 278 | 0.293923493 | −0.82335619 | 0.13147975 | 2.730914048 |
| 280 | −0.284822555 | 0.322094188 | 3.2184015 | 0.383213731 |
| 281 | 2.201373139 | 2.228820089 | 2.03455575 | 1.720697243 |
| 282 | 0.505189899 | −1.01844885 | −0.98499144 | 0.912195522 |
| 283 | 0.775002479 | −1.29876341 | −1.52162214 | −0.77292581 |
| 284 | 0.505189899 | −0.57830662 | −0.55673047 | −1.09870665 |
| 285 | −0.987611415 | 0.908212704 | 2.59089199 | 1.311154128 |
| 286 | −2.635687733 | −1.53554173 | 0.68132558 | 4.350511118 |
| 287 | −1.890800496 | −0.9175912 | −0.84177071 | 0.615422874 |
| 288 | −0.417807714 | −0.27643667 | 1.06515025 | 0.958812195 |
| 289 | 1.078763544 | 0.263281029 | 1.00763749 | 0.866949263 |
| 290 | 0.733561298 | −0.47493387 | 0.17088582 | 1.536463653 |
| 292 | 1.2252731 | 0.720498276 | 4.33362953 | 2.202084022 |
| 293 | 0.947860369 | 0.93449449 | 1.85056304 | 0.355024738 |
| 294 | −1.051634009 | 0.136579632 | 2.17918871 | −0.01949057 |
| 295 | 1.039790111 | 0.81471915 | −0.94326824 | 0.887662055 |
| 296 | 1.009509413 | 1.364418947 | 1.42805339 | 0.429992055 |
| 300 | 0.246930208 | 1.113809101 | 0.25540773 | 0.528760053 |
| 301 | 0.246930208 | 1.113809101 | 0.25540773 | 0.528760053 |
| 302 | 0.697198045 | −0.41500676 | −2.35076003 | −0.60639529 |
| 303 | 0.10667178 | 3.580489288 | 0.25893587 | 2.329367856 |
| 306 | 0.561360663 | −0.17793966 | −1.63250554 | −0.7564969 |
| 307 | 1.583243229 | 1.398558046 | 0.152423 | −0.13988304 |
| 308 | −0.067380931 | 0.74278658 | 0.29217479 | 0.180866298 |

-continued

| Material No. | MORV value for Equation a.) | MORV Value for Equation b.) | MORV Value for Equation c.) | MORV value for Equation d.) |
|---|---|---|---|---|
| 310 | 0.238202662 | 0.926241567 | −0.66649303 | 0.508184193 |
| 312 | 0.714965519 | −0.45511207 | −2.34849436 | −0.9953911 |
| 314 | 0.736369931 | −0.52068396 | 0.53882253 | −0.7059813 |
| 316 | 2.314558863 | −0.25458611 | 0.22080129 | −0.04142716 |
| 317 | 1.095005005 | 0.057439852 | −1.20728654 | 0.035895107 |
| 318 | −0.111714595 | −0.61079351 | −1.16010053 | 1.102488007 |
| 319 | −0.264829849 | 0.540388888 | 0.10729709 | −0.57215449 |
| 321 | 1.243861203 | −0.75229123 | 0.05515858 | −0.34659253 |
| 322 | 0.956379568 | 2.838565742 | 2.7997689 | 0.805938034 |
| 323 | 1.884902746 | 0.813499245 | 0.86344403 | −0.1241887 |
| 324 | 0.189037208 | 1.105600415 | 0.48460989 | 0.285938173 |
| 325 | 0.791400443 | 2.454239197 | 1.54315324 | 1.416449646 |
| 328 | 1.22836182 | 2.190068443 | 2.48751772 | 0.126982574 |
| 329 | 1.800767509 | 1.372656013 | 2.09551175 | 2.849728342 |
| 330 | 2.688999059 | 0.017422444 | 0.34929031 | 0.108155361 |
| 331 | −0.223648429 | 0.873635097 | 1.78683863 | 0.126324441 |
| 332 | 1.884902746 | −0.46695445 | 0.1761545 | −0.11026722 |
| 333 | 0.956379568 | 2.838565742 | 2.7997689 | 0.805938034 |
| 334 | 0.569368001 | 2.811464091 | 1.88866785 | −0.16122533 |
| 335 | 1.931053264 | 2.306571877 | 4.45651797 | 4.474221307 |
| 336 | 1.355107839 | −0.49142588 | 0.83879083 | 0.18350392 |
| 338 | 1.025467157 | −0.99345477 | 0.57780149 | −0.19101275 |
| 339 | 1.216559787 | −0.68632827 | 0.71921804 | 0.140021721 |
| 342 | 2.073599715 | −0.19777074 | −0.44964804 | −0.71885866 |
| 343 | 3.375840967 | 3.294907583 | 5.0378352 | 4.14804591 |
| 344 | 0.926453735 | 1.336260845 | 2.20088072 | 0.226359561 |
| 346 | −0.133453942 | −0.27276578 | 0.95852923 | −0.88404805 |
| 347 | −0.414858428 | −0.94736055 | 1.9452074 | −1.32753709 |
| 349 | 0.011110326 | 0.415952358 | 1.08076289 | 2.638925816 |
| 350 | −1.366284701 | −1.3912958 | −0.0683659 | 1.205395618 |
| 352 | 2.592229701 | 2.014162407 | −0.56599991 | −0.19676404 |
| 353 | 2.347680291 | 1.432589328 | 3.81650185 | 2.28664738 |
| 354 | −0.094599823 | 0.704257624 | 0.8494127 | −0.05632553 |
| 355 | −0.534528735 | −0.26820008 | 0.69328667 | 0.63557685 |
| 356 | 0.71431796 | 0.568464069 | 1.14931631 | 0.32594963 |
| 358 | 1.637857828 | 1.932629993 | 0.68535871 | −1.06298922 |
| 359 | 3.169264285 | 2.326146291 | 5.44251947 | 3.621423972 |
| 360 | 2.824830639 | 3.29829616 | 3.43870859 | 3.771256974 |
| 361 | 0.772183137 | 0.62924397 | 1.14549597 | 0.743423792 |
| 362 | 2.158106604 | −0.08901432 | 0.85035629 | −0.37323677 |
| 363 | 1.485114303 | −0.85819594 | 0.70929196 | 4.132013298 |
| 364 | −0.661168364 | −0.30270875 | 2.49237859 | −0.7675819 |
| 365 | −0.518303431 | −2.08665423 | 0.5658944 | −1.10451499 |
| 366 | −0.501301831 | 0.561788544 | 0.14113617 | 0.610082057 |
| 368 | −0.106125097 | 1.092782715 | −0.89571841 | −0.08594454 |
| 369 | 1.43532227 | 1.656262941 | −1.09448841 | 1.674272267 |
| 370 | 1.064083705 | −1.08482967 | 0.35640283 | 0.866246621 |
| 371 | 1.933819902 | 0.975863726 | 1.62799441 | 1.492919426 |
| 372 | 1.933819902 | 0.975863726 | 1.62799441 | 1.492919426 |
| 373 | 0.274120553 | 2.246646022 | 2.93946992 | 2.617412085 |
| 374 | 0.940949346 | 2.935858163 | 0.52084392 | 0.847114052 |
| 375 | 0.177236108 | 2.745061961 | 0.76268843 | 0.373809692 |
| 376 | −0.999571921 | 0.579320229 | −0.06019938 | −0.94280945 |
| 377 | 0.521811983 | −0.8476641 | 0.7732327 | 1.729406547 |
| 378 | −0.532701772 | −2.17823188 | 1.26760147 | 0.815211357 |
| 379 | −0.684994963 | 0.018353057 | −0.8170018 | 0.582030709 |
| 381 | 1.592237677 | 1.373054134 | 0.60184939 | −0.30300485 |
| 385 | 0.967501839 | 0.136172137 | 1.3645564 | 0.374341215 |
| 385 | 0.967501839 | 0.136172137 | 1.3645564 | 0.374341215 |
| 386 | 1.247138794 | −0.97883463 | 0.03688288 | −0.57321578 |
| 387 | 0.785485559 | −1.23629818 | −0.07759084 | −0.71795736 |
| 388 | 1.503632155 | −0.13455265 | 0.86630165 | 0.102845335 |
| 388 | 1.503632155 | −0.13455265 | 0.86630165 | 0.102845335 |
| 390 | 0.811363694 | 0.872605919 | −0.17445198 | 1.358866557 |
| 391 | 1.653006495 | −0.44095837 | 0.46475017 | −0.16817306 |
| 394 | 1.043989895 | −0.82625074 | 0.40893134 | −0.10417542 |
| 397 | 1.430046723 | −0.79407262 | 0.15684862 | −0.4384694 |
| 398 | −1.401723491 | 0.271079592 | 1.35530191 | −0.63550333 |
| 400 | 0.762211626 | −1.06778628 | −0.93642574 | −0.13193338 |
| 407 | 0.591198428 | −0.8943503 | 1.41392426 | 2.694863328 |
| 412 | −0.067309295 | −0.21963004 | 0.57788677 | −1.22740398 |
| 413 | 0.630456164 | 1.538096427 | 2.10994563 | 2.45668637 |
| 414 | 0.460631327 | 3.678501689 | 1.18326431 | 1.28320952 |
| 415 | 0.060485009 | −1.37776759 | −0.22689728 | 2.328813337 |
| 416 | 1.864088631 | 0.2451067 | 1.63260125 | 1.855346924 |

-continued

| Material No. | MORV value for Equation a.) | MORV Value for Equation b.) | MORV Value for Equation c.) | MORV value for Equation d.) |
|---|---|---|---|---|
| 417 | −0.747017264 | −2.60335412 | 0.85092701 | 3.525229717 |
| 418 | 3.678359573 | 3.437930194 | 4.42449746 | 0.716864637 |
| 419 | −0.131519393 | 0.731836014 | 0.81604919 | −1.29993979 |
| 420 | 0.11276779 | −0.13029453 | 0.19422843 | 0.853490939 |
| 421 | 2.819997124 | 0.193567405 | 1.15903162 | 1.748390255 |
| 424 | −0.211768579 | 1.46336231 | −0.93580247 | −1.48749449 |
| 425 | −1.467980751 | −2.41196874 | −0.34454968 | 2.161517022 |
| 426 | 2.176374648 | 2.131594325 | 1.99252316 | 0.002774099 |
| 428 | 2.10568799 | 0.336366154 | −1.41176883 | 0.827982605 |
| 429 | 2.179080731 | 0.811454228 | −0.58304782 | 0.827982605 |
| 432 | 0.814675557 | −0.13076033 | 1.07380397 | −0.01560954 |
| 436 | 0.003614069 | −0.4704298 | 1.6004974 | −1.27605297 |
| 437 | −0.070955783 | −0.17246926 | 0.32599434 | 0.682083059 |
| 438 | 0.71141055 | −0.62729405 | 0.6220964 | 0.498836975 |
| 439 | −2.152188932 | −1.81662702 | 0.66042162 | −1.57001886 |
| 440 | 0.194444196 | 0.880854446 | 0.80016905 | 0.373809692 |
| 441 | 2.349282571 | 1.734747324 | 1.71148239 | 1.274963632 |
| 442 | 0.243841724 | 0.036287037 | 0.51243015 | 0.361825534 |
| 443 | −0.131519393 | 0.731836014 | 0.81604919 | −1.29993979 |
| 444 | 0.607958335 | 1.910541857 | −0.42710132 | −0.46909656 |
| 445 | −0.047486491 | 1.045012945 | −0.25220201 | −0.31982826 |
| 447 | 0.611981677 | 0.559261438 | −0.31210071 | −2.20421695 |
| 448 | 0.45491409 | 0.804084437 | 0.03088748 | −0.17549737 |
| 449 | 0.323968221 | −1.00428076 | −1.65151616 | 1.031096548 |
| 450 | 1.433196296 | −0.12277841 | 3.46809784 | −0.14760118 |
| 453 | 1.138642907 | 0.238344138 | −0.56453732 | −0.60639529 |
| 454 | 0.689556954 | −0.32116049 | 0.17614165 | 0.99165159 |
| 455 | −0.978653338 | −0.96381951 | 0.37950282 | 0.793341469 |
| 457 | 2.740852074 | 1.146976436 | 0.01429902 | 0.909817098 |
| 459 | 2.034203389 | −0.06483391 | 0.25864307 | 0.096715771 |
| 461 | 0.405441454 | 3.029508918 | 1.66201629 | 0.621375526 |
| 462 | 1.348588872 | 2.252065606 | 1.98535615 | 0.126982574 |
| 463 | 2.402548765 | 0.141297665 | 0.32401564 | 0.165555831 |
| 464 | 1.396358739 | −0.35292634 | 0.11760582 | −0.13960954 |
| 465 | 0.940569103 | 1.267891616 | 1.68420132 | 1.263608034 |
| 466 | −0.191220659 | 0.067062979 | 2.24237992 | 0.125280183 |
| 467 | 0.940569103 | 1.267891616 | 1.68420132 | 1.263608034 |
| 468 | 0.123370943 | 1.164309475 | 0.17099727 | −0.95446701 |
| 469 | 0.925252053 | −0.57178441 | 0.69807561 | −0.59133195 |
| 470 | 2.237616041 | 1.810156128 | −0.58140154 | 1.320304914 |
| 471 | 1.714516544 | −0.62135116 | 0.23636624 | −0.2706853 |
| 472 | 0.605628283 | 0.938001104 | 0.50028363 | 0.743911872 |
| 473 | 0.093847515 | −1.1973016 | −0.26960381 | 1.829684619 |
| 474 | 0.696773849 | 1.065592689 | 0.37607733 | −0.19214193 |
| 475 | 1.405352842 | 0.379589036 | 0.27781476 | 0.041425889 |
| 477 | 0.237582954 | 0.629327199 | 0.45159895 | −1.59912382 |
| 478 | 1.360648836 | 0.598053217 | 2.00883441 | −0.0827715 |
| 479 | 2.214928637 | −0.24358938 | −0.3486103 | 0.9190125 |
| 480 | 1.933819902 | −0.3826187 | 0.97439148 | 1.491603428 |
| 480 | 1.933819902 | −0.3826187 | 0.97439148 | 1.491603428 |
| 481 | 0.612364301 | −0.26364231 | −1.3201026 | −1.62884377 |
| 482 | 1.604448424 | 1.286308964 | −0.34289284 | 0.887781648 |
| 482 | 1.604448424 | 1.286308964 | −0.34289284 | 0.887781648 |
| 484 | 3.269313083 | 2.336715633 | 3.65534824 | 2.158890088 |
| 486 | 1.530484593 | 1.052491466 | 3.11297562 | 0.430146348 |
| 487 | 2.889323404 | 2.226094104 | 4.12877599 | 2.184426542 |
| 488 | 1.062548487 | 4.75312035 | 2.78435853 | 2.01925207 |
| 491 | 0.397432667 | −0.20071274 | 0.842202 | 1.944142408 |
| 493 | 0.270731661 | −0.7406408 | −1.17192239 | 1.401933582 |
| 495 | 0.298981649 | 0.854414067 | −2.2714622 | −0.62848261 |
| 496 | 0.565278409 | 0.659352661 | −0.00159534 | 0.384991859 |
| 497 | 2.972647554 | 1.210988046 | 0.08629653 | 0.991649406 |
| 498 | 2.863652137 | 0.229707592 | −0.75515466 | −0.06022029 |
| 502 | 0.478208715 | 1.827989577 | 0.67676345 | −0.88328385 |
| 503 | 0.845706083 | 1.117392544 | −0.21773539 | 0.272770415 |
| 504 | 0.837488879 | 0.874463134 | −0.08311625 | 0.149327397 |
| 505 | 1.749446006 | 0.076054765 | −0.59137073 | 0.291488011 |
| 509 | 0.716903285 | −0.22917288 | −1.93027881 | −1.52173529 |
| 510 | 0.241638743 | 0.769444787 | −0.07283731 | −0.38771737 |
| 512 | 0.556069536 | −0.47514685 | −1.88388474 | −1.67297277 |
| 515 | 0.23291131 | 0.598998195 | −0.99553291 | −0.40829542 |
| 517 | 0.784181146 | −0.20530019 | −1.89414748 | 0.152726109 |
| 518 | 0.742030255 | 0.281479436 | −1.4156326 | −1.91369695 |
| 519 | 0.367442761 | −0.50911405 | −0.77651804 | 3.081125259 |
| 520 | 1.28335174 | −0.16976166 | 0.19676128 | 1.493753388 |

-continued

| Material No. | MORV value for Equation a.) | MORV Value for Equation b.) | MORV Value for Equation c.) | MORV value for Equation d.) |
|---|---|---|---|---|
| 521 | −1.105672292 | −1.29204085 | −0.95149628 | 1.817322011 |
| 522 | 0.714965519 | −0.45511207 | −2.34849436 | −0.9953911 |
| 524 | 0.325255266 | 1.131242708 | −2.79377204 | −0.62848261 |
| 525 | −0.210625832 | 0.979060885 | 0.37926876 | −2.08002977 |
| 526 | 0.698504484 | 0.548193178 | 0.92265651 | 0.500152973 |
| 527 | 0.420012766 | 1.731459464 | −0.23341719 | 0.139565409 |
| 528 | 0.161304111 | 0.66712144 | 0.58401752 | 0.373809692 |
| 529 | 0.911890585 | 0.353572744 | 1.04706167 | 1.001090055 |
| 530 | 1.670680003 | 0.86138741 | −0.27652639 | 1.174059185 |
| 531 | −0.169223695 | 1.172917966 | −0.11306441 | 0.099121666 |
| 532 | 2.237616041 | 1.438074134 | 0.31117554 | −0.71786492 |
| 534 | 1.205873658 | 1.32208026 | 1.21816392 | −0.5027271 |
| 535 | 0.999469738 | 0.056406435 | 0.72382479 | −0.61170287 |
| 536 | 0.63876931 | −0.39111525 | 0.08747854 | −0.66833729 |
| 537 | 0.689953348 | 1.206425159 | 0.58870271 | 0.198159994 |
| 538 | 0.54988634 | −0.32842011 | 0.69258273 | −0.81953404 |
| 540 | 0.735538933 | −0.20826876 | 0.6955468 | −0.7170218 |
| 541 | 1.097368973 | 0.740159871 | 0.12012053 | 0.137772993 |
| 542 | −0.24632881 | −0.09354384 | −0.13580399 | 0.599029186 |
| 544 | 0.687639306 | −0.30861817 | 1.14537443 | −1.12865481 |
| 546 | 1.670680003 | 1.94609957 | 0.19633838 | 1.14825764 |
| 547 | −0.24632881 | −0.23975349 | −0.01449288 | 0.574861147 |
| 548 | 1.349418105 | −0.29885837 | 0.42849141 | 0.008671721 |
| 549 | 0.623933699 | −0.62776258 | −1.2835205 | −0.23131507 |
| 550 | 1.091300413 | −0.33969057 | 0.91994098 | 0.043900994 |
| 550 | 1.091300413 | −0.33969057 | 0.91994098 | 0.043900994 |
| 551 | 1.172668936 | −0.39476924 | −0.61394794 | −0.16425167 |
| 552 | 1.434150355 | 1.041294025 | 0.32000606 | 1.24279868 |
| 553 | 1.040907688 | −0.38050079 | −0.95306497 | −0.03036668 |
| 554 | 0.623933699 | −0.65991007 | −1.27562979 | −0.61529805 |
| 555 | 0.623933699 | −0.09654208 | −0.6432411 | 1.36608372 |
| 556 | 0.623933699 | −0.62776258 | −1.2835205 | −0.23131507 |
| 557 | −1.043779684 | 0.358151507 | 0.96578333 | −0.7498558 |
| 558 | 3.113548387 | 0.901949497 | −0.07402944 | 2.171129217 |
| 559 | 1.433732801 | 2.854621121 | 1.81079379 | 0.893806123 |
| 560 | 0.793851811 | 0.195900744 | 1.13222828 | −0.38432626 |
| 561 | 1.874725149 | 0.921395625 | 3.05642524 | 2.616508159 |
| 562 | −1.30410643 | −2.63450231 | 0.12574616 | 1.001870337 |
| 563 | −0.153585698 | 2.733591064 | 2.12854196 | 3.424603045 |
| 565 | 3.655479783 | 3.751479035 | 5.51820797 | 3.282822615 |
| 566 | 4.034374094 | 3.755759834 | 4.82506006 | 3.190861648 |
| 567 | 4.203811008 | 3.627632534 | 4.68751919 | 3.372829008 |
| 568 | 1.643514525 | 0.827299302 | 0.70706274 | 2.545428997 |
| 569 | 2.692371513 | 3.589810155 | 4.40390088 | 4.506937878 |
| 570 | 1.707556133 | 2.400065573 | 1.78745169 | 2.655458557 |
| 571 | 1.862893827 | 2.803280605 | 0.98209954 | 3.188564781 |
| 572 | 1.203581368 | 0.798608763 | 2.67898788 | 1.659633314 |
| 573 | 2.459623568 | 2.656773866 | 3.54771795 | 2.085649266 |
| 574 | 2.878405284 | 1.770500246 | 4.00464111 | 4.859737959 |
| 575 | −0.395731956 | 0.325594009 | 0.98982713 | −0.25791379 |
| 576 | −0.2346025 | 0.890438549 | −0.13206526 | −0.83961838 |
| 577 | 0.484934913 | 2.001798597 | −0.11430063 | −0.05230593 |
| 578 | 1.138642907 | −0.72228381 | −1.0321 | −0.60639529 |
| 579 | −2.722013313 | −3.79238321 | −1.13572295 | 0.953543134 |
| 580 | 1.138642907 | −0.66601616 | −0.95089973 | 1.036450105 |
| 581 | 1.105119249 | −0.82090309 | −0.06184517 | −0.90904158 |
| 582 | 2.092976965 | −0.31228784 | 0.08755137 | −0.62955362 |
| 583 | −0.24632881 | −1.33540368 | −0.96483147 | 0.624830731 |
| 584 | 2.237616041 | 0.30800753 | −0.44296441 | −0.71918014 |
| 585 | 0.634021669 | −0.28724544 | −0.74527157 | −1.361765 |
| 586 | 1.313957377 | 0.449601 | 1.50810166 | −0.30998322 |
| 587 | 0.304876136 | −0.43283205 | 1.23096012 | 0.398961811 |
| 588 | 0.449793066 | 0.007950225 | 0.8004147 | −0.63434071 |
| 589 | −0.681766404 | 1.08547116 | 0.54331319 | −2.16710754 |
| 591 | −0.34676031 | −0.77573166 | 1.85884084 | 0.312272735 |
| 592 | −1.573190219 | 2.29028194 | 1.86285367 | 0.687279186 |
| 594 | −1.45374647 | 0.452156392 | 2.48970747 | 0.858468114 |
| 595 | 0.058003677 | −1.91126878 | 1.52586392 | −0.07528071 |
| 599 | 1.485777974 | 1.54384772 | 0.79002365 | −0.09069773 |
| 600 | 1.914093549 | 0.841364523 | 0.15173954 | 0.255445859 |
| 601 | 1.203870517 | 1.17864533 | 1.22686262 | 0.453935114 |
| 602 | 0.771984982 | 0.66859171 | −0.37427136 | 0.07599515 |
| 603 | 3.218950175 | 1.464118271 | 2.47512497 | 1.214429025 |
| 604 | 2.710087358 | 1.517756148 | 0.35088855 | 0.603171932 |
| 605 | 0.703615734 | 0.42129186 | 0.39567696 | 0.41729786 |

-continued

| Material No. | MORV value for Equation a.) | MORV Value for Equation b.) | MORV Value for Equation c.) | MORV value for Equation d.) |
|---|---|---|---|---|
| 606 | 0.055463315 | 1.972687323 | 3.42898264 | 1.395457482 |
| 607 | −0.146397553 | −2.05649732 | 0.17598641 | 1.900931587 |
| 608 | 1.473771668 | 2.08260463 | −1.09319437 | 0.44289209 |
| 609 | −0.466215117 | 0.845009196 | 1.89800228 | 0.840292062 |
| 610 | 2.14236439 | 1.079695535 | 0.29060257 | 1.329215628 |
| 611 | 1.078583502 | 1.707732184 | −0.73721672 | −0.87923138 |
| 612 | −0.128136098 | 1.038320983 | −0.63703066 | 0.184527669 |
| 613 | 1.599427115 | 3.615521066 | 0.43343413 | −0.1515479 |
| 614 | 1.489603514 | 2.706865637 | −0.06242639 | −0.47244791 |
| 615 | 1.960664614 | 4.490550162 | 2.26962278 | 0.346542121 |
| 616 | 2.689328335 | 3.692579375 | 2.01499213 | 1.348800283 |
| 617 | −0.845027889 | 0.504788036 | 0.4957383 | −0.65628324 |
| 618 | −0.461016335 | 1.612995126 | 1.09551709 | −1.62235977 |
| 619 | −0.222804396 | 0.361727974 | 0.62743416 | −1.02982449 |
| 620 | 0.745610019 | −0.76737462 | −0.67364137 | 1.696394301 |
| 621 | 3.671429366 | 1.708460032 | 4.57083156 | 1.955988764 |
| 624 | 2.139270802 | 2.093130621 | 2.5533383 | 3.30383102 |
| 625 | 0.665423108 | 1.356936283 | 1.5515704 | 1.874119646 |
| 626 | 1.292942787 | 0.621140137 | 2.28513785 | 1.042322574 |
| 627 | 1.14724223 | −0.51104438 | 1.01088446 | 1.51232276 |
| 628 | 1.44418619 | 3.825155203 | −0.84341678 | −0.02251455 |
| 631 | 2.622138509 | 5.106659136 | 4.48303003 | 2.115425367 |
| 632 | 2.450328692 | 4.670297017 | 4.54579766 | 2.15781135 |
| 633 | 1.560465308 | 2.636096631 | 2.45546606 | 0.920962489 |
| 635 | 1.510161132 | 2.388971583 | −0.63579931 | 1.939575919 |
| 636 | 1.433842763 | 0.529693203 | −0.23195491 | 1.22356734 |
| 638 | 1.921725015 | 0.758255259 | 0.81570609 | 3.615611357 |
| 639 | 0.422001837 | −0.14885323 | −0.00660617 | 1.726576493 |
| 640 | 0.865825265 | −0.28827025 | −0.54129473 | 0.283616979 |
| 641 | 0.813978315 | 0.509726232 | 0.37457254 | 0.842075065 |
| 644 | 0.85173251 | 0.664325682 | 1.88299246 | 0.951603698 |
| 645 | 0.417907652 | −1.00347186 | 0.9667556 | −0.47157656 |
| 647 | 0.221569324 | −1.2239438 | 0.91464498 | −0.19166679 |
| 649 | −0.560315649 | −0.67419393 | −0.02482011 | 1.492767049 |
| 650 | 1.640396187 | 0.328871961 | 0.04729888 | 0.912259803 |
| 651 | 0.672555558 | −0.9987845 | 0.48545476 | −0.13530683 |
| 652 | −0.995969271 | −1.38653208 | −0.49268035 | 0.944524468 |
| 653 | 1.203949791 | 0.0153333 | −0.10401424 | 0.73323846 |
| 655 | 1.334772083 | 0.418728831 | −0.92221842 | 1.317365259 |
| 658 | 0.414934548 | 0.314990682 | 2.78051829 | 2.656854539 |
| 659 | 3.996948911 | 1.915319951 | 3.03990612 | 5.764113617 |
| 660 | 2.175041013 | 1.882945358 | 0.07779745 | −0.18323732 |
| 661 | −0.316755016 | 1.64607349 | 2.76327471 | 2.024910676 |
| 662 | 0.258228842 | 0.844792644 | 0.1924797 | 0.098776211 |
| 663 | 1.521826905 | 1.097809988 | 2.13583044 | 1.30609234 |
| 664 | 0.708920214 | −0.27795513 | 0.15395433 | 0.014791904 |
| 665 | 0.630772742 | −0.34278374 | 0.49097281 | −0.0565644 |
| 667 | 0.812238101 | 0.195908668 | 0.21564664 | 0.219336109 |
| 668 | 1.529097453 | 2.246515706 | 1.4678099 | −0.81836944 |
| 671 | 1.453855457 | −0.51177209 | −0.78608937 | 0.361715513 |
| 672 | 0.771613806 | −0.81209599 | −0.85297613 | 0.084880782 |
| 673 | 1.874725149 | 0.921395625 | 3.05642524 | 2.616508159 |
| 674 | 5.912391366 | 3.468705262 | 6.81994671 | 7.217631788 |
| 675 | 0.525794155 | 0.473286101 | 2.51749677 | 2.935001452 |
| 676 | 0.623704257 | 1.523736626 | 2.50208859 | 2.474137331 |
| 677 | −0.548848405 | 0.058004962 | 1.07849806 | 2.361730638 |
| 678 | 4.818555677 | 1.506257638 | 4.96635528 | 5.508133385 |
| 679 | 4.332202737 | 2.699343437 | 5.65576391 | 5.021298111 |
| 680 | 4.042984412 | 4.75506829 | 4.65903898 | 4.913020939 |
| 681 | 0.5959536 | 2.091803965 | −0.14697928 | −0.71889234 |
| 683 | 0.87899671 | 0.043210589 | 1.37554648 | −0.60198897 |
| 684 | 2.349844428 | 1.181400632 | 2.15359469 | 2.136987013 |
| 686 | 1.024635336 | 1.040500794 | 0.9820242 | −1.16405004 |
| 687 | 0.551495677 | 0.66297128 | −0.45433071 | −1.28827912 |
| 691 | 1.609835015 | 2.898881191 | −0.99203246 | −0.15162554 |
| 692 | 2.002379485 | 3.95875961 | 1.1705779 | 0.346542121 |
| 693 | 4.264631423 | 4.375626605 | 0.93418004 | 0.114988571 |
| 693 | 4.264631423 | 4.375626605 | 0.93418004 | 0.114988571 |
| 694 | 4.858313721 | 4.772826468 | 3.58732214 | 2.558402204 |
| 696 | 2.99409154 | 3.843066736 | 2.50597637 | 1.205022789 |
| 697 | 0.407534444 | 2.829113684 | 2.16548165 | 0.756766079 |
| 698 | 0.983060431 | 2.328872529 | 1.67788951 | 0.805938034 |
| 699 | 0.996500165 | 0.60129571 | −0.27496491 | −0.22179967 |
| 700 | 0.698400489 | 0.514637899 | 1.14265307 | 0.816064314 |
| 701 | 0.592372435 | −0.67812322 | −1.75051912 | −0.51109618 |

-continued

| Material No. | MORV value for Equation a.) | MORV Value for Equation b.) | MORV Value for Equation c.) | MORV value for Equation d.) |
|---|---|---|---|---|
| 702 | −0.211768579 | 1.46336231 | −0.93580247 | −1.48749449 |
| 703 | 0.372029303 | 0.866016277 | −0.91679974 | 0.347054507 |
| 704 | 1.187861135 | 0.858978871 | 0.1265005 | 0.217668671 |
| 706 | 0.193569186 | 1.623921627 | 0.08867618 | 0.808617424 |
| 707 | 0.819562098 | 3.57840156 | 3.38080377 | 1.26599216 |
| 708 | 2.391828225 | 1.877690145 | 3.85935427 | 1.647356195 |
| 709 | 1.280902077 | 2.17019575 | 3.40315777 | 0.126982574 |
| 710 | 1.454593977 | 3.128186882 | −2.26368122 | −0.02251455 |
| 711 | −0.783387499 | 1.465620573 | 1.22912535 | −1.41213701 |
| 712 | 1.936489942 | 2.528373237 | 2.13424487 | 2.393940425 |
| 713 | 1.303999908 | 2.146563611 | −0.26420591 | −0.01477791 |
| 714 | 2.3584433 | 3.778880151 | 3.4396901 | 1.593719007 |
| 715 | 4.023918591 | 3.403899942 | 5.07447567 | 4.880181625 |
| 716 | 0.981194248 | 1.73892162 | 2.21166953 | 2.738129365 |
| 717 | 0.983060431 | 2.328872529 | 1.67788951 | 0.805938034 |
| 718 | 1.241840746 | 3.430871861 | 0.55000978 | 1.073616332 |
| 719 | 1.483275952 | 3.037398628 | −1.55547275 | −0.47244791 |
| 720 | 2.372311412 | 3.403234423 | −0.21191089 | −0.08519829 |
| 721 | 2.128185431 | 0.274654772 | 0.47626043 | 2.465333527 |
| 722 | 0.616377169 | −0.58753328 | 0.48821573 | 1.063402884 |
| 723 | −1.273274319 | −1.12897478 | 1.71118519 | 4.067480158 |
| 724 | 2.103515193 | 0.165377929 | −0.18223896 | 0.288303217 |
| 725 | 0.983060431 | 2.328872529 | 1.67788951 | 0.805938034 |
| 726 | 2.887615733 | 3.282342953 | 1.95034945 | 2.462290186 |
| 727 | 2.241052707 | 2.13951389 | 0.36814978 | 0.371689426 |
| 730 | 1.121105724 | −0.20397307 | −0.15741334 | 0.897609916 |
| 731 | 1.437838545 | −0.09620743 | 0.02756967 | 1.949139525 |
| 733 | −0.46922259 | 1.067777032 | 1.61226345 | 0.185415155 |
| 735 | −0.081273581 | 1.192925027 | 1.67970188 | 0.33874614 |
| 736 | −0.13000788 | 1.099012031 | 1.64139691 | 0.248287146 |
| 738 | 1.670680003 | −0.20756775 | −0.73755051 | −0.84924056 |
| 740 | −1.532691904 | −2.55214711 | 0.57438104 | 0.555698696 |
| 741 | 1.407504561 | 0.048284736 | 1.01405149 | −2.2579901 |
| 742 | 0.644803847 | 0.644647752 | 1.35192052 | −0.62780087 |
| 743 | 0.174679072 | 0.169515693 | 0.62350977 | −0.08144308 |
| 744 | 0.02068385 | 0.648730454 | −0.04946215 | 0.214634634 |
| 745 | 0.741424752 | 0.523647641 | 0.52863925 | −0.65426285 |
| 746 | 1.285306965 | 1.929408375 | 0.85560877 | −1.4619958 |
| 748 | −1.513804897 | −1.10823383 | 1.09397284 | −0.88975989 |
| 750 | 2.554017714 | 3.544542579 | 4.42317523 | 1.647356195 |
| 752 | 2.592229701 | 1.158945916 | 0.24149847 | −0.58379051 |
| 754 | 1.649506181 | 1.31981993 | 2.36997533 | 0.406081966 |
| 755 | −0.028552173 | 0.253838465 | 0.95694896 | −0.16565786 |
| 757 | 1.446915042 | 0.673406021 | −0.6641103 | −1.80002119 |
| 758 | 5.933043009 | 5.716461604 | 6.67410554 | 4.433272782 |
| 760 | −3.195604514 | −2.60998376 | −0.11222221 | 0.792186468 |
| 761 | 0.286783044 | −0.52414055 | −0.57593161 | 0.628896611 |
| 763 | 1.405567948 | −0.84372738 | −1.32379279 | −0.50314577 |
| 766 | 0.279442569 | −1.00722191 | −0.18524031 | 2.487147765 |
| 767 | −1.32777782 | −2.36136561 | −0.79602501 | 1.247063893 |
| 768 | −0.692560954 | −1.92177717 | 0.46687554 | 2.400762497 |
| 769 | 1.889999468 | 1.112266205 | 0.82815523 | 0.525271623 |
| 770 | 2.237616041 | 2.282141767 | −0.149966 | −0.71866539 |
| 771 | 0.909356011 | 0.368597887 | 1.03689838 | 1.001198751 |
| 772 | 1.328601831 | 0.715296776 | 0.20358825 | 1.147403521 |
| 774 | 2.002379485 | 3.95875961 | 1.1705779 | 0.346542121 |
| 775 | 1.936489942 | 2.528373237 | 2.13424487 | 2.393940425 |
| 776 | 1.495019673 | 4.35984375 | 2.59969954 | 2.95313487 |
| 777 | 0.206892499 | −0.57813502 | −0.32983 | 0.781221286 |
| 778 | 1.340232187 | −0.11034804 | 0.35759778 | 1.690582999 |
| 779 | 0.595257521 | −0.85639987 | 0.19436224 | −0.73333902 |
| 781 | 2.187955186 | 2.571774369 | 2.74817529 | −0.52827851 |
| 782 | 0.893855657 | 0.63313304 | 1.19104388 | −1.61620514 |
| 784 | −0.275919571 | −1.64491584 | 0.60429762 | −1.5580623 |
| 786 | −0.043537347 | 1.337721065 | −0.56551398 | −0.02167052 |
| 788 | 2.147983695 | 1.250042565 | 1.72576392 | 1.626956379 |
| 789 | −0.624451013 | 0.76248127 | −0.79219481 | −0.73513092 |
| 791 | 0.227060873 | −0.04783658 | −0.16862915 | 1.166609659 |
| 792 | 0.90746622 | 1.643598677 | 0.26467094 | 0.396081003 |
| 796 | 0.811374104 | 0.766579899 | 0.10161642 | 0.135186519 |
| 797 | −0.185638022 | 0.53853264 | 0.65441562 | −0.25681926 |
| 799 | 0.657769581 | 0.095543194 | 0.89522656 | 0.558428618 |
| 800 | 0.227060873 | −0.04783658 | −0.16862915 | 1.166609659 |
| 802 | −0.660595577 | 1.597474466 | 1.49106895 | −0.20429128 |
| 803 | 1.706162052 | 0.623892414 | 0.59662073 | 0.7745661 |

-continued

| Material No. | MORV value for Equation a.) | MORV Value for Equation b.) | MORV Value for Equation c.) | MORV value for Equation d.) |
|---|---|---|---|---|
| 804 | 3.478490379 | 2.348697011 | 3.96279011 | 2.456963386 |
| 805 | 0.377241729 | 0.83329773 | 0.1712741 | 1.057125999 |
| 806 | 2.863652137 | 0.771287371 | −0.4183972 | −0.44551461 |
| 807 | 1.794279084 | 0.711717977 | 0.35187068 | −1.0208486 |
| 808 | 0.408210632 | 0.633556897 | −0.37022584 | 0.717270748 |
| 810 | −2.506277966 | −2.61703099 | 0.87880054 | −0.72832121 |
| 811 | −0.789075789 | −0.15346024 | 0.64720487 | −0.48507671 |
| 812 | −1.395132583 | −2.59063834 | 0.14973761 | 0.623759794 |
| 814 | 0.414608216 | −0.23108581 | 1.15081653 | −1.10351559 |
| 817 | −0.24632881 | −0.09354384 | −0.13580399 | 0.599029186 |
| 819 | 0.805916178 | 0.96701754 | −0.8811308 | −1.23858491 |
| 820 | 0.744770665 | −0.73855596 | −0.2249849 | −0.2981968 |
| 821 | 1.099377934 | −0.55297074 | −0.58846144 | −1.64325365 |
| 824 | −0.183625049 | 1.183962609 | 1.63494269 | 0.25504959 |
| 826 | 1.678825829 | 1.234136613 | 1.45948258 | 0.224375571 |
| 827 | 2.592229701 | 0.621958527 | −0.52522117 | −0.19676404 |
| 828 | 2.592229701 | 0.57915141 | −0.51767373 | −0.58077497 |
| 829 | 1.670680003 | 1.284791367 | 0.14864516 | −0.84985664 |
| 831 | 1.116827432 | −0.75462162 | 0.39137278 | −0.04171761 |
| 832 | 0.516805788 | −0.98195801 | −1.03806082 | −0.25383454 |
| 833 | 1.490368312 | 0.080687244 | −0.97130296 | 0.833722265 |
| 834 | −0.369014518 | −1.35841128 | −1.27372214 | 1.351157886 |
| 835 | 0.914072736 | −0.8695664 | 0.36889122 | −0.08606658 |
| 836 | 0.998848923 | −0.42464651 | −0.23731009 | 0.395895785 |
| 837 | 1.670680003 | 0.070165381 | −0.64700996 | −0.85055617 |
| 838 | 0.810918992 | −0.75696962 | −0.21854084 | 0.836677293 |
| 839 | 1.066219316 | −0.66764691 | −0.49983634 | 0.669914 |
| 840 | 1.078821776 | −0.72511699 | −1.00012288 | −0.15789319 |
| 845 | −0.163950017 | −0.21616766 | 0.65276069 | −0.52575739 |
| 846 | 0.665621985 | −3.16625248 | 0.34329102 | −1.44312939 |
| 847 | −0.233400992 | −1.15488444 | 0.83051343 | −1.85751897 |
| 848 | −0.631135606 | 0.037691556 | 0.57903451 | −0.9926 |
| 849 | 1.707541313 | 0.010345383 | 0.48581606 | 1.513341091 |
| 850 | 1.447075297 | 0.022864201 | 0.99130501 | 0.473154634 |
| 851 | −0.24632881 | −0.23975349 | −0.01449288 | 0.574861147 |
| 852 | 1.176028423 | −0.85747031 | −0.72464089 | 0.30542841 |
| 856 | 2.237616041 | 0.345329597 | −0.60597063 | −0.71581056 |
| 858 | −1.47960224 | −2.5770536 | −1.03619781 | 0.847300104 |
| 864 | 1.670680003 | 1.284791101 | 0.14864516 | −0.84985664 |
| 865 | 1.670680003 | 1.916382859 | 0.6998144 | 1.124089601 |
| 866 | 1.024819853 | −0.7521596 | 0.35073152 | −2.14193241 |
| 868 | 2.237616041 | −0.17986241 | −0.86317199 | 1.325805381 |
| 869 | 1.747776963 | −0.25802105 | −1.11614995 | −0.77093434 |
| 870 | 2.592229701 | 2.030913569 | −0.50618719 | 1.463926567 |
| 871 | 2.592229701 | 2.510587108 | −0.07540594 | −0.58371481 |
| 872 | 1.800767509 | 1.372656013 | 2.09551175 | 2.849728342 |
| 873 | 1.849432484 | 4.556065495 | −0.39732139 | −0.67726477 |
| 875 | 0.201768224 | 0.618509503 | −0.39732139 | −0.67726477 |
| 876 | 2.237616041 | 1.553468488 | −0.72864242 | −0.33330779 |
| 877 | 0.323968221 | −1.00428076 | −1.65151616 | 1.031096548 |
| 878 | 0.783570663 | 2.023288951 | −0.03975252 | 0.474038265 |
| 879 | 1.187592149 | 1.464239711 | 0.67009263 | 1.103774764 |
| 880 | −0.192632911 | 0.142411101 | 0.79310676 | 0.125548041 |
| 881 | 1.071875228 | 0.911734331 | −1.50008456 | 0.185176261 |
| 882 | 0.798806784 | −0.1516478 | −0.64900063 | −0.77199025 |
| 883 | −0.671908804 | −0.65984824 | 0.5238174 | −0.85314111 |
| 884 | 2.863652137 | 1.896850773 | 0.06443558 | −0.44689505 |
| 885 | 2.314558863 | −0.25458637 | 0.22080129 | −0.04142716 |
| 886 | 2.314558863 | −0.25458637 | 0.22080129 | −0.04142716 |
| 888 | 0.131224024 | 0.21510779 | −1.70996346 | 0.964902175 |
| 889 | 0.742030255 | 0.281479436 | −1.4156326 | −1.91369695 |
| 890 | 1.071875228 | 0.911734331 | −1.50008456 | 0.185176261 |
| 891 | 0.742030255 | 0.281479436 | −1.4156326 | −1.91369695 |
| 892 | 1.749446006 | 0.076054765 | −0.59137073 | 0.291488011 |
| 893 | 0.869958847 | 0.843158237 | 0.61532515 | 3.158279932 |
| 894 | 1.749446006 | 0.076054765 | −0.59137073 | 0.291488011 |
| 897 | −0.047486491 | 1.045012945 | −0.25220201 | −0.31982826 |
| 899 | 0.784181146 | −0.20530019 | −1.89414748 | 0.152726109 |
| 900 | 0.784181146 | −0.20530019 | −1.89414748 | 0.152726109 |
| 901 | −0.440378333 | 0.918089245 | 0.03050609 | −1.62235977 |
| 902 | −0.2346025 | 0.890438419 | −0.13206526 | −0.83961838 |
| 903 | −0.440378333 | 0.918089245 | 0.03050609 | −1.62235977 |
| 904 | −1.320466583 | −2.49763118 | 0.9787365 | −1.85867969 |
| 905 | −0.386224123 | −0.24799559 | 1.19406353 | −1.61243489 |
| 908 | 1.878331515 | 1.287303121 | 0.11530502 | 1.132065786 |

-continued

| Material No. | MORV value for Equation a.) | MORV Value for Equation b.) | MORV Value for Equation c.) | MORV value for Equation d.) |
|---|---|---|---|---|
| 909 | 0.614968453 | −1.61827184 | −0.80789799 | −0.66927285 |
| 912 | 0.530707518 | 0.774109528 | 3.0396125 | 4.394775258 |
| 913 | 0.337020095 | 1.531840025 | 0.10544973 | 0.347450471 |
| 914 | 0.774589061 | 1.224705331 | 1.87994281 | −0.11684579 |
| 916 | −0.363201351 | 0.35600238 | −1.20673542 | 2.056973054 |
| 918 | 0.153047955 | 0.702054562 | 0.76757802 | 0.096096862 |
| 919 | 2.891894151 | 2.295157633 | 3.54101626 | 1.984030826 |
| 920 | 1.292959895 | 0.808281618 | 2.92956952 | 2.204248324 |
| 921 | −0.465333775 | 0.862817284 | 0.1439546 | 0.64701735 |
| 922 | 1.54265003 | 0.291977233 | 0.79089158 | 0.801314068 |
| 923 | 1.340862559 | 0.503169303 | 0.53213093 | 3.164832031 |
| 924 | 0.158497146 | 1.507280765 | 2.25315926 | 1.173977914 |
| 925 | 1.23162703 | 1.671882685 | 3.1838372 | −0.22917041 |
| 926 | 2.608734063 | 3.080604939 | −0.69726361 | −0.36219702 |
| 927 | 1.879182741 | 3.409153142 | 2.48473663 | 3.409954437 |
| 928 | −0.093106169 | 0.019939108 | 0.15932154 | 1.229749745 |
| 929 | 1.670680003 | 1.94609957 | 0.19633838 | 1.14825764 |
| 930 | 3.052627325 | 0.956834107 | −0.29721209 | −0.31007607 |
| 931 | 0.367631287 | 0.501274945 | −1.31074554 | −0.39331005 |
| 933 | 3.702965303 | 3.03402795 | 4.33630831 | 4.238503729 |
| 937 | 0.570011387 | 0.097928934 | 1.03350455 | −0.13392581 |
| 939 | 1.801474588 | 0.770314085 | 0.70188154 | 0.22333959 |
| 940 | −0.412950838 | −0.1781887 | 0.50649275 | −0.57215449 |
| 941 | 1.691004766 | −0.42331992 | 0.66279648 | 0.0318465 |
| 942 | 1.451782586 | −0.565439 | −0.32447381 | −0.43378383 |
| 943 | 1.188491672 | 0.120632811 | 0.20106994 | 3.078484746 |
| 945 | 1.214814941 | 0.806987609 | 0.47605587 | 1.372949466 |
| 946 | 0.561732094 | 1.21448402 | 0.35542793 | −1.03704442 |
| 947 | 0.956565856 | 1.505997176 | 0.88115653 | −0.60583691 |
| 948 | 0.592575441 | 1.383482681 | 0.93567635 | 1.058669028 |
| 950 | 0.343657562 | −0.85471906 | −0.21125904 | 1.184648122 |
| 951 | 1.236659334 | 3.828926809 | 1.57729777 | −0.31942874 |
| 953 | 1.836389049 | 0.755753735 | −0.36014522 | 1.262853393 |
| 953 | 1.836389049 | 0.755753735 | −0.36014522 | 1.262853393 |
| 954 | 1.001653875 | −0.85635082 | 0.89224781 | −0.39245818 |
| 955 | −0.122918652 | −0.846489 | −0.63367729 | 1.182912962 |
| 956 | 0.589766639 | −0.9783487 | −0.67638264 | −0.38772225 |
| 958 | 0.715082397 | −0.90020686 | 0.86817768 | 0.030652004 |
| 959 | 1.609198886 | 0.500797943 | 0.795571 | 0.908389449 |
| 960 | 0.952787327 | −0.90555475 | −0.17381408 | 0.06786323 |
| 962 | 1.836429446 | 0.208275147 | −0.14300625 | 1.067462181 |
| 965 | 1.9158432 | 0.35211823 | −1.02174589 | 0.625657932 |
| 967 | 1.383869627 | 0.274520494 | −0.11659267 | 0.840327437 |
| 969 | −0.445579934 | −1.68867059 | −0.5241276 | 2.233793943 |
| 971 | 0.736419048 | 0.409875189 | −0.63140848 | 0.034514594 |
| 973 | 1.073465817 | 2.18418874 | 2.01361447 | −0.93754437 |
| 974 | 0.130904221 | 1.882440008 | 1.85101055 | 0.112524893 |
| 976 | −0.236681385 | −0.09745533 | 0.1779313 | 2.08923366 |
| 977 | 0.904402612 | 0.936956925 | 0.87731788 | 0.102346515 |
| 978 | 2.201759817 | 2.123549573 | 3.7881607 | 2.358768953 |
| 980 | 1.784266982 | 1.845281076 | 3.42873622 | −0.31098233 |
| 981 | −0.225023329 | 0.087962898 | −0.29053012 | 0.514272787 |
| 982 | −0.231175318 | −0.0159671 | 1.27391892 | 1.090487158 |
| 983 | 0.889215441 | 0.24321159 | 0.06877629 | 0.816247177 |
| 985 | 1.864634345 | 0.133647536 | 1.29803755 | 1.951226654 |
| 986 | 0.511450274 | −2.33512445 | −0.56246315 | −0.42184152 |
| 987 | 0.847260813 | 0.368638185 | 0.4114346 | 0.219336109 |
| 988 | 1.596170102 | 1.592158381 | 0.30052357 | 0.283467897 |
| 993 | −3.549941097 | −2.6847861 | −0.17502622 | 1.41034664 |
| 994 | 0.445802042 | 0.899738574 | 0.61059602 | 0.323194673 |
| 995 | 0.949498724 | 0.357111159 | 0.28371155 | −0.14156488 |
| 998 | 2.197271885 | 1.578871826 | 0.90563334 | 1.056619658 |
| 998 | 2.197271885 | 1.578871826 | 0.90563334 | 1.056619658 |
| 1000 | 1.456120673 | 0.626173572 | 0.07683183 | −0.43324035 |
| 1001 | −0.440378333 | 0.918089245 | 0.03050609 | −1.62235977 |
| 1002 | 0.819929066 | 0.459101825 | −0.09227583 | 0.324342063 |
| 1003 | 1.64412453 | −0.09343399 | 0.70197344 | 3.710273595 |
| 1004 | 0.796928207 | 0.459954079 | −0.88538616 | 0.152000937 |
| 1005 | 0.044923203 | −0.19994963 | 0.60082875 | 0.258347835 |
| 1006 | −0.320452673 | −0.33232662 | −0.52315783 | 1.406273663 |
| 1007 | 4.040291133 | 3.474551355 | 3.57146797 | 3.565985043 |
| 1008 | 0.764519082 | 0.917635102 | 2.88258762 | 2.319622474 |
| 1009 | −0.071112206 | 0.539362906 | 2.98048732 | 0.580423329 |
| 1010 | −0.689737481 | 0.547928768 | 1.98805626 | −0.76653376 |
| 1011 | 0.343668917 | 0.931501008 | −0.05483722 | 0.395369857 |

-continued

| Material No. | MORV value for Equation a.) | MORV Value for Equation b.) | MORV Value for Equation c.) | MORV value for Equation d.) |
|---|---|---|---|---|
| 1012 | 1.926713131 | 0.124849138 | −0.09654906 | 1.126499382 |
| 1016 | 0.124247716 | 0.193102712 | 0.39003599 | 1.737670628 |
| 1017 | 0.131224136 | 0.21510779 | −1.70996346 | 0.964902175 |
| 1018 | 0.499624069 | 0.962843507 | 0.77617619 | −1.15296947 |
| 1019 | 0.813491983 | 0.322635656 | 0.02800396 | 0.599500927 |
| 1020 | 0.715468114 | 1.015469049 | 1.45994989 | 0.352548581 |
| 1021 | −1.176339404 | 1.539767848 | −0.14427147 | 1.389902738 |
| 1022 | 1.364966718 | 1.690570939 | 2.05914194 | 2.364375484 |
| 1023 | 2.154641091 | 0.800066339 | 0.85365652 | 0.965810338 |
| 1024 | 2.302280068 | 1.252164308 | 1.73414439 | 1.549538352 |
| 1025 | 1.878331515 | 1.287303121 | 0.11530502 | 1.132065786 |
| 1026 | 2.97722987 | 2.096441965 | 3.87172868 | 0.550274831 |
| 1027 | 2.474381478 | 1.950326182 | 3.81861867 | 1.366897355 |
| 1028 | 1.778414353 | 3.114931059 | 4.47690731 | 6.054314034 |
| 1029 | 3.672910795 | 2.760483725 | 3.26915034 | 3.042677588 |
| 1030 | −0.604959715 | −2.13584086 | 0.8687855 | 0.024144016 |
| 1031 | 2.012732245 | 2.293857161 | 0.54405555 | 1.261882121 |
| 1032 | −1.086688867 | 0.953083194 | 2.92177054 | 0.876865185 |
| 1033 | 1.617520676 | 1.008017006 | 2.21183536 | −0.1288484 |
| 1035 | 2.506372295 | 3.419954592 | 4.58206882 | 4.134341651 |
| 1036 | −0.675805062 | −0.15357004 | 0.94597719 | 3.966016669 |
| 1037 | −0.275092569 | −0.67687665 | −0.52763797 | 1.489972106 |
| 1038 | 2.753559643 | 3.81185814 | 2.71344734 | 2.243351472 |
| 1039 | 0.65087433 | 0.026885305 | −0.0153558 | 0.011870127 |
| 1040 | 0.141526548 | −1.65455278 | 0.50170705 | −1.90794 |
| 1041 | 0.458680435 | −0.69730218 | −0.48806249 | 0.586073092 |
| 1042 | −0.513264812 | −0.22001961 | 0.36339519 | 1.03208599 |
| 1043 | −1.497887014 | −1.76116109 | −0.76634926 | 1.137002742 |
| 1045 | 2.863652137 | 1.96790869 | 0.43661485 | −0.44756897 |
| 1046 | 0.981194248 | 1.73892162 | 2.21166953 | 2.738129365 |
| 1047 | 0.981194248 | 1.73892162 | 2.21166953 | 2.738129365 |
| 1051 | 0.70261974 | −0.22197386 | 0.19710806 | −2.37196477 |
| 1052 | 0.662126832 | 0.741436531 | 0.61672724 | 0.289359903 |
| 1053 | 0.87463644 | −0.19717783 | 1.2664131 | −0.4187507 |
| 1054 | 0.284558077 | −1.46754925 | −0.03124571 | 0.587227244 |
| 1055 | 0.885837831 | −0.91907796 | −0.45817355 | −1.1936897 |
| 1057 | 0.790964847 | 1.387925398 | −0.18370692 | 1.302393792 |
| 1058 | −1.052897931 | −0.85226912 | 0.90324527 | −1.09684959 |
| 1059 | −0.871565421 | −0.17856476 | 1.51267137 | −1.52734367 |
| 1060 | 3.311161199 | 3.074783921 | 2.10199297 | 1.822541682 |
| 1061 | −0.655128061 | 0.497032417 | 0.92381279 | −0.56348341 |
| 1062 | −0.443129049 | 0.96200606 | 1.51641349 | −0.22974864 |
| 1063 | 1.385675542 | 0.738759296 | 1.1677069 | 0.501211562 |
| 1064 | 1.670680003 | −0.20756775 | −0.73755051 | −0.84924056 |
| 1065 | 1.43532227 | 1.656262941 | −1.09448841 | 1.674272267 |
| 1066 | 1.670680003 | 1.284791101 | 0.14864516 | −0.84985664 |
| 1067 | 2.237616041 | 0.345329863 | −0.60597063 | −0.71581056 |
| 1069 | −0.24632881 | −0.23975349 | −0.01449288 | 0.574861147 |
| 1070 | 1.670680003 | 0.070165381 | −0.64700996 | −0.85055617 |
| 1071 | −1.02687397 | −0.36244273 | 0.13010074 | 0.535909448 |
| 1072 | 1.670680003 | 1.94609957 | 0.19633838 | 1.14825764 |
| 1073 | 2.237616041 | 1.438074134 | 0.31117554 | −0.71786492 |
| 1074 | −0.192632911 | 0.142411101 | 0.79310676 | 0.125548041 |
| 1075 | 0.909356011 | 0.368597887 | 1.03689838 | 1.001198751 |
| 1076 | 0.812238101 | 0.195908668 | 0.21564664 | 0.219336109 |
| 1077 | 0.325255266 | 1.131242708 | −2.79377204 | −0.62848261 |
| 1078 | 0.325255266 | 1.131242708 | −2.79377204 | −0.62848261 |
| 1079 | 0.85330799 | −0.6855194 | −0.90046979 | −0.46415796 |
| 1081 | −0.131519393 | 0.731836014 | 0.81604919 | −1.29993979 |
| 1082 | 0.744770665 | 0.155243763 | −1.8029919 | 1.023503542 |
| 1083 | 1.415726941 | 0.086297223 | 3.43559555 | −0.12964168 |
| 1084 | 0.161304111 | 0.66712144 | 0.58401752 | 0.373809692 |
| 1085 | −0.72863532 | −0.2873027 | 2.21251376 | 3.003873022 |
| 1088 | −1.1773616 | −0.23258175 | 0.40529195 | 0.994988969 |
| 1089 | 2.769817302 | 1.661618789 | 3.97585272 | 1.059236597 |
| 1090 | 3.052627325 | 0.420821685 | −0.57080756 | 1.751222205 |
| 1091 | −3.379896722 | −3.71174986 | 2.53586709 | 0.644702886 |
| 1093 | 0.72304265 | 1.667011476 | 2.53982093 | 2.7903213 |
| 1095 | 0.744219765 | 1.372184572 | 0.15852396 | 1.126053442 |
| 1097 | 4.407270402 | 2.670641491 | 5.02636153 | 5.361271976 |
| 1098 | −1.85804837 | −2.59071226 | −0.46522239 | 0.655734646 |
| 1099 | 0.745797788 | −0.20547378 | 4.27836342 | 4.646390386 |
| 1102 | 2.068748434 | −0.24299896 | 0.07214682 | −1.11758276 |
| 1104 | 1.018876287 | 0.025163067 | −0.1106021 | 0.838914654 |
| 1105 | 2.387326861 | 3.865456674 | 2.2251199 | 0.728667998 |

-continued

| Material No. | MORV value for Equation a.) | MORV Value for Equation b.) | MORV Value for Equation c.) | MORV value for Equation d.) |
|---|---|---|---|---|
| 1107 | 2.352582059 | 2.595496601 | 3.20492728 | 2.844590737 |
| 1110 | 0.302703712 | 0.599942142 | −0.25637571 | −0.03195517 |
| 1111 | 0.750930333 | 0.656784751 | 1.68326413 | 0.329846578 |
| 1112 | −0.205527848 | 0.287622624 | −0.00340777 | 0.59203719 |
| 1115 | 0.999825037 | 0.662221152 | 0.43571192 | 0.342558518 |
| 1116 | 0.873381263 | 1.544324176 | 0.13703728 | −0.38172701 |
| 1117 | −0.682983903 | 1.798204302 | 2.42110319 | −0.39173951 |
| 1118 | 0.069769623 | 0.496895599 | 0.67857133 | −0.14954441 |
| 1119 | −0.671908804 | −0.65984824 | 0.5238174 | −0.85314111 |
| 1120 | 0.953790113 | 1.106552668 | 3.00006904 | 1.585038764 |
| 1121 | −1.184630973 | 2.476138312 | 4.80971952 | 2.450646806 |
| 1122 | −1.02687397 | −0.36244273 | 0.13010074 | 0.535909448 |
| 1125 | 0.387315524 | −0.36101406 | 1.14153708 | −0.75303953 |
| 1126 | 1.021783831 | −0.0070257 | −0.14327539 | 3.954381426 |
| 1127 | 0.990592079 | 0.305612583 | 0.14155512 | −0.29526854 |
| 1128 | 0.990592079 | 0.305612583 | 0.14155512 | −0.29526854 |
| 1129 | 3.18966648 | 3.284362987 | 4.49398568 | 3.950809104 |
| 1131 | 1.650621055 | 1.545704806 | 2.37535081 | 1.259373143 |
| 1133 | −1.519747805 | −0.60804324 | 0.02746106 | 0.590708892 |
| 1134 | 0.815942067 | −0.16126019 | −0.54117238 | 0.613093526 |
| 1135 | 0.626973385 | 1.998305877 | 2.61706075 | 1.570404253 |
| 1136 | 2.812199484 | 1.353198146 | 2.05618426 | 1.869204406 |
| 1137 | 2.208307057 | 1.387136198 | 3.21521374 | 2.069795393 |
| 1138 | 1.670680003 | 1.316442078 | 0.14822999 | −0.46985154 |
| 1139 | 1.408517438 | 0.890457374 | 1.24524408 | 0.685687797 |
| 1140 | 2.765860952 | 2.525539595 | 4.12464228 | 3.833744077 |
| 1141 | −0.484394663 | 0.677713073 | −0.22783646 | −0.37267608 |
| 1142 | 2.54335679 | 4.298105601 | 3.36234238 | 2.684404542 |
| 1143 | 4.204367611 | 3.062126931 | 3.4234313 | 2.072899554 |
| 1144 | 2.479165229 | 3.226545885 | 4.65897152 | 4.952127235 |
| 1145 | 2.479158921 | 3.226545885 | 4.65897152 | 4.952127235 |
| 1146 | 0.774334025 | 1.075800774 | 1.06893156 | 1.011113116 |
| 1147 | 0.844648531 | 1.21935371 | 2.59138595 | 0.805938034 |
| 1148 | 2.906236436 | 1.550674121 | 3.56959167 | 2.832126896 |
| 1149 | 2.837627443 | 3.707154326 | 4.53384262 | 2.625871865 |

Freshening Compositions and Methods

A freshening composition having a viscosity of from about 1 mPa·s to about 50,000 mPa·s, preferably from about 1 mPa·s to about 2000 mPa·s, most preferably from about 1 mPa·s to about 400 mPa·s, a pH from about 3 to about 10, preferably from about 4 to about 8, most preferably from about 5 to about 8, said freshening composition comprising, based on total freshening composition weight:

a) a sum total of from about 0.0001% to about 2%, preferably from about 0.0001% to about 1.5%, more preferably from about 0.001% to about 1%, most preferably from about 0.007% to about 0.7% of 1 or more malodor reduction materials, preferably 1 to about 75 malodor reduction materials, more preferably 1 to about 50 malodor reduction materials, more preferably 1 to about 35 malodor reduction materials, most preferably 1 to about 20 malodor reduction materials, each of said malodor reduction materials having a MORV of at least 0.5, preferably from 0.5 to 10, more preferably from 1 to 10, most preferably from 1 to 5, and preferably each of said malodor reduction materials having a Universal MORV, or said sum total of malodor reduction materials having a Blocker Index of less than 3, more preferable less than about 2.5 even more preferably less than about 2 and still more preferably less than about 1 and most preferably 0 and/or a Blocker Index average of 3 to about 0.001; and b) from about 0.01% to about 3%, preferably from about 0.4% to about 1%, more preferably from about 0.1% to about 0.5%, most preferably from about 0.1% to about 0.3% of solublizing agent, preferably said solublizing agent is selected from the group consisting of a surfactant, a solvent and mixtures thereof, preferably
   (i) preferably said surfactant comprises a non-ionic surfactant;
   (ii) preferably said solvent comprises an alcohol, a polyol and mixtures thereof;

c) optionally, an adjunct ingredient, is disclosed.

As the viscosity is lowered you obtain improved sprayability and improved penetration into fabric. A pH 5-8 is useful for neutralizing both acidic and basic malodors, and this is useful in a odor neutralizing composition. Also it helps improve perfume stability as some ingredients may not be stable at extreme pH. Using fewer materials helps reduce complexity of the formula and therefore the cost of manufacturing the composition. The lower the blocker index (BI) of a malodor reducing material the lower the perception of malodor.

As the range for the solublizing agent is narrowed is you can maintain the required solublization without wanted foaming during processing or use. Also lower amounts are better for cost reasons. Finally, Non-ionic surfactants are more compatible with other ingredients such as cationic anti-microbials ("quats"), PEI polymers, etc.

In one aspect of said freshening composition, said sum total of malodor reduction materials has a Blocker Index of less than 3, more preferable less than about 2.5 even more preferably less than about 2 and still more preferably less than about 1 and most preferably 0 and/or a Blocker Index average of 3 to about 0.001.

In one aspect of said freshening composition, each of said malodor reduction materials has a MORV of at least 0.5, preferably from 0.5 to 10, more preferably from 1 to 10, most preferably from 1 to 5, and preferably each of said malodor reduction materials having a Universal MORV.

In one aspect of said freshening composition, said sum total of malodor reduction materials has a Fragrance Fidelity Index average of 3 to about 0.001 Fragrance Fidelity Index, preferably each malodor reduction material in said sum total of malodor reduction materials has a Fragrance Fidelity Index of less than 3, preferably less than 2, more preferably less than 1 and most preferably each malodor reduction material in said sum total of malodor reduction materials has a Fragrance Fidelity Index of 0.

In one aspect of said freshening composition, said freshening composition comprises one or more perfume raw materials and has a weight ratio of parts of malodor reduction materials to parts of perfume from about 1:20,000 to about 3000:1, preferably from about 1:10,000 to 1,000:1, more preferably from 5000:1 to about 500:1 and most preferably from about 1:15 to about 2:1. As the range of the ratio narrows the balance of fragrance odor to any odor coming from the MORV materials is improved.

In one aspect of said freshening composition, said malodor reduction material is selected from the group consisting of Table 1 materials and mixtures thereof; preferably said material is selected from the group consisting of Table 1 materials 1, 2, 3, 4, 7, 9, 10, 11, 13, 14, 16, 17, 18, 21, 22, 23, 25, 28, 29, 30, 31, 32, 33, 34, 35, 36, 37, 38, 39, 42, 43, 47, 48, 49, 50, 52, 57, 61, 62, 63, 64, 65, 67, 68, 69, 70, 71, 74, 75, 76, 77, 78, 79, 80, 82, 83, 85, 91, 92, 93, 98, 100, 101, 102, 103, 104, 105, 106, 108, 109, 110, 112, 113, 114, 117, 119, 120, 122, 123, 126, 128, 130, 134, 135, 137, 140, 141, 142, 143, 145, 146, 148, 149, 152, 153, 155, 156, 158, 159, 161, 162, 167, 168, 170, 174, 175, 176, 177, 178, 179, 182, 183, 184, 185, 186, 187, 189, 190, 192, 193, 195, 196, 197, 199, 206, 208, 209, 210, 211, 212, 215, 218, 221, 227, 228, 229, 230, 231, 233, 234, 238, 242, 243, 244, 246, 247, 249, 252, 253, 254, 256, 259, 260, 261, 263, 267, 269, 271, 274, 276, 277, 278, 280, 281, 285, 286, 288, 289, 290, 292, 293, 294, 295, 296, 300, 301, 303, 307, 316, 317, 318, 321, 322, 323, 324, 325, 328, 329, 330, 331, 332, 333, 334, 335, 336, 338, 339, 342, 343, 344, 347, 349, 350, 352, 353, 356, 358, 359, 360, 361, 362, 363, 364, 368, 369, 370, 371, 372, 373, 374, 375, 377, 378, 381, 385, 386, 388, 390, 391, 394, 397, 398, 407, 413, 414, 415, 416, 417, 418, 421, 424, 425, 426, 428, 429, 432, 436, 441, 444, 445, 449, 450, 453, 457, 459, 461, 462, 463, 464, 465, 466, 467, 468, 470, 471, 473, 474, 475, 478, 479, 480, 482, 484, 485, 486, 487, 488, 491, 493, 497, 498, 501, 502, 503, 505, 519, 520, 521, 524, 527, 529, 530, 531, 532, 534, 537, 541, 544, 546, 548, 550, 551, 552, 553, 555, 558, 559, 560, 561, 562, 563, 565, 566, 567, 568, 569, 570, 571, 572, 573, 574, 577, 578, 580, 581, 582, 584, 586, 587, 589, 591, 592, 594, 595, 599, 600, 601, 603, 604, 606, 607, 608, 609, 610, 611, 612, 613, 614, 615, 616, 618, 620, 621, 624, 625, 626, 627, 628, 631, 632, 633, 635, 636, 638, 639, 644, 649, 650, 653, 655, 658, 659, 660, 661, 663, 668, 671, 673, 674, 675, 676, 677, 678, 679, 680, 681, 682, 683, 684, 686, 691, 692, 693, 694, 696, 697, 698, 700, 702, 704, 706, 707, 708, 709, 710, 711, 712, 713, 714, 715, 716, 717, 718, 719, 720, 721, 722, 723, 724, 725, 726, 727, 730, 731, 733, 735, 736, 738, 741, 742, 746, 748, 750, 752, 754, 757, 758, 763, 764, 766, 767, 768, 769, 770, 771, 772, 774, 775, 776, 778, 781, 782, 786, 788, 791, 792, 800, 802, 803, 804, 805, 806, 807, 814, 821, 824, 826, 827, 828, 829, 831, 833, 834, 837, 839, 840, 849, 850, 852, 856, 864, 865, 866, 868, 869, 870, 871, 872, 873, 876, 877, 878, 879, 881, 884, 885, 886, 890, 892, 893, 894, 897, 905, 908, 912, 913, 914, 916, 919, 920, 922, 923, 924, 925, 926, 927, 928, 929, 930, 933, 937, 939, 941, 942, 943, 945, 946, 947, 948, 950, 951, 953, 954, 955, 959, 962, 965, 967, 969, 973, 974, 976, 978, 980, 982, 985, 988, 993, 998, 1000, 1003, 1006, 1007, 1008, 1009, 1010, 1012, 1016, 1020, 1021, 1022, 1023, 1024, 1025, 1026, 1027, 1028, 1029, 1031, 1032, 1033, 1035, 1036, 1037, 1038, 1042, 1043, 1045, 1046, 1047, 1053, 1057, 1059, 1060, 1062, 1063, 1064, 1065, 1066, 1067, 1070, 1072, 1073, 1075, 1077, 1078, 1082, 1083, 1085, 1089, 1090, 1091, 1093, 1095, 1097, 1099, 1102, 1104, 1105, 1107, 1111, 1113, 1116, 1117, 1120, 1121, 1125, 1126, 1129, 1131, 1135, 1136, 1137, 1138, 1139, 1140, 1142, 1143, 1144, 1145, 1146, 1147, 1148, 1149, Table 2 materials 2, 23, 141, 185, 227, 230, 246, 248, 343, 359, 565, 631, 659, 674, 678, 679, 715, 758, 1028, 1097, Table 3 materials 12, 19, 20, 24, 26, 27, 53, 54, 55, 59, 72, 73, 81, 84, 96, 97, 107, 111, 115, 116, 125, 133, 147, 150, 151, 154, 157, 163, 166, 169, 181, 191, 194, 198, 201, 204, 205, 213, 214, 232, 237, 239, 255, 258, 264, 270, 273, 275, 282, 283, 284, 287, 302, 306, 308, 310, 312, 314, 319, 346, 354, 355, 365, 366, 376, 379, 387, 400, 412, 419, 420, 437, 438, 439, 440, 442, 443, 447, 448, 454, 455, 469, 472, 477, 481, 492, 495, 496, 504, 509, 510, 512, 515, 517, 518, 522, 525, 526, 528, 535, 536, 538, 540, 542, 547, 549, 554, 556, 557, 575, 576, 579, 583, 585, 588, 602, 605, 617, 619, 640, 641, 645, 647, 651, 652, 662, 664, 665, 667, 672, 687, 699, 701, 703, 740, 743, 744, 745, 755, 760, 761, 777, 779, 784, 789, 796, 797, 799, 808, 810, 811, 812, 817, 819, 820, 832, 835, 836, 838, 845, 846, 847, 848, 851, 858, 875, 880, 882, 883, 888, 889, 891, 899, 900, 901, 902, 903, 904, 909, 918, 921, 931, 940, 956, 958, 960, 971, 977, 981, 983, 986, 987, 994, 995, 1001, 1002, 1004, 1005, 1011, 1017, 1018, 1019, 1030, 1039, 1040, 1041, 1051, 1052, 1054, 1055, 1058, 1061, 1069, 1071, 1074, 1076, 1079, 1081, 1084, 1088, 1098, 1110, 1112, 1115, 1118, 1119, 1122, 1127, 1128, 1133, 1134, 1141 and mixtures thereof; more preferably said material is selected from the group consisting of Table 1 materials 1, 2, 3, 4, 7, 9, 10, 11, 13, 14, 16, 17, 18, 21, 22, 23, 25, 28, 29, 30, 31, 32, 33, 34, 35, 36, 37, 38, 39, 42, 43, 47, 48, 49, 50, 52, 57, 61, 62, 63, 64, 65, 67, 68, 69, 70, 71, 74, 75, 76, 77, 78, 79, 80, 82, 83, 85, 91, 92, 93, 98, 100, 101, 102, 103, 104, 105, 106, 108, 109, 110, 112, 113, 114, 117, 119, 120, 122, 123, 126, 128, 130, 134, 135, 137, 140, 141, 142, 143, 145, 146, 148, 149, 152, 153, 155, 156, 158, 159, 161, 162, 167, 168, 170, 174, 175, 176, 177, 178, 179, 182, 183, 184, 185, 186, 187, 189, 190, 192, 193, 195, 196, 197, 199, 206, 208, 209, 210, 211, 212, 215, 218, 221, 227, 228, 229, 230, 231, 233, 234, 238, 242, 243, 244, 246, 247, 249, 252, 253, 254, 256, 259, 260, 261, 263, 267, 269, 271, 274, 276, 277, 278, 280, 281, 285, 286, 288, 289, 290, 292, 293, 294, 295, 296, 300, 301, 303, 307, 316, 317, 318, 321, 322, 323, 324, 325, 328, 329, 330, 331, 332, 333, 334, 335, 336, 338, 339, 342, 343, 344, 347, 349, 350, 352, 353, 356, 358, 359, 360, 361, 362, 363, 364, 368, 369, 370, 371, 372, 373, 374, 375, 377, 378, 381, 385, 386, 388, 390, 391, 394, 397, 398, 407, 413, 414, 415, 416, 417, 418, 421, 424, 425, 426, 428, 429, 432, 436, 441, 444, 445, 449, 450, 453, 457, 459, 461, 462, 463, 464, 465, 466, 467, 468, 470, 471, 473, 474, 475, 478, 479, 480, 482, 484, 485, 486, 487, 488, 491, 493, 497, 498, 501, 502, 503, 505, 519, 520, 521, 524, 527, 529, 530, 531, 532, 534, 537, 541, 544, 546, 548, 550, 551, 552, 553, 555, 558, 559, 560, 561, 562, 563, 565, 566, 567, 568, 569, 570, 571, 572, 573, 574, 577, 578, 580, 581, 582, 584, 586, 587, 589, 591, 592, 594, 595, 599, 600, 601, 603, 604, 606, 607, 608, 609, 610, 611, 612, 613, 614, 615, 616, 618, 620, 621, 624, 625, 626, 627, 628, 631, 632, 633, 635, 636, 638, 639, 644, 649, 650, 653, 655, 658, 659, 660, 661, 663, 668, 671, 673, 674, 675, 676, 677, 678, 679, 680, 681, 682, 683, 684, 686, 691, 692, 693, 694, 696, 697, 698, 700, 702, 704, 706, 707, 708, 709, 710, 711, 712, 713, 714, 715, 716, 717, 718, 719, 720, 721, 722, 723, 724, 725, 726, 727, 730, 731, 733, 735, 736, 738, 741, 742, 746, 748, 750, 752, 754, 757, 758, 763, 764, 766, 767, 768, 769, 770, 771, 772, 774, 775, 776, 778, 781, 782, 786, 788, 791, 792, 800, 802, 803, 804, 805, 806, 807, 814, 821, 824, 826, 827, 828, 829, 831, 833, 834, 837, 839, 840, 849, 850, 852, 856, 864, 865, 866, 868, 869, 870, 871, 872, 873, 876, 877, 878, 879, 881, 884, 885, 886, 890, 892, 893, 894, 897, 905, 908, 912, 913, 914, 916, 919, 920, 922, 923, 924, 925, 926, 927, 928, 929, 930, 933, 937, 939, 941, 942, 943, 945, 946, 947, 948, 950, 951, 953, 954, 955, 959, 962, 965, 967, 969, 973, 974, 976, 978, 980, 982, 985, 988, 993, 998, 1000, 1003, 1006, 1007, 1008, 1009, 1010, 1012, 1016, 1020, 1021, 1022, 1023, 1024, 1025, 1026, 1027, 1028, 1029, 1031, 1032, 1033, 1035, 1036, 1037, 1038, 1042, 1043, 1045, 1046, 1047, 1053, 1057, 1059, 1060, 1062, 1063, 1064, 1065, 1066, 1067, 1070, 1072, 1073, 1075, 1077, 1078, 1082, 1083, 1085, 1089, 1090, 1091, 1093, 1095, 1097, 1099, 1102, 1104, 1105, 1107, 1111, 1113, 1116, 1117, 1120, 1121, 1125, 1126, 1129, 1131, 1135, 1136, 1137, 1138, 1139, 1140, 1142, 1143, 1144, 1145, 1146, 1147, 1148, 1149, Table 2 materials 2, 23, 141, 185, 227, 230, 246, 248, 343, 359, 565, 631, 659, 674, 678, 679, 715, 758, 1028, 1097 and mixtures thereof, more preferably said material is selected from the group consisting of Table 4 materials 7, 14, 39, 48, 183, 199, 206, 212, 215, 229, 260, 261, 281, 329, 335, 353, 360, 441, 484, 487, 488, 501, 566, 567, 569, 570, 573, 574, 603, 616, 621, 624, 627, 632, 663, 680, 684, 694, 696, 708, 712, 714, 726, 750, 764, 775, 776, 788, 804, 872, 919, 927, 933, 978, 1007, 1022, 1024, 1027, 1029, 1035, 1038, 1060, 1089, 1107, 1129, 1131, 1136, 1137, 1140, 1142, 1143, 1144, 1145, 1148, 1149, Table 5 materials 248, most preferably said material is selected from the group consisting of Table 4 materials 261, 680, 788, 1129, 1148, 1149 and mixtures thereof.

In one aspect of said freshening composition, said freshening composition comprises a malodor reduction material comprising one or more malodor reduction materials having a log P of 3 or less, preferably a log P from 0.1 to 3, preferably said one or more malodor reduction materials are selected from the group consisting of Table 1 materials 4; 16; 17; 34; 37; 42; 43; 61; 65; 70; 82; 98; 106; 108; 110; 112; 113; 117; 126; 130; 141; 143; 146; 155; 156; 167; 168; 170; 179; 187; 190; 193; 199; 218; 247; 249; 254; 256; 259; 278; 281; 286; 288; 321; 323; 332; 347; 350; 353; 373; 374; 375; 377; 394; 407; 415; 417; 425; 436; 445; 450; 464; 474; 485; 491; 493; 527; 530; 531; 546; 551; 553; 555; 580; 581; 586; 587; 595; 612; 627; 636; 638; 639; 649; 655; 658; 668; 683; 730; 733; 735; 736; 738; 742; 748; 767; 768; 772; 786; 792; 803; 805; 807; 824; 829; 833; 834; 864; 865; 897; 923; 924; 928; 929; 937; 946; 955; 962; 969; 974; 976; 980; 982; 993; 1012; 1020; 1021; 1026; 1027; 1036; 1037; 1042; 1059; 1064; 1066; 1072; 1083; 1085; 1091; 1111; 1117; 1125; 1139; 1146 Table 2 material 141; Table 3 materials 26; 34; 37; 43; 53; 65; 70; 73; 82; 84; 96; 97; 98; 106; 107; 108; 110; 115; 116; 125; 126; 143; 146; 163; 166; 167; 169; 187; 194; 198; 201; 205; 213; 214; 232; 239; 254; 255; 256; 258; 282; 284; 286; 287; 288; 314; 323; 365; 366; 374; 375; 376; 377; 379; 400; 407; 417; 419; 439; 440; 442; 443; 469; 474; 485; 491; 492; 526; 528; 530; 538; 542; 547; 549; 554; 555; 556; 576; 579; 583; 585; 588; 605; 617; 636; 638; 640; 647; 651; 652; 664; 665; 683; 699; 701; 730; 740; 742; 743; 755; 760; 761; 772; 777; 784; 789; 792; 796; 797; 803; 805; 807; 808; 810; 811; 812; 817; 832; 833; 835; 845; 846; 848; 851; 858; 865; 882; 883; 902; 904; 918; 921; 923; 931; 937; 946; 956; 977; 981; 983; 1002; 1004; 1019; 1020; 1026; 1036; 1039; 1040; 1041; 1069; 1071; 1079; 1081; 1084; 1091; 1098; 1110; 1111; 1112; 1118; 1119; 1122; 1133; 1139; 1146; and mixtures thereof, more preferably said malodor reduction materials are selected from the group consisting of Table 1 materials 4; 16; 17; 34; 37; 42; 43; 61; 65; 70; 82; 98; 106; 108; 110; 112; 113; 117; 126; 130; 141; 143; 146; 155; 156; 167; 168; 170; 179; 187; 190; 193; 199; 218; 247; 249; 254; 256; 259; 278; 281; 286; 288; 321; 323; 332; 347; 350; 353; 373; 374; 375; 377; 394; 407; 415; 417; 425; 436; 445; 450; 464; 474; 485; 491; 493; 527; 530; 531; 546; 551; 553; 555; 580; 581; 586; 587; 595; 612; 627; 636; 638; 639; 649; 655; 658; 668; 683; 730; 733; 735; 736; 738; 742; 748; 767; 768; 772; 786; 792; 803; 805; 807; 824; 829; 833; 834; 864; 865; 897; 923; 924; 928; 929; 937; 946; 955; 962; 969; 974; 976; 980; 982; 993; 1012; 1020; 1021; 1026; 1027; 1036; 1037; 1042; 1059; 1064; 1066; 1072; 1083; 1085; 1091; 1111; 1117; 1125; 1139; 1146 Table 2 material 141 and mixtures thereof, most preferably said malodor reduction material is selected from the group consisting of Table 4 materials 199; 281; 353; 627; 1027 and mixtures thereof. All of the aforementioned materials have a log P that is less than 3, thus they remain in the water phase of a freshening composition, and wash solutions comprising same longer and are good treating hard surfaces. The more preferred and most preferred of the aforementioned material are particularly preferred as they are effective at counteracting all of the key malodors.

In one aspect of said freshening composition, less than 10%, preferably less than 5%, more preferably less than 1% of said malodor reduction materials and said one or more perfume raw materials, based on total combined weight of malodor reduction materials and said one or more perfume raw materials, comprise an unsaturated aldehyde moiety.

In one aspect of said freshening composition, said malodor reduction materials are not selected from the group consisting of Table 1-3 malodor reduction materials 302; 288; 50; 157; 1017; 888; 64; 1054; 832; 375; 390; 745; 504; 505; 140; 1012; 498; 362; 103; 356; 1074; 908; 1127; 475; 918; 687; 611; 317; 9; 141; 550; 602; 913; 1005; 521; 10; 215; 370; 335; 378; 1121; 360; 565; 1136; 1129; 655; 369; 1065; 914; 757; 601; 478; 889; 891; 358; 973; 162; 554; 522; 312; 125; 26; 418; 92; 586; 1026; 218; 31; 828; 871; 829; 1066; 287; 269; 769; 701; 1118; 70; 946; 142; 109; 108 or mixtures thereof.

In one aspect of said freshening composition, less than 50%, preferably less than 25%, more preferably less than 15% of said malodor reduction materials and said one or more perfume raw materials, based on total combined weight of malodor reduction materials and said one or more perfume raw materials, has a log P≥3, preferably said composition comprises water.

In one aspect of said freshening composition, said composition comprises an adjunct ingredient selected from the group consisting of isoalkanes comprising at least 12 carbon atoms, a compound comprising a quatenary amine moiety, lubricants, additional solvents glycols, alcohols, silicones, preservatives, anti-microbial agents, pH modifiers, a carrier, insect repellants, metallic salts, cyclodextrins, functional polymers, anti-foaming agents, antioxidants, oxidizing agents, chelants and mixtures thereof:

a) preferably said lubricants comprise a material selected from the group consisting of lubricants comprising hydrocarbons, more preferably hydrocarbons that comprise two or branches,
b) preferably compounds comprising a quatenary amine moiety comprise at least 10 carbon atoms.

A device comprising Applicants' freshening compositions, said device being preferably selected from the group consisting of trigger sprayers, manual aerosol sprayers, automatic aerosol sprayers, wick containing devices, fan devices, and thermal drop-on-demand devices, is disclosed.

A method of controlling malodors comprising: contacting a situs comprising a malodor and/or that will become malodorous with a composition selected from the group consisting of the freshening compositions disclosed herein and mixtures thereof is disclosed.

In one aspect of said method, said contacting step comprises contacting said situs with a sufficient amount of the compositions disclosed herein to provide said malodor with, from about 0.1 milligrams (mg) to about 10,000 mg, preferably from about 1 mg to about 5,000 mg most preferably from about 5 mg to about 1000 mg of said sum of malodor reduction materials per square meter of projected surface area of said situs. In one aspect, the lower ranges of malodor reducing materials perform better than higher amounts, and prevent the situs from becoming excessively heavy.

Delivery Systems

The composition of the present invention may be used with a hard surface cleaner, as is commonly used to clean countertops, tables and floors. A suitable floor cleaning liquid is sold by the instant assignee in a replaceable reservoir under the name WetJet. The cleaning solution may particularly be made according to the teachings of commonly assigned U.S. Pat. No. 6,814,088. The reservoir may be used with and dispensed from a floor cleaning implement, in conjunction with a disposable floor sheet. A suitable spray implement is also sold by the instant assignee under the name WetJet. A suitable reservoir and fitment therefor may be made according to the teachings of commonly assigned U.S. Pat. Nos. 6,386,392 and/or 7,172,099. If desired the floor cleaning implement may dispense steam, according to the teachings of jointly assigned US 2013/0319463. Alternatively a refillable reservoir may be utilized.

If desired the composition of the present invention may be used with a pre-moistened sheet. If the cleaning sheet is pre-moistened, it is preferably pre-moistened with a liquid which provides for cleaning of the target surface, such as a floor, but yet does not require a post-cleaning rinsing operation. The cleaning sheet may be loaded with at least 1, 1.5 or 2 grams of cleaning solution per gram of dry substrate, but typically not more than 5 grams per gram. The cleaning solution may comprise a surfactant, such as APG surfactant which minimizes streaking since there is typically not a rinsing operation, according to the teachings of commonly assigned U.S. Pat. No. 6,716,805.

The composition of the present invention may be used for raised hard surfaces, as is sold by the instant assignee under the names Mr. Clean and Mr. Proper. The composition may be dispensed from a trigger sprayer or aerosol sprayer, as are well known in the art. An aerosol sprayer dispenses the composition using propellant pressure, while a trigger sprayer dispenses the composition by pumping the composition under manual actuation. A suitable aerosol dispenser may have a dip tube or bag on valve, and be accord to commonly assigned US 2015/0108163 and/or US 2011/0303766. A suitable trigger sprayer may be accord to commonly assigned U.S. Pat. No. 8,322,631.

Adjunct Materials

While not essential for the purposes of the present invention, the non-limiting list of adjuncts illustrated hereinafter are suitable for use in the instant compositions and may be desirably incorporated in certain aspects of the invention, for example to assist or enhance phase stability of the mixture, to assist or enhance delivery of the freshening composition to fabric, to prevent degradation of the freshening composition by biological contaminants, to add additional benefits, or to modify the aesthetics of the composition as is the case with perfumes, colorants, dyes or the like. The precise nature of these additional components, and levels of incorporation thereof, will depend on the physical form of the composition and the nature of the operation for which it is to be used. Suitable adjunct materials include, but are not limited to, pH buffering agents, solubilizing aids, antimicrobial agents, preservatives, wetting agents, solvents, perfumes or other ingredients.

As stated, the adjunct ingredients are not essential to Applicants' compositions. Thus, certain aspects of Applicants' compositions do not contain one or more of the following adjuncts materials: pH buffering agents, solubilizing aids, antimicrobial agents, preservatives, wetting agents, solvents, perfumes or other ingredients. However, when one or more adjuncts are present, such one or more adjuncts may be present as detailed below.

Buffering Agent

The freshening composition of the present invention may include a buffering agent which may be a carboxylic acid, or a dicarboxylic acid like maleic acid, or a polybasic acid such as citric acid or polyacrylic acid. The acid may be sterically stable, and used in this composition for maintaining the desired pH. The buffering agent may also comprise a base such as triethanolamine, or the salt of an organic acid such as sodium citrate. The freshening composition may have a pH from about 3 to about 8, alternatively from about 4 to about 7, alternatively from about 5 to about 8, alternatively from about 6 to about 8, alternatively about 6 to about 7, alternatively about 7, alternatively about 6.5.

Carboxylic acids such as citric acid may act as metal ion chelants and can form metallic salts with low water solubility. As such, in some embodiments, the freshening composition is essentially free of citric acids. The buffer can be alkaline, acidic or neutral.

Other suitable buffering agents for freshening compositions of the present invention include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl) amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Mixtures of any of the above are also acceptable.

The freshening compositions may contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer

The freshening composition of the present invention may contain a solubilizing aid to solubilize any excess hydrophobic organic materials, particularly some malodor reduction materials of the current invention, perfume materials, and also optional ingredients (e.g., insect repelling agent, antioxidant, etc.) which can be added to the composition, that are not readily soluble in the composition, to form a clear translucent solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

In some embodiments, the freshening composition contains nonionic surfactants, cationic surfactants, and mixtures thereof. In one embodiment, the freshening composition contains ethoxylated hydrogenated castor oil. One type of suitable hydrogenated castor oil that may be used in the present composition is sold as Basophor™, available from BASF.

Freshening compositions containing anionic surfactants and/or detergent surfactants may make fabrics susceptible to soiling and/or leave unacceptable visible stains on fabrics as the solution evaporates off of the fabric. In some embodiments, the freshening composition is free of anionic surfactants and/or detergent surfactants.

When the solubilizing agent is present, it is typically present at a level of from about 0.01% to about 3%, alternatively from about 0.05% to about 1%, alternatively from about 0.01% to about 0.05%, by weight of the freshening composition.

Antimicrobial Compounds

The freshening composition of the present invention may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Streptococcus pyogenes, Salmonella choleraesuis, Escherichia coli, Trichophyton mentagrophytes*, and *Pseudomonas aeruginosa*. In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition of the present invention can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

In one embodiment, a quaternary compound is used. Examples of commercially available quaternary compounds suitable for use in the freshening composition is Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the freshening composition.

Preservatives

The freshening composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the composition is deposited in order to eliminate odors produced by microorganisms. Instead, it is being used to prevent spoilage of the freshening composition in order to increase the shelf-life of the composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives for use in the present invention include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the freshening composition.

The freshening composition may include a wetting agent that provides a low surface tension that permits the composition to spread readily and more uniformly on hydrophobic surfaces like polyester and nylon. It has been found that the aqueous solution, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated aqueous compositions.

Nonlimiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of wetting agents of this type are described in U.S. Pat. No. 5,714,137 and include the Silwet® surfactants available from Momentive Performance Chemical, Albany, N.Y. Exemplary Silwet surfactants are as follows:

| Name | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |
| L-7602 | 3,000; |

and mixtures thereof.

In another aspect of the invention freshening fabric is a restoration of the fabric such as its surface appearance (reduction of wrinkling, improved color appearance, improved or restored fabric shape). Adjunct ingredients that help restore fabric appearance are selected from: water soluble or miscible quaternary ammonium surfactants and water insoluble oil components together with surfactants, emulsifiers, and solvents needed to form a composition that is stable and does not separate. Some nonlimiting preferred emulsifiers are sorbitan esters and sorbitan esters modified with alkylene oxides, such as Tween® 20 (polyoxyethylene (20)sorbitan monolaurate, branched surfactants, like Guerbet alcohols or alkylene oxide modified Guerget alcohols such as Lutensol® XL 70 (Oxirane, 2-methyl-, polymer with oxirane, mono(2-propylheptyl)ether, BASF). It is optional but preferred to have a wetting agent in this aspect of the invention. Wetting agents aid in spreading components and in reducing foaming of the composition during spraying. Some preferred wetting agents include the class of wetting agents known in the art as superwetters. Not to be bound by theory, superwetters pack very efficiently at surfaces resulting in an extremely low equilibrium surface tension. Nonlimiting examples of such surfactants include Surfynols® like Surfynol® 465 and Surfynol® 104PG 50 (Dow Chemicals).

Water Soluble or Miscible Quaternary Ammonium Surfactant:

Typically, minimum levels of the water soluble quat included in the compositions of the present invention are at least about 0.01%, preferably at least about 0.05%, more preferably at least about 0.1% even more preferably at least about 0.2% by weight, based on the total weight of the composition. Typically maximum levels of water soluble quaternary agent included in the composition are up to about 20%, preferably less than about 10%, and more preferably less than about 3% based on the total weight of the composition. Typically, the agent is present in the composition in an amount of about 0.2% to about 1.0%.

Specifically, the preferred water soluble quaternary compounds are dialkly quaternary surfactant compounds. Suitable quaternary surfactants include, but are not limited to, quaternary ammonium surfactants having the formula:

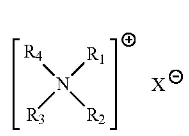

wherein $R_1$ and $R_2$ are individually selected from the group consisting of $C_1$-$C_4$ alkyl, $C_1$-$C_4$ hydroxy alkyl, benzyl, and $—(C_2H_4O)_xH$ where x has a value from about 2 to about 5; X is an anion; and (1) $R_3$ and $R_4$ are each a $C_6$-$C_{14}$ alkyl or (2) $R_3$ is a $C_6$-$C_{18}$ alkyl, and $R_4$ is selected from the group consisting of $C_1$-$C_{10}$ alkyl, $C_1$-$C_{10}$ hydroxy alkyl, benzyl, and $—(C_2H_4O)_xH$ where x has a value from 2 to 5. A preferred asymmetric quaternary compounds for this invention are compounds where R3 and R4 are not identical, and preferably one is branched and the other one is linear.

An example of a preferred asymmetric quaternary compound is ARQUAD HTL8-MS where X is a methyl sulfate ion, R1 and R2 are methyl groups, R3 is a hydrogenated tallow group with <5% mono unsaturation, and R4 is a 2-ethylhexyl group. ARQUAD HTL8-MS is available from Akzo Nobel Chemical of Arnhem, Netherlands.

An example of a suitable symmetric quaternary compound is UNIQUAT 22c50 where X is a carbonate and bicarbonate, R1 and R2 are methyl groups, R3 and R4 are C10 alkyl groups. UNIQUAT 22c50 is a registered trademark of Lonza and in North America is available thru Lonza Incorporated of Allendale, N.J.

Another example of a suitable water soluble quaternary compound is BARQUAT CME-35 which is N-Cetyl Ethyl Morpholinium Ethosulfate available from Lonza and having the following structure:

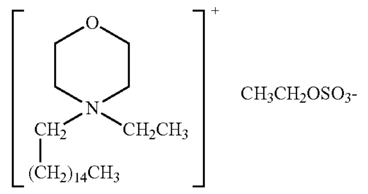

Oil Component

The oil component of the present invention represents a substantially water insoluble material that is incorporated into the composition by way of a microemulsion. The said oil component is a non-perfume raw material and a non-malodor reduction material. Typically the minimum levels of the oil component included in the composition are at least about 0.001%, preferably at least about 0.005%, more preferably at least about 0.01%, and typically maximum levels of oil components are up to about 5%, preferably less than about 3%, more preferably less than 1.5; with typical levels being in the range of about 0.05% to about 1%. The oil component can be a single component or a mixture and usually represents the incorporation of some benefit agent into the composition such as the nonlimiting example benefits softness or wrinkle reduction/release. Typically the oil component comprises substituted or unsubstituted hydrocarbon(s) and the like. For spray products it is preferred that the oil component or mix be a liquid at room temperature for ease of incorporation into the composition and less potential for nozzle clogging on drying.

The oil components of the present invention are substantially water insoluble and form a microemulsion. Substantially water insoluble means the log P of the ingredients are greater than about 1. A log P of about 1 indicates that the component would tend to partition into octanol about 10 times more than water. Some preferred, but non-limiting, components in the oil mixture are branched hydrocarbons and perfumes when perfumes are used.

Aqueous Carrier

The freshening composition of the present invention may include an aqueous carrier. The aqueous carrier which is used may be distilled, deionized, or tap water. Water may be present in any amount for the composition to be an aqueous solution. In some embodiments, water may be present in an amount of about 85% to 99.5%, alternatively about 90% to about 99.5%, alternatively about 92% to about 99.5%, alternatively about 95%, by weight of said freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, the level of monohydric alcohol may about 1% to about 5%, alternatively less than about 6%, alternatively less than about 3%, alternatively less than about 1%, by weight of the freshening composition.

Other Ingredients

The freshening composition may include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference. For example, the freshening composition may include a mixture of volatile aldehydes for neutralizing a malodor and hedonic perfume aldehydes.

Where perfumes, other than the volatile aldehydes in the malodor control component, are formulated into the freshening composition of the present invention, the total amount of perfumes and volatile aldehydes in the malodor control component may be from about 0.015% to about 1%, alternatively from about 0.01% to about 0.5%, alternatively from about 0.015% to about 0.3%, by weight of the freshening composition.

The freshening composition may also include diluents. Exemplary diluents include dipropylene glycol methyl ether, and 3-methoxy-3-methyl-1-butanol, and mixtures thereof.

Optionally, adjuvants can be added to the freshening composition herein for their known purposes. Such adjuvants include, but are not limited to, water soluble metallic salts, including zinc salts, copper salts, and mixtures thereof; antistatic agents; insect and moth repelling agents; colorants; antioxidants; aromatherapy agents and mixtures thereof.

The freshening composition may include other malodor reducing technologies in addition to the malodor reduction composition of the current invention. This may include, without limitation, amine functional polymers, metal ions, cyclodextrins, cyclodextrin derivatives, polyols, oxidizing agents, activated carbon, and combinations thereof.

Perfume Delivery Technologies

The compositions of the present invention may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

In one aspect, the compositions of the present invention may comprise from about 0.001% to about 20%, or from about 0.01% to about 10%, or from about 0.05% to about 5%, or even from about 0.1% to about 0.5% by weight of the perfume delivery technology. In one aspect, said perfume delivery technologies may be selected from the group consisting of: perfume microcapsules, pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, and mixtures thereof:

In one aspect, said perfume delivery technology may comprise microcapsules formed by at least partially surrounding a benefit agent with a wall material. Said benefit agent may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, delta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, the microcapsule may be a perfume microcapsule. In one aspect, one or more types of microcapsules, for example two microcapsules types having different benefit agents may be used.

In one aspect, said perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Air and Fabric Refreshing Delivery Forms

The present composition may be used in a device for the delivery of a volatile material to the atmosphere or on inanimate surfaces (e.g. fabric surfaces as a fabric refresher). Such device may be configured in a variety of ways.

For example, the device may be configured for use as an energized air freshener (i.e. powered by electricity; or chemical reactions, such as catalyst fuel systems; or solar powered; or the like). Exemplary energized air freshening devices include a powered delivery assistance means which may include a heating element, fan assembly, or the like. More particularly, the device may be an electrical wall-plug air freshener as described in U.S. Pat. No. 7,223,361; a battery (including rechargeable battery) powered air freshener having a heating and/or fan element. In energized devices, the volatile material delivery engine may be placed next to the powered delivery assistance means to diffuse the volatile perfume material. The volatile perfume material may be formulated to optimally diffuse with the delivery assistance means.

The device may be configured for use as a non-energized air freshener. An exemplary non-energized air freshener includes a reservoir and, optionally, capillary or wicking means or an emanating surface, to help volatile materials passively diffuse into the air (i.e. without an energized means). A more specific example includes a delivery engine having a liquid reservoir for containing a volatile material and a microporous membrane enclosing the liquid reservoir as disclosed in U.S. Pat. Nos. 8,709,337 and 8,931,711.

The device may also be configured for use as an aerosol sprayer or a non-aerosol air sprayer including traditional trigger sprayers as well as trigger sprayer having a pre-compression and/or buffer system for fluid therein. In this embodiment, the delivery engine can deliver volatile materials upon user demand or programmed to automatically deliver volatile materials to the atmosphere.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

Test Methods

Malodor reduction materials may be separated from mixtures, including but not limited to finished products such as consumer products and identified, by analytical methods that include GC-MS and/or NMR.

Viscosity Test Method

Viscosity is measured using an AR 550 rheometer/viscometer from TA instruments (New Castle, Del., USA), using parallel steel plates of 40 mm diameter and a gap size of 500 μm. The high shear viscosity at 20 $s^{-1}$ is obtained from a logarithmic shear rate sweep from 0.1 $s^{-1}$ to 25 $s^{-1}$ in 3 minutes time at 21° C.

Test Method for Determining Saturation Vapour Pressure (VP)

The saturation Vapour Pressure (VP) values are computed for each PRM in the perfume mixture being tested. The VP of an individual PRM is calculated using the VP Computational Model, version 14.02 (Linux) available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (Log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapour Pressure (VP); Boiling Point (BP); logarithm of the Octanol/Water Partition Coefficient (log P); Odour Detection Threshold (ODT); Malodour Reduction Value (MORV); and/or Universal Malodour Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using winMolconn:

1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
    a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
    a. Note that the winMolconn molecular descriptor labels are case-sensitive.

MORV and Universal MORV Calculation

1.) Input Molecular Descriptor values as determined via the method above into the following four equations:

$$MORV=-8.5096+2.8597\times(dxp9)+1.1253\times(knotpv)-0.34484\times(e1C2O2)-0.00046231\times(idw)+3.3509\times(idcbar)+0.11158\times(n2pag22) \quad a)$$

$$MORV=-5.2917+2.1741\times(dxvp5)-2.6595\times(dxvp8)+0.45297\times(e1C2C2d)-0.6202\times(c1C2O2)+1.3542\times(CdCH2)+0.68105\times(CaasC)+1.7129\times(idcbar) \quad b)$$

$$MORV=-0.0035+0.8028\times(SHCsatu)+2.1673\times(xvp7)-1.3507\times(c1C1C3d)+0.61496\times(c1C1O2)+0.00403\times(idc)-0.23286\times(nd2). \quad c)$$

$$MORV=-0.9926-0.03882\times(SdO)+0.1869\times(Ssp3OH)+2.1847\times(xp7)+0.34344\times(e1C3O2)-0.45767\times(c1C2C3)+0.7684\times(CKetone) \quad d)$$

Equation a) relates a material's effectiveness in reducing the malodor trans-3-methyl-2-hexenoic acid (carboxylic acid based malodors)

Equation b) relates a material's effectiveness in reducing the malodor trimethylamine (amine based malodors)

Equation c) relates a material's effectiveness in reducing the malodor 3-mercapto-3-methylhexan-1-ol (thiol based malodors)

Equation d) relates a material's effectiveness in reducing the malodor skatole (indole based malodors)

2.) For purpose of the present application, a material's MORV is the highest MORV value from equations 1.)a) through 1.)d).

3.) If all MORVvalues from equations 1.)a) through 1.)d) above are greater than 0.5, the subject material has a Universal MORV.

Method for Assigning Fragrance Fidelity Index (FFI) and the Blocker Index (BI) for a Malodor Reduction Compound Blocker materials suitable for use in consumer products of the present invention are chosen for their ability to decrease malodor, while not interfering with perception of a fragrance. Material selection is done by assigning two indices to a test sample material from two reference scales in order to rank odor strengths. The two reference scales are the Fragrance Fidelity Index (FFI) scale and the Blocker Index (BI) scale. The FFI ranks the ability of the test sample material to impart a perceivable odor which could cause interference when combined with another fragrance and the BI ranks the ability of the test sample material to reduce malodor perception. The two methods for assigning the indices to a test sample on the FFI and the BI reference scales are given below.

Method for Assigning the FFI to Test Samples

The first step in the method for assigning an FFI to the test samples on the FFI reference scale is to create the FFI reference swatches. The swatches for the scale are created by treating clean fabrics swatches with a known amount of a known concentration of an ethyl vanillin solution. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the FFI Reference Swatches

Make three solutions of ethyl vanillin using a 50%/50% EtOH/water as the diluent at the following concentrations: 25 ppm, 120 ppm and 1000 ppm. Pipette 13 μL of each of the three solutions into the middle of a clean swatch resulting in about a 1 cm diameter of the solution in the middle of the swatch. This will create a sensory scale of three swatches with three different odor levels based on the concentration of the solution pipetted onto the swatch. After drying for 30 minutes in a vented hood, the swatches are wrapped in aluminum foil to prevent odor contamination to the treated swatch. A clean untreated swatch is also included as the lowest anchor point of reference for odor strength on the FFI scale. The FFI reference scale swatches should be used within 0.5 to 12 hours and discarded after 12 hours. The swatches are used as scale anchor points when graders evaluate a test sample(s) and are assigned a Fragrance Fidelity Index (FFI) as show in Table 7.

At least four perfumers/expert graders are used to rank the ethyl vanillin swatches in the FFI scale. The perfumer/expert grader needs to demonstrate adequate discrimination on the scale. The perfumer/expert panel is asked to rank order swatches according to a scale between 0 and 3. The panel must demonstrate statistical differences between the swatches as seen in Table 7.

TABLE 7

Results FFI of reference swatches from six perfumers/expert graders.

| | | Expert Grader | | | | | | | Std |
|---|---|---|---|---|---|---|---|---|---|
| FFI | Swatch | 1 | 2 | 3 | 4 | 5 | 6 | Ave | Dev. |
| 0 | Control: stripped swatch NIL ethyl vanillin | 0 | 0 | 0.5 | 0 | 0 | 0 | 0.08 | 0.2 |
| 1 | Stripped swatch with 13 μL 25 ppm ethyl vanillin | 0.5 | 0.5 | 0.5 | 1.5 | 0.5 | 1.0 | 0.75 | 0.4 |
| 2 | Stripped swatch with 13 μL 120 ppm ethyl vanillin | 2.0 | 1.5 | 1.5 | 2.0 | 2.0 | 2.0 | 1.8 | 0.2 |
| 3 | Stripped swatch with 13 μL 1000 ppm ethyl vanillin | 3.0 | 2.0 | 3.0 | 3.0 | 3.0 | 3.0 | 2.8 | 0.4 |

The expert graders must demonstrate a full range of 2.5 over the 4 swatches to be acceptably discriminating. Grader 2 in table 1 has a range of only 2 and is eliminated from the panel. The panel of expert graders must also demonstrated the ability to statistically discriminate between swatches in the scale.

TABLE 8

This table demonstrates acceptable expert graders with an acceptable range and the panel meets the requirement for discriminating statistics.

| | | Expert Grader | | | | | | Std |
|---|---|---|---|---|---|---|---|---|
| FFI | Swatch | 1 | 3 | 4 | 5 | 6 | Ave | Dev. |
| 0 | Control: stripped swatch NIL ethyl vanillin | 0 | 0.5 | 0 | 0 | 0 | 0.08 | 0.2 |
| 1 | Stripped swatch with 13 μL 25 ppm ethyl vanillin | 0.5 | 0.5 | 1.5 | 0.5 | 1.0 | 0.80 | 0.4 |
| 2 | Stripped swatch with 13 μL 120 ppm ethyl vanillin | 2.0 | 1.5 | 2.0 | 2.0 | 2.0 | 1.9 | 0.2 |
| 3 | Stripped swatch with 13 μL 1000 ppm ethyl vanillin | 3.0 | 3.0 | 3.0 | 3.0 | 3.0 | 3.0 | 0.0 |

The reference swatches represent the 0, 1, 2, and 3 FFIs on the FFI reference scale, Table 9. The expert grader should familiarize them self with the strength of the odor on the FFI reference swatches by sniffing each one starting at 0 (the lowest odor strength) and ending at 3 (the highest odor strength). This should be done prior to evaluating the test sample material treated swatch.

TABLE 9

Swatch treatments comprising the Fragrance Fidelity Index (FFI) reference scale

| Swatch treatment | Conc. of ethyl vanillin | FFI |
|---|---|---|
| Clean fabric swatch w/13 μL ethyl vanillin | 1000 ppm ethyl vanillin | 3 |
| Clean fabric swatch w/13 μL ethyl vanillin | 120 ppm ethyl vanillin | 2 |
| Clean fabric swatch w/13 μL ethyl vanillin | 25 ppm ethyl vanillin | 1 |
| Clean fabric swatch NIL ethyl vanillin | NIL ethyl vanillin | 0 |

Making Swatches Treated with the Test Material

A clean swatch is treated with 13 μL of a known concentration of a test sample material resulting in an about 1 cm of the solution on the clean swatch. Just like the reference swatches, the test sample material swatch is dried in a vented hood for 30 minutes and then wrapped in aluminum foil to prevent contamination. The test material swatches and the FFI reference swatches should be made within 2 hrs of each other. The test material swatch must be used within 0.5 to 12 hours and discarded after 12 hours.

Assigning the FFI to the Test Material

At least two perfumers/expert graders are used to assign an FFI grade to a test sample. The perfumer/expert grader smells the test sample swatch by holding that swatch 1 inch from their nose with their nose centered over the area where the test sample was pipetted on to the fabric and then assigns the test sample an FFI grade using the FFI reference scale anchor swatches as references. The test sample swatch is assigned an FFI grade at or between numbers on the FFI scale shown in Table 9. In cases where the test sample material is graded greater than 3, the test material is not a blocker material or the concentration of the material needs to be lowered and reevaluated to determine if a lower level has a malodor blocker functionality.

Method for Assigning the BI to Test Sample

The first step in the method for assigning a BI to a test sample material on the BI reference scale is to create the BI reference swatches. The swatches for the scale are created by treating clean fabrics swatches with a known amount of a known volume of isovaleric acid solution at a known concentration. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the BI Reference Swatches

Make one solution of 0.08% isovaleric acid using 50%/50% EtOH/water as the diluent. The BI scale contains one clean swatch with no malodor applied. Three other swatches each have a different volume of the 0.08% isovaleric acid applied. Pipette 2 μL of the 0.08% isovaleric acid solution to one clean swatch, 5 μL of the 0.08% isovaleric acid solution to the next swatch and 20 μL of isovaleric acid to the final clean swatch. These solutions are pipetted to the middle of the swatches. This will create a sensory scale of three swatches with three different odor levels based on the volume of the 0.08% isovaleric acid solution pipetted onto the swatch. After drying for 30 minutes in a vented hood, the swatches are wrapped in aluminum foil to prevent odor contamination to the treated swatch. A clean untreated swatch is also included as the lowest anchor point of reference for malodor strength on the BI scale. The BI reference scale swatches should be used within 0.5 to 12 hours and discarded after 12 hours. The swatches are used as scale anchor points when graders evaluate a test sample(s) and are assigned a Blocker Index (BI) as show in Table 12.

At least four perfumers/expert graders are used to rank the isovaleric acid swatches in the BI scale. The perfumer/expert grader needs to demonstrate adequate discrimination on the scale. The perfumer/expert grader is asked to rank order swatches according to a scale between 0 and 3. The panel of graders must demonstrate statistical differences between the swatches as seen in Table 10.

TABLE 10

Results from six perfumers/expert graders to create the BI scale.

| BI | Swatch | Expert Grader 1 | 2 | 3 | 4 | 5 | Ave | Std Dev. |
|---|---|---|---|---|---|---|---|---|
| 0 | Control: stripped swatch NIL isovaleric acid | 0 | 0 | 0 | 0 | 0 | 0 | 0 |
| 1 | Stripped swatch with 2 μL 0.08% isovaleric acid | 0.5 | 2.0 | 1.0 | 1.0 | 0.5 | 1.0 | 0.5 |
| 2 | Stripped swatch with 5 μL 0.08% isovaleric acid | 2.0 | 2.5 | 2.0 | 2.0 | 2.0 | 2.1 | 0.2 |
| 3 | Stripped swatch with 20 μL 0.08% isovaleric acid | 3.0 | 3.0 | 3.0 | 3.0 | 2.5 | 2.8 | 0.2 |

The expert graders must demonstrate a full range of 2.5 over the 4 swatches to be acceptably discriminating. The panel of expert graders must also demonstrated the ability to statistically discriminate between swatches in the scale. Expert grader #2 did not demonstrate the ability to discriminate between the swatches and is eliminated from the panel, see Table 11.

TABLE 11

This table demonstrates acceptable expert graders with an acceptable range and the panel meets the requirement for discriminating statistics.

| BI | Swatch | Expert Grader 1 | 3 | 4 | 5 | Ave | Std Dev. |
|---|---|---|---|---|---|---|---|
| 0 | Control: stripped swatch NIL isovaleric acid | 0 | 0 | 0 | 0 | 0 | 0 |
| 1 | Stripped swatch with 2 μL 0.08% isovaleric acid | 0.5 | 1.0 | 1.0 | 0.5 | 0.8 | 0.3 |
| 2 | Stripped swatch with 5 μL 0.08% isovaleric acid | 2.0 | 2.0 | 2.0 | 2.0 | 2.0 | 0 |
| 3 | Stripped swatch with 20 μL 0.08% isovaleric acid | 3.0 | 3.0 | 3.0 | 2.5 | 2.9 | 0.2 |

The reference swatches represent the 0, 1, 2, and 3 BIs on the BI reference scale, Table 12. The expert grader should familiarizes him/herself with the strength of the odor on the BI reference swatches by sniffing each one starting at 0 (the lowest odor strength) and ending at 3 (the highest odor strength). This should be done prior to evaluating the swatch treated with the test material.

TABLE 12

Swatch treatments comprising the Blocker Index (BI) reference scale.

| Swatch/treatment | Wt of isovaleric acid | BI |
|---|---|---|
| Clean fabric swatch w/20 μL 0.08% isovaleric acid | 16 mg isovaleric acid | 3 |
| Clean fabric swatch w/5 μL 0.08% isovaleric acid | 4 mg isovaleric acid | 2 |
| Clean fabric swatch w/2 μL 0.08% isovaleric acid | 1.6 mg isovaleric acid | 1 |
| Clean fabric swatch NIL isovaleric acid | NIL isovaleric acid | 0 |

Making the Malodorous Swatch and Treating it with a Test Material

To evaluate the BI, the test material is applied to a malodorous swatch to determine how well the test material blocks the malodor. The malodorous swatch is made by treating a clean swatch with 20 μL of a 0.08% solution of isovaleric acid. Dry the malodorous swatch treated with isovaleric acid in a vented hood for 30 minutes. After drying the malodorous swatch a known concentration of test material solution, between 1 ppm and 100 ppm is pipetted onto the malodorous swatch. Apply the test material solution right on top of the spot where the isovaleric acid solution was applied making an about 1 cm diameter spot. Just like the BI reference swatches, the isovaleric acid+test material swatch is dried in a vented hood for 30 minutes and then wrapped in aluminum foil to prevent contamination. The isovaleric acid+test material swatches and the BI reference swatches should be made within 2 hrs of each other. The isovaleric acid+test material swatch must be used between 1-12 hours just like the reference swatches. It is sometimes necessary to evaluate several levels of the test material between about 1 and about 100 ppm to determine the BI.

Assigning the BI to the Test Material

At least two perfumers/expert graders are used to assign the BI to the test sample. The expert grader smells the isovaleric acid+test material swatch by holding that swatch one inch from their nose with their nose centered over the area where the test sample was pipetted on to the fabric and then assigns the isovaleric acid+test material swatch a BI based on ranking its odor strength against the odor strength of the swatches in the BI reference scale. The test sample swatch is assigned a BI at or between numbers on the BI in table. In cases where the isovaleric acid+test material swatch odor is greater than 3 on the BI reference scale, this indicates the material is not a blocker or the concentration of the test material needs to be lowered to achieve its blocker functionality.

Malodor Reduction Compounds with FFI and BI Grades Based on the Aforementioned

| Table Ref # | CAS# | log P | Name | Conc | FFI | BI |
|---|---|---|---|---|---|---|
| 281 | 54830-99-8 | 3.11 | 3a,4,5,6,7,7a-hexahydro-4,7-methano-1H-indenyl acetate | 10 ppm | 0 | 2.0 |
| | | | | 50 ppm | 0.5 | 2.0 |
| 677 | 139504-68-0 | 3.75 | 1-((2-(tert-butyl)cyclohexyl)oxy)butan-2-ol | 10 ppm | 0 | 2.3 |
| | | | | 50 ppm | 1.8 | 2.0 |
| 962 | 55066-48-3 | 3.17 | 3-methyl-5-phenylpentan-1-ol | 10 ppm | 0 | 2.3 |
| | | | | 50 ppm | 0.5 | 1.7 |
| 261 | 173445-65-3 | 3.29 | 3-(3,3-dimethyl-2,3-dihydro-1H-inden-5-yl)propanal | 10 ppm | 0 | 1.8 |
| | | | | 50 ppm | 1.3 | 1.3 |

-continued

| Table Ref # | CAS# | log P | Name | Conc | FFI | BI |
|---|---|---|---|---|---|---|
| 1139 | 87731-18-8 | 2.11 | (Z)-cyclooct-4-en-1-yl methyl carbonate | 10 ppm | 0 | 2.0 |
| | | | | 50 ppm | 1.0 | 2.7 |
| | 4430-31-3 | 1.43 | 3,4,4a,5,6,7,8,8a-octahydrochromen-2-one | 10 ppm | 0 | 2.0 |
| | | | | 50 ppm | 0 | 2.0 |
| 204 | 40379-24-6 | 3.89 | 7-methyloctyl acetate | 10 ppm | 0 | 2.0 |
| | | | | 50 ppm | 0 | 2.7 |
| 1005 | 93981-50-1 | 5.59 | ethyl (2,3,6-trimethylcyclohexyl)carbonate | 50 ppm | 0.5 | 2.6 |
| 391 | 106-33-2 | 5.73 | Ethyl laurate | 50 ppm | 0.3 | 2.2 |
| 1148 | 1139-30-6 | 4.06 | Caryophyllene Oxide | 50 ppm | 0.5 | 2.3 |
| 524 | 13877-91-3 3338-55-4 | 4.31 | 3,7-Dimethyl-1,3,6-Octatriene(cis-β ocimene 70%) | 50 ppm | 0 | 2.8 |
| 1149 | 23787-90-8 | 4 | 1,3,4,6,7,8alpha-hexahydro-1,1,5,5-tetramethyl-2H-2,4alpha-methanophtalen-8(5H)-one | 10 ppm | 0 | 1.5 |
| | | | | 50 ppm | 0.8 | 2.3 |
| | 112-42-5 | 4.62 | Undecanol | 50 ppm | 0.8 | 2.3 |
| 174 | 112-53-8 | 5.17 | 1-dodecanol | 50 ppm | 0.5 | 2.3 |
| | 98-52-2 | 2.78 | 4-tert-butyl cyclohexane | 10 ppm | 0 | 2.0 |
| | | | | 50 ppm | 0.3 | 2.0 |
| 109 | 112-39-0 | 6.41 | Methyl palmitate | 10 ppm | | 2.0 |

Malodor Control Compounds with Improved Performance at Lower Levels.

Below are some non-limiting examples of preferred behavior by which the malodor control compound gives improved malodor control at lower concentration. These nonlimiting data provide additional compelling data that malodor is being blocked, not masked.

| Table Ref # | CAS# | Name | Conc | FFI | BI |
|---|---|---|---|---|---|
| N/A | 68912-13-0 | 8,8-dimethyl-3a,4,5,6,7,7a-hexahydro-1H-4,7-methanoinden-6-yl propionate | 10 ppm | 0 | 1.5 |
| | | | 50 ppm | 0 | 2.2 |
| N/A | TBD | 4,8-dimethyl-1-(methylethyl)-7-oxybiciclo [4.3.0]nonane | 10 ppm | | 2.0 |
| | | | 50 ppm | 0.3 | 2.2 |

about 0.001 Fragrance Fidelity 9999999999999999999999999999999999999999999999999 9999999999999999999999999999999999999999999999999 9999999999999999999999999999999999999999999999999 999999999999999999999999999999999999999999999999 99999

Retesting Malodor Reduction Compounds at Lower Levels.

The example below demonstrates that while a malodor control compound could fail to demonstrate odor blocking (BI>2.5) at a higher concentration it should be retested at a lower concentration to determine if it passes.

| Table Ref # | CAS # | Name | Conc | FFI | BI |
|---|---|---|---|---|---|
| N/A | 173445-65-3 | 1H-Indene-5-propanal, 2,3-dihydro-3,3-dimethyl- | 10 ppm | 0 | 1.5 |
| | | | 50 ppm | 0.5 | 2.7 |

EXAMPLE 1

Compositions Comprising Malodor Reduction Compounds

In the present invention blends enable more potent malodor reduction because blends are useful at a higher % of the product composition before becoming olfactively noticeable. Below are non-limiting examples of malodor reduction compounds.

| | | % wt Active | | | | |
|---|---|---|---|---|---|---|
| Component | CAS# | A | B | C | D | E |
| 2,2,8,8-tetramethyl-octahydro-1H-2,4a-methanonapthalene-10-one | 29461-14-1 | 35-45 | 15-25 | 5-20 | 10-30 | 15-25 |
| 1H-Indene-ar-propanal,2,3-dihydro-1,1-dimethyl- | 300371-33-9 | 10-20 | 1-30 | NIL | 5-10 | 1-5 |
| Hexadecanoic acid, (2E)-3,7-dimethyl-2,6-octadien-1-yl ester | 3681-73-0 | 35-45 | 10-25 | NIL | 30-40 | 35-50 |
| 1-Pentanol-3-methyl-5-phenyl | 55066-48-3 | 10-20 | 10-25 | 2-10 | 5-17 | 10 |
| 4,7-Methano-1H-inden-5-ol, 3a,4,5,6,7,7a-hexahydro-, 5-acetate | 171102-41-3 | 0-5 | 10-25 | NIL | 1-6 | 1-5 |
| 4,8-dimethyl-1-(methylethyl)-7-oxybiciclo [4.3.0]nonane | N/A | 0-5 | NIL | NIL | NIL | 1-5 |
| (3Z)-3,7-dimethylocta-1,3,6-triene | 3338-55-4 | NIL | NIL | 10-20 | 2-5 | NIL |
| 1H-Indene-5-propanal, 2,3-dihydro-3,3-dimethyl- | 173445-65-3 | NIL | NIL | NIL | 7.5-16 | 1-15 |
| 3,4,4a,5,6,7,8,8a-octahydrochromen-2-one | 4430-31-3 | NIL | NIL | NIL | 3-7 | 1-15 |

-continued

| Component | CAS# | % wt Active A | B | C | D | E |
|---|---|---|---|---|---|---|
| 1-(2-tert-butylcyclohexyl)oxybutan-2-ol | 139504-68-0 | NIL | NIL | NIL | 0.25-1.5 | NIL |
| ethyl (2,3,6-trimethylcyclohexyl)carbonate | 93981-50-1 | NIL | NIL | 15-30 | NIL | 2 |
| benzyl 2-hydroxypropanoate | 2051-96-9 | NIL | NIL | 2-5 | NIL | NIL |
| (3,5-dimethylcyclohex-3-en-1-yl)methanol | 67634-16-6 | NIL | NIL | 5-30 | NIL | NIL |
| 2-Dodecanol | 10203-28-8 | NIL | 0.25-1 | NIL | 0.5-3 | NIL |

EXAMPLE 2

Compositions Comprising Malodor Reduction Compounds

| Ingredient | CAS # | % wt Active A | B | C | B | D | E |
|---|---|---|---|---|---|---|---|
| (E)-1-(2,6,6-trimethyl-1-cyclohex-2-enyl)pent-1-en-3-one | 127-42-4 | 4 | 8 | 2 | 8 | 3 | 2 |
| ethyl dodecanoate | 106-33-2 | NIL | 1 | NIL | 3 | NIL | NIL |
| 3a,4,5,6,7,7a-hexahydro-1H-4,7-methanoinden-1-yl propanoate | 68912-13-0 | 8 | 30 | 1 | 4 | 1 | 3.5 |
| [1R-(1R*,4R*,6R*,10S*)]-4,12,12-trimethyl-9-methylene-5-oxatricyclo[8.2.0.04,6]dodecane | 1139-30-6 | NIL | 0.3 | 2 | 0.5 | NIL | 0.5 |
| (8E)-cyclohexadec-8-en-1-one | 3100-36-5 | NIL | 5 | NIL | 7 | NIL | NIL |
| 3,5,5-trimethylhexyl acetate | 58430-94-7 | 25 | 15 | 50 | 35 | 60 | 56 |
| ethyl (2,3,6-trimethylcyclohexyl)carbonate | 93981-50-1 | NIL | 1 | NIL | 5 | NIL | NIL |
| 2,4-dimethyl-4,4a,5,9b-tetrahydroindeno[1,2-d][1,3]dioxine | 27606-09-3 | 25 | 10 | 15 | 15 | 16 | 15 |
| 2,2,7,7-tetramethyltricyclo[6.2.1.01,6]undecan-5-one | 23787-90-8 | 8 | 9 | 5 | 7 | 5 | 5 |
| (3,5-dimethylcyclohex-3-en-1-yl)methanol | 67634-16-6 | NIL | 0.7 | NIL | 0.5 | NIL | NIL |
| 3-(7,7-dimethyl-4-bicyclo[3.1.1]hept-3-enyl)-2,2-dimethylpropanal | 33885-52-8 | 30 | 20 | 25 | 15 | 15 | 18 |
| Total | | 100 | 100 | 100 | 100 | 100 | 100 |

EXAMPLE 3

Malodor Reduction Composition

| Ingredient | CAS # | % wt Active A | B | C |
|---|---|---|---|---|
| 5-Cyclohexadecen-1-One | 37609-25-9 | 15.0 | 2.00 | 2.00 |
| decahydro-2,2,7,7,8,9,9-heptamethylindeno(4,3a-b)furan | 476332-65-7 | 0.005 | 0.01 | 0.01 |
| 2,3-Dihydro-5,6-dimethoxy-2-(4-piperidinylmethylene)-1H-inden-1-one | 33704-61-9 | 0.3 | 0.5 | 0.5 |
| Cedryl Methyl Ether | 19870-74-7 | 6.0 | 10.0 | 4.0 |
| Trans-4-Decenal | 65405-70-1 | 0.005 | 0.002 | 0.002 |
| Decyl Aldehyde | 112-31-2 | 3.74 | 2.0 | 2.0 |
| 3-methyl cyclopentadecenone | 63314-79-4 | 0.4 | 1.0 | 1.0 |
| Diphenyl Oxide | 101-84-8 | 0.5 | 1.0 | 1.0 |
| 3a,4,5,6,7,7a-hexahydro-4,7-methano-1H-indenyl acetate | 54830-99-8 | 5.0 | 8.0 | 8.0 |
| 3a,4,5,6,7,7a-hexahydro-1H-4,7-methanoinden-1-yl propanoate | 68912-13-0 | 6.0 | 8.0 | 8.0 |

-continued

| Ingredient | CAS # | % wt Active A | B | C |
|---|---|---|---|---|
| 2-(5-methyl-2-propan-2-yl-8-bicyclo[2.2.2]oct-5-enyl)-1,3-dioxolane | 68901-32-6 | 10.0 | 15.0 | 15.0 |
| (E)-3,7-dimethyl-2,6-octadienylhexadecanoate | 3681-73-0 | 10.0 | 10.0 | 16.0 |
| Iso Nonyl Acetate | 58430-94-7 | 6.65 | 8.0 | 3.0 |
| 2,2,7,7-tetramethyltricyclo[6.2.1.01,6]undecan-5-one | 23787-90-8 | 10.0 | 8.0 | 8.0 |
| (1-Methyl-2-(1,2,2-trimethylbicyclo[3.1.0]-hex-3-ylmethyl)cyclopropyl)methanol | 198404-98-7 | 0.1 | 0.3 | 0.3 |
| Lauric Aldehyde | 112-54-9 | 0.625 | 1.0 | 0.7 |
| Methyl Iso Eugenol | 93-16-3 | 18.000 | 10.0 | 13.0 |
| Methyl hexadecanoate | 112-39-0 | 3.000 | 10.0 | 12.0 |
| 2,3-dihydro-1,1-1H-dimethyl-indene-ar-propanal | 300371-33-9 | 0.400 | 0.0 | 0.3 |
| 4-tert-butylcyclohexanol | 98-52-2 | 0.400 | 0.1 | 0.1 |
| 2-isobutyl-4-hydroxy-4-methyltetrahydropyran | 63500-71-0 | 1.600 | 2.0 | 2.0 |
| Undecyl Aldehyde | 112-44-7 | 1.725 | 2.888 | 1.888 |
| Undecylenic Aldehyde | 112-45-8 | 0.550 | 0.2 | 1.2 |
| Total | | 100 | 100.0 | 100.0 |

EXAMPLE 4

Malodor Reducing Compositions

| Ingredients | CAS# | % wt Active A | B | C | D |
|---|---|---|---|---|---|
| 2,2,7,7-tetramethyltricyclo(6.2.1.0(1,6))-undecan-5-one | 23787-90-8 | 40 | 20 | 20 | NIL |
| 3-(3,3-dimethyl-2,3-dihydro-1H-inden-5-yl)propanal | 173445-65-3 | 10 | 7.5 | 10 | NIL |
| (E)-3,7-dimethylocta-2,6-dien-1-yl palmitate | 3681-73-0 | 40 | 40 | NIL | NIL |
| 3-methyl-5-phenylpentan-1-ol | 55066-48-3 | 10 | 10 | 10 | NIL |
| 3a,4,5,6,7,7a-hexahydro-4,7-methano-1H-inden-(5 and 6)-yl acetate | 5413-60-5 | NIL | 4 | 20 | NIL |
| 3-(6,6-dimethylbicyclo[3.1.1]hept-2-en-2-yl)-2,2-dimethylpropanal | 33885-52-8 | NIL | 10.000 | NIL | NIL |
| 3,4,4a,5,6,7,8,8a-octahydrochromen-2-one | 4430-31-3 | NIL | 5.000 | NIL | NIL |
| (E)-3,7-dimethylocta-1,3,6-triene | 3338-55-4 | NIL | 3.000 | NIL | NIL |
| 1-((2-(tert-butyl)cyclohexyl)oxy)butan-2-ol | 139504-68-0 | NIL | 0.500 | NIL | NIL |
| 2,2,7,7-tetramethyltricyclo(6.2.1.0(1,6))-undecan-5-one | 23787-90-8 | NIL | NIL | 20.000 | NIL |
| 7-methyloctyl acetate | 58430-94-7 | NIL | NIL | 40.000 | NIL |
| 1-((2-(tert-butyl)cyclohexyl)oxy)butan-2-ol | 139504-68-0 | to 100 | to 100 | to 100 | 100 |

EXAMPLE 5

Malodor Reducing Compositions

| Ingredients | CAS# | % wt Active |
|---|---|---|
| 5-Cyclohexadecen-1-One | 37609-25-9 | 2.6 |
| 2,2,7,7,8,9,9-heptamethyldecahydroindeno[4,3a-b]furan | 647828-16-8 | 0.005 |
| 1,1,2,3,3-pentamethyl-1,2,3,5,6,7-hexahydro-4H-inden-4-one | 33704-61-9 | 0.3 |
| (3R,3aR,6S,7S,8aS)-6-methoxy-3,6,8,8-tetramethyloctahydro-1H-3a,7-methanoazulene | 19870-74-7 | 6 |

-continued

| Ingredients | CAS# | % wt Active |
|---|---|---|
| dodecanenitrile | 2437-25-4 | 0.06 |
| Trans 4-Decenal | 65405-70-1 | 0.001 |
| decanal | 112-31-2 | 3 |
| (E)-3-methylcyclopentadec-4-en-1-one | 82356-51-2 | 0.4 |
| oxydibenzene | 101-84-8 | 0.5 |
| Dipropylene Glycol | 25265-71-8 | 0.054 |
| 3a,4,5,6,7,7a-hexahydro-4,7-methano-1H-inden-(5 and 6)-yl acetate | 54830-99-8 | 4 |
| 3-(2-ethylphenyl)-2,2-dimethylpropanal | 67634-15-5 | 3 |
| 3-(3-isopropylphenyl)butanal | 125109-85-5 | 0.6 |
| 8,8-dimethyl-3a,4,5,6,7,7a-hexahydro-1H-4,7-methanoinden-6-yl propionate | 68912-13-0 | 6 |

-continued

| Ingredients | CAS# | % wt Active |
|---|---|---|
| 2-(8-isopropyl-6-methylbicyclo[2.2.2]oct-5-en-2-yl)-1,3-dioxolane | 68901-32-6 | 10 |
| d E)-3,7-dimethylocta-2,6-dien-1-yl palmitate | 3681-73-0 | 10 |
| 7-methyloctyl acetate | 40379-24-6 | 3 |
| 2,2,7,7-tetramethyltricyclo(6.2.1.0(1,6))-undecan-5-one | 23787-90-8 | 10 |
| (1-methyl-2-((1,2,2-trimethylbicyclo[3.1.0]hexan-3-yl)methyl)cyclopropyl)methanol | 198404-98-7 | 0.1 |
| dodecanal | 112-54-9 | 0.6 |
| Linalyl Benzoate | 126-64-7 | 1.74 |
| 4-(tert-butyl)cyclohexyl acetate | 32210-23-4 | 4 |
| octahydro-1H-4,7-methanoindene-1-carbaldehyde | 30772-79-3 | 0.26 |
| methyl 2-(3-oxo-2-pentylcyclopentyl)acetate | 24851-98-7 | 4.15 |
| (Z)-1,2-dimethoxy-4-(prop-1-en-1-yl)benzene | 93-16-3 | 18.23 |
| Methyl Palmitate | 112-39-0 | 3 |
| 3-(3,3-dimethyl-2,3-dihydro-1H-inden-5-yl)propanal | 300371-33-9 | 0.4 |
| 4-tert-butyl cyclohexanol | 98-52-2 | 0.05 |
| 3-methyl-5-phenylpentan-1-ol | 55066-48-3 | 3.5 |
| 2-isobutyl-4-methyltetrahydro-2H-pyran-4-ol | 63500-71-0 | 1.6 |
| (E)-4-methyldec-3-en-5-ol | 81782-77-6 | 0.8 |
| undecanal | 112-44-7 | 1.7 |
| undec-10-enal | 112-45-8 | 0.35 |

EXAMPLE 6

Malodor Reducing Compositions

| Ingredients | CAS# | % wt Active |
|---|---|---|
| (3R,3aR,6S,7S,8aS)-6-methoxy-3,6,8,8-tetramethyloctahydro-1H-3a,7-methanoazulene | 19870-74-7 | 2.00 |
| 1-(1,2,3,4,5,6,7,8-octahydro-2,3,8,8,-tetramethyl-2-naphthyl)ethan-1-one. | 54464-57-2 | 15.00 |
| Oxacyclohexadec-12-en-2-one, (12E)- | 1118-80-2 | 15.00 |
| 5-cyclohexadecenone | 37609-25-9 | 16.50 |
| 4,8-dimethyl-2-(propan-2-ylidene)-1,2,3,3a,4,5,6,8a-octahydroazulen-6-yl acetate | 117-98-6 | 5.00 |
| isopropyl tetradecanoate | 110-27-0 | 12.25 |
| (Z)-4,11,11-trimethyl-8-methylenebicyclo[7.2.0]undec-3-en-5-yl acetate | 32214-91-8 | 3.50 |
| (E)-cycloheptadec-9-en-1-one | 542-46-1 | 14.00 |
| (E)-cyclohexadec-8-en-1-one | 3100-36-5 | 14.00 |
| 4-((2R)-1,7,7-trimethylbicyclo[2.2.1]heptan-2-yl)cyclohexan-1-ol | 66072-32-0 | 2.75 |

EXAMPLE 7

Malodor Reducing Compositions

The following malodor reduction malodor reduction compositions are made by combining the listed ingredients. All ingredients are in weight percent of the total malodor reduction composition.

| | | % wt Active | | | | | |
|---|---|---|---|---|---|---|---|
| Ingredient | CAS # | A | B | C | D | E | F |
| (E)-1-(2,6,6-trimethyl-1-cyclohex-2-enyl)pent-1-en-3-one | 127-42-4 | 2-8 | 4-10 | 2-6 | 4-10 | 3-6 | 1-5 |
| ethyl dodecanoate | 106-33-2 | NIL | 1-5 | NIL | 2-7 | NIL | NIL |
| 3a,4,5,6,7,7a-hexahydro-1H-4,7-methanoinden-1-yl propanoate | 68912-13-0 | 7-12 | 15-45 | 1-3 | 2-5 | 0.5-3 | 1-7 |
| [1R-(1R*,4R*,6R*,10S*)]-4,12,12-trimethyl-9-methylene-5-oxatricyclo[8.2.0.04,6]dodecane | 1139-30-6 | NIL | 0.1-3 | 2-5 | 0.1-1 | NIL | 0.5-1 |
| (8E)-cyclohexadec-8-en-1-one | 3100-36-5 | NIL | 5-7 | NIL | 5-7 | NIL | NIL |
| 3,5,5-trimethylhexyl acetate | 58430-94-7 | 15-30 | 15-20 | 35-50 | 35-50 | 40-60 | 40-60 |
| ethyl (2,3,6-trimethylcyclohexyl)carbonate | 93981-50-1 | NIL | 1-3 | NIL | 5-7 | NIL | NIL |
| 2,4-dimethyl-4,4a,5,9b-tetrahydroindeno[1,2-d][1,3]dioxine | 27606-09-3 | 10-25 | 10-25 | 10-25 | 10-25 | 10-25 | 10-25 |
| 2,2,7,7-tetramethyltricyclo[6.2.1.01,6]undecan-5-one | 23787-90-8 | 3-9 | 3-9 | 3-5 | 7-10 | 5-8 | 2-5 |
| (3,5-dimethylcyclohex-3-en-1-yl)methanol | 67634-16-6 | NIL | 0.7 | 10-25 | 0.2-0.5 | 10-25 | 10-25 |
| 3-(7,7-dimethyl-4-bicyclo[3.1.1]hept-3-enyl)-2,2-dimethylpropanal | 33885-52-8 | 30-45 | 20-30 | 8-25 | 15-22 | 7-15 | 11-18 |
| Total | | 100 | 100 | 100 | 100 | 100 | 100 |

EXAMPLE 8

Liquid Fabric Spray Fabric Freshening Compositions

Examples of liquid compositions for use as fabric freshening compositions containing the malodor reducing compositions.

| | wt % Active | | | | |
|---|---|---|---|---|---|
| Ingredient | A | B | C | D | E |
| Deionized Water | Balance | Balance | Balance | Balance | Balance |
| Ethanol | 3.0 | 3.0 | 3.0 | 3.0 | 3.0 |
| Lupasol HF[1] | NIL | NIL | NIL | NIL | NIL |
| Hydroxypropyl b-CD | NIL | NIL | NIL | NIL | NIL |
| Diethylene Glycol | NIL | NIL | NIL | NIL | NIL |
| Silwet L-7600 | 0.1 | 0.1 | 0.1 | 0.100 | 0.100 |
| Basophor EL60[2] | NIL | 0.05 | 0.05 | 0.05 | 0.05 |
| Maleic Acid and/or Citric Acid[3] | As needed | As needed | As needed | As needed | As needed |
| Koralone B-119 | 0.015 | 0.015 | 0.015 | 0.015 | 0.015 |
| Hydroxypropyl β-cyclodextrin | NIL | NIL | NIL | NIL | NIL |
| Sodium Hydroxide[3] | As needed | As needed | As needed | As needed | As needed |
| Malodor Reducing Composition from EXAMPLE 4B | NIL | 0.05% | NIL | NIL | NIL |
| Malodor Reducing Composition from EXAMPLE 4C | NIL | NIL | 0.05% | NIL | NIL |
| Malodor Reducing Composition from EXAMPLE 5 | NIL | NIL | NIL | 0.05% | NIL |
| Malodor Reducing Composition from EXAMPLE 6 | NIL | NIL | NIL | NIL | 0.05% |
| Fragrance | 0 | 0 | 0 | 0 | 0 |
| Target pH | 6.8 | 6.8 | 6.8 | 6.8 | 6.8 |
| Total | 100 | 100 | 100 | 100 | 100 |

The resulting fabric refreshing spray product when used to treat fabric surfaces is effective at reducing malodor on the treated fabric. The compositions of this example were tested for FFI and BI as described above; results are shown below.

| Spray + Malodor reduction composition | FFI | BI |
|---|---|---|
| EXAMPLE 8A (NIL malodor control composition) | 0 | 2.3 |
| EXAMPLE 8B | 1.0 | 1.7 |
| EXAMPLE 8C | 0 | 1.3 |
| EXAMPLE 8D | 0 | 1.5 |
| EXAMPLE 8E | 0.75 | 1.2 |

EXAMPLE 9

Fabric Spray Compositions

A Fabric Refreshing spray composition is prepared with malodor reduction composition, utilizing the compositions shown in Example 4.

| | % wt Active | | |
|---|---|---|---|
| Ingredient | A | B | C |
| Tween 20 | 1.00 | 1.00 | 1.00 |
| Surfynol 465 | 0.059 | 0.059 | 0.059 |
| Surfynol 104PG | 0.020 | 0.020 | 0.020 |
| Arquad HTL8 | 0.49 | 0.49 | 0.49 |
| Permethyl 102A | 0.1979 | NIL | NIL |
| Triethanolamine | 0.30 | 0.30 | 0.30 |
| Triethanolamine HCL | 0.012 | 0.012 | 0.012 |
| Koralone B-119 | 0.01 | 0.01 | 0.01 |
| Composition of EXAMPLE 4A | NIL | 0.001-0.025 | 0.001-0.025 |
| Composition of EXAMPLE 5 | 0.001-0.025 | NIL | NIL |
| Composition of EXAMPLE 4D | 0-0.100 | 0-0.100 | 0-0.100 |
| Compositions of EXAMPLE 4B, 4C, or 4E | NIL | NIL | 0-0.3 |
| Composition of EXAMPLE 6 | NIL | NIL | 0-0.15 |
| Compositions of EXAMPLES 7A, 7B, 7C, 7D, 7E, or 7F | NIL | NIL | 0-0.05 |
| Low odor impact fragrance | 0.0495 | 0.0495 | 0-0.0495 |
| Water | Balance to 100.0 | Balance to 100.0 | Balance to 100.0 |
| Formula pH | 8.6 | 8.6 | 8.6 |

The compositions of EXAMPLE 9 have a low odor impact fragrance in addition to malodor reduction composition. The data below shows that a low odor impact is maintained with the blocking materials.

| | FFI | BI |
|---|---|---|
| EXAMPLE 9A | 2.0 | 1.0 |
| EXAMPLE 9B | 1.0 | 1.0 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A freshening composition having a viscosity of from about 1 mPa·s to about 50,000 mPa·, said freshening composition comprising, based on total freshening composition weight:

a) a sum total of from about 0.001% to about 0.07% of 1 to about 20 malodor reduction materials selected from the group consisting of: 1,1,2,3,3-pentamethyl-1,2,3,5,6,7-hexahydro-4H-inden-4-one; 3a,4,5,6,7,7a-hexahydro-1H-4,7-methanoinden-6-yl acetate; 1-((2-(tert-butyl)cyclohexyl)oxy)butan-2-ol; 2-(8-isopropyl-6-methylbicyclo[2.2.2]oct-5-en-2-yl)-1,3-dioxolane; (E)-oxacyclohexadec-13-en-2-one; (Z)-cyclooct-4-en-1-yl methyl carbonate; 7-methyloctyl acetate; ethyl dodecanoate; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophthalen-8(5H)-one; 8,8-dimethyl-3a,4,5,6,7,7a-hexahydro-1H-4,7-methanoinden-6-yl propionate; (Z)-non-6-en-1-ol; (E)-dec-4-enal; (1-methyl-2-((1,2,2-trimethylbicyclo[3.1.0]hexan-3-yl)methyl)cyclopropyl)methanol; 2,6-di-tert-butyl-4-methylphenol; (E)-3,7-dimethylocta-2,6-dien-1-yl palmitate; 3-methyl-5-phenylpentan- 1-ol; 3-(3,3-dimethyl-2,3-dihydro-1H-inden-5-yl)propanal; 2,2,6,6,7,8,8-heptamethyldecahydro-2H-indeno[4,5-b]furan; (R,Z)-1-(2,6,6-trimethylcyclohex-2-en-1-yl)pent-1-en-3-one; (E)-3,7-dimethylocta-1,3,6-triene; 1-(5,5-dimethylcyclohex-1-en-1-yl)pent-4-en-1-one; (E)-cyclohexadec-5-en-1-one; 2-isopropyl-5-methylphenol; and mixtures thereof;

b) from about 0.01% to about 3% of solublizing agent; and c) optionally, an adjunct ingredient.

2. The freshening composition of claim 1, a sum total of from about 0.001% to about 0.07% of 3 to 20 malodor reduction materials selected from the group consisting of: 1,1,2,3,3-pentamethyl-1,2,3,5,6,7-hexahydro-4H-inden-4-one; 3a,4,5,6,7,7a-hexahydro-1H-4,7-methanoinden-6-yl acetate; 1-((2-(tert-butyl)cyclohexyl)oxy)butan-2-ol; 2-(8-isopropyl-6-methylbicyclo[2.2.2]oct-5-en-2-yl)-1,3-dioxolane; (E)-oxacyclohexadec-13-en-2-one; (Z)-cyclooct-4-en-1-yl methyl carbonate; 7-methyloctyl acetate; ethyl dodecanoate; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophthalen-8(5H)-one; 8,8-dimethyl-3a,4,5,6,7,7a-hexahydro-1H-4,7-methanoinden-6-yl propionate; (Z)-non-6-en-1-ol; (E)-dec-4-enal; (1-methyl-2-((1,2,2-trimethylbicyclo[3.1.0]hexan-3-yl)methyl)cyclopropyl)methanol; 2,6-di-tert-butyl-4-methylphenol; (E)-3,7-dimethylocta-2,6-dien-1-yl palmitate; 3-methyl-5-phenylpentan-1-ol; 3-(3,3-dimethyl-2,3-dihydro-1H-inden-5-yl)propanal; 2,2,6,6,7,8,8-heptamethyldecahydro-2H-indeno[4,5-b]furan; (R,Z)-1-(2,6,6-trimethylcyclohex-2-en-1-yl)pent-1-en-3-one; (E)-3,7-dimethylocta-1,3,6-triene; 1-(5,5-dimethylcyclohex-1-en-1-yl)pent-4-en-1-one; (E)-cyclohexadec-5-en-1-one; 2-isopropyl-5-methylphenol; and mixtures thereof.

3. The freshening composition of claim 1, a sum total of from about 0.001% to about 0.07% of 4 to 20 malodor reduction materials selected from the group consisting of: 1,1,2,3,3-pentamethyl-1,2,3,5,6,7-hexahydro-4H-inden-4-one; 3a,4,5,6,7,7a-hexahydro-1H-4,7-methanoinden-6-yl acetate; 1-((2-(tert-butyl)cyclohexyl)oxy)butan-2-ol; 2-(8-isopropyl-6-methylbicyclo[2.2.2]oct-5-en-2-yl)-1,3-dioxolane; (E)-oxacyclohexadec-13-en-2-one; (Z)-cyclooct-4-en-1-yl methyl carbonate; 7-methyloctyl acetate; ethyl dodecanoate; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophthalen-8(5H)-one; 8,8-dimethyl-3a,4,5,6,7,7a-hexahydro-1H-4,7-methanoinden-6-yl propionate; (Z)-non-6-en-1-ol; (E)-dec-4-enal; (1-methyl-2-((1,2,2-trimethylbicyclo[3.1.0]hexan-3-yl)methyl)cyclopropyl)methanol; 2,6-di-tert-butyl-4-methylphenol; (E)-3,7-dimethylocta-2,6-dien-1-yl palmitate; 3-methyl-5-phenylpentan-1-ol; 3-(3,3-dimethyl-2,3-dihydro-1H-inden-5-yl)propanal; 2,2,6,6,7,8,8-heptamethyldecahydro-2H-indeno[4,5-b]furan; (R,Z)-1-(2,6,6-trimethylcyclohex-2-en-1-yl)pent-1-en-3-one; (E)-3,7-dimethylocta-1,3,6-triene; 1-(5,5-dimethylcyclohex-1-en-1-yl)pent-4-en-1-one; (E)-cyclohexadec-5-en-1-one; 2-isopropyl-5-methylphenol; and mixtures thereof.

4. The freshening composition of claim 1, a sum total of from about 0.001% to about 0.07% of 5 to 20 malodor reduction materials selected from the group consisting of: 1,1,2,3,3-pentamethyl-1,2,3,5,6,7-hexahydro-4H-inden-4-one; 3a,4,5,6,7,7a-hexahydro-1H-4,7-methanoinden-6-yl acetate; 1-((2-(tert-butyl)cyclohexyl)oxy)butan-2-ol; 2-(8-isopropyl-6-methylbicyclo[2.2.2]oct-5-en-2-yl)-1,3-dioxolane; (E)-oxacyclohexadec-13-en-2-one; (Z)-cyclooct-4-en-1-yl methyl carbonate; 7-methyloctyl acetate; ethyl dodecanoate; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophthalen-8(5H)-one; 8,8-dimethyl-3a,4,5,6,7,7a-hexahydro-1H-4,7-methanoinden-6-yl propionate; (Z)-non-6-en-1-ol; (E)-dec-4-enal; (1-methyl-2-((1,2,2-trimethylbicyclo[3.1.0]hexan-3-yl)methyl)cyclopropyl)methanol; 2,6-di-tert-butyl-4-methylphenol; (E)-3,7-dimethylocta-2,6-dien-1-yl palmitate; 3-methyl-5-phenylpentan- 1-ol; 3-(3,3-dimethyl-2,3-dihydro-1H-inden-5-yl)propanal; 2,2,6,6,7,8,8-heptamethyldecahydro-2H-indeno[4,5-b]furan; (R,Z)-1-(2,6,6-trimethylcyclohex-2-en-1-yl)pent-1-en-3-one; (E)-3,7-dimethylocta-1,3,6-triene; 1-(5,5-dimethylcyclohex-1-en-1-yl)pent-4-en-1-one; (E)-cyclohexadec-5-en-1-one; 2-isopropyl-5-methylphenol; and mixtures thereof.

5. The freshening composition according to claim 1, wherein said sum total of malodor reduction materials has a Blocker Index of less than 3 and/or a Blocker Index average of 3 to about 0.001.

6. The freshening compositions according to claim 5, wherein each of said malodor reduction materials has a MORV of at least 0.5.

7. The freshening composition according to claim 1, wherein each of said malodor reduction materials has a MORV of at least 0.5.

8. The freshening composition according to claim 1, said sum total of malodor reduction materials has a Fragrance Fidelity Index average of 3 to about 0.001, or each malodor reduction material in said sum total of malodor reduction materials has a Fragrance Fidelity Index of less than 3.

9. The freshening composition according to claim 1 comprising one or more perfume raw materials, said freshening composition having a weight ratio of parts of malodor reduction materials to parts of perfume from about 1:20,000 to about 3000:1.

10. The freshening composition according to claim 1, said composition comprising an adjunct ingredient selected from the group consisting of isoalkanes comprising at least 12 carbon atoms, a compound comprising a quatenary amine moiety, lubricants, additional solvents glycols, alcohols, silicones, preservatives, anti-microbial agents, pH modifiers, a carrier, insect repellants, metallic salts, cyclodextrins, functional polymers, anti-foaming agents, antioxidants, oxidizing agents, chelants and mixtures thereof.

* * * * *